US012565520B2

(12) United States Patent
Kennedy et al.

(10) Patent No.: US 12,565,520 B2
(45) Date of Patent: Mar. 3, 2026

(54) CHEMICALLY-STABILIZED ALLOSTERIC MODULATORS OF LEUCINE-RICH REPEAT KINASE 2 (LRRK2)

(71) Applicants:UNIVERSITY OF GEORGIA RESEARCH FOUNDATION, INC., Athens, GA (US); RIJKSUNIVERSITEIT GRONINGEN, Groningen (DE)

(72) Inventors: Eileen J. Kennedy, Athens, GA (US); Arjan Kortholt, Groningen (NL); Leah G. Helton, Chattanooga, TN (US)

(73) Assignees: UNIVERSITY OF GEORGIA RESEARCH FOUNDATION, INC., Athens, GA (US); RIJKSUNIVERSITEIT GRONINGEN, Groningen (NL)

( * ) Notice: Subject to any disclaimer, the term of this patent is extended or adjusted under 35 U.S.C. 154(b) by 818 days.

(21) Appl. No.: 17/802,388

(22) PCT Filed: Feb. 25, 2021

(86) PCT No.: PCT/US2021/019616
§ 371 (c)(1),
(2) Date: Aug. 25, 2022

(87) PCT Pub. No.: WO2021/173802
PCT Pub. Date: Sep. 2, 2021

(65) Prior Publication Data
US 2023/0220019 A1       Jul. 13, 2023

Related U.S. Application Data

(60) Provisional application No. 62/981,276, filed on Feb. 25, 2020.

(30) Foreign Application Priority Data

Apr. 17, 2020       (EP) ..................................... 20170251

(51) Int. Cl.
*C07K 14/435* (2006.01)
*A61K 38/00* (2006.01)
*C12N 9/12* (2006.01)

(52) U.S. Cl.
CPC ............. *C07K 14/435* (2013.01); *C12N 9/12* (2013.01); *A61K 38/00* (2013.01)

(58) Field of Classification Search
None
See application file for complete search history.

(56) References Cited

U.S. PATENT DOCUMENTS 5,411,737 A       5/1995   Hsu et al.
2016/0250182 A1   9/2016   Abeliovich

FOREIGN PATENT DOCUMENTS

WO       2008091799 A2    7/2008
WO       2008121767 A2    10/2008
WO       2020/180257 A1   9/2020

OTHER PUBLICATIONS

Deng et al. "Structures of the ROC domain from the Parkinson's disease-associated leucine-rich repeat kinase 2 reveals a dimeric GTPase" Proc. Nat. Acad. Sci. 105:1499-1504. (Year: 2008).*
Deniston et al. "Cryo-EM structure of the C-terminal half of the Parkinson's disease-2 linked protein leucine rich repeat kinase 2 (LRRK2)" PDB Deposit 6VNO. (Year: 2020).*
International Search Report and Written Opinion received in PCT/US2021/019616 dated May 27, 2021, 11 pages.
Kortholt, "Allosteric targeting of LRRK2 using stapled peptides", The Michael J. Fox Foundation for Parkinson's Research, Aug. 6, 2020 (Aug. 6, 2020), p. 1 of 1. Retrieved from the Internet:<https://www.michaetjfox.org/granUal1osteric-targeting-lrrk2-using-stapled-peptides> on May 11, 2021 (May 11, 2021), entire document.
Klein et al., "Homo- and heterodimerization of ROCO kinases: LRRK2 kinase inhibition by the LRRK2 ROCO fragment", Journal of Neurochemistry, Oct. 12, 2009 (Oct. 12, 2009), vol. 111, Iss. 3, pp. 703-715, entire document.
Fulton et al., "Conformationally constrained peptides target the allosteric kinase dimer interface and inhibit EGFR activation", Bioorganic & Medicinal Chemistry, Sep. 5, 2017 (Sep. 5, 2017), vol. 26, Iss. 6, pp. 1167-1173, entire document.
Deniston et al., "Parkinson's Disease-linked LRRK2 structure and model for microtubule interaction", BioRxiv, Jan. 6, 2020 (Jan. 6, 2020}, pp. 1-11, entire document.
Schafmeister et al., "An All-Hydrocarbon Cross-Linking System for Enhancing the Helicity and Metabolic Stability of Peptides", Journal of the American Chemical Society, Jun. 6, 2000 (Jun. 6, 2000), vol. 122, Iss. 24, pp. 5891-5892, entire document.
Manschwetus et al., "Binding of the Human 14-3-3 Isoforms to Distinct Sites in the Leucine-Rich Repeat Kinase 2", Frontiers in Neuroscience, Apr. 7, 2020 (Apr. 7, 2020), vol. 14, No. 302, pp. 1-11, entire document.
Soliman et al., "Allosteric inhibition of LRRK2, where are we now", Biochemical Society Transactions, Oct. 20, 2020 (Oct. 20, 2020}, vol. 48, pp. 2185-2194, entire document.
Supplementary European Search Report in 21759528.9 dated May 28, 2024.
Dong et al., "Identification of peptides interfering the lrrk2/ pp1 interaction", bioRxiv, Oct. 16, 2019 (Oct. 16, 2019), XP055727321, 001: 10.1101/807487 Retrieved from the Internet: URL:https://www.biorxiv.org/content/10.1101/807487v1.full.pdf [retrieved on Sep. 3, 2020].

(Continued)

*Primary Examiner* — Fred H Reynolds
*Assistant Examiner* — Zachary J Miknis
(74) *Attorney, Agent, or Firm* — Meunier Carlin & Curfman LLC

(57)       ABSTRACT

The present disclosure describes synthetic polypeptides for the inhibition or modulation of the activity of leucine-rich repeat kinase 2 (LRRK2) along with methods of using the same in the treatment of medical conditions, for example neurological diseases or disorders.

12 Claims, 9 Drawing Sheets

Specification includes a Sequence Listing.

(56) References Cited

OTHER PUBLICATIONS

Wild et al., "Potential for therapeutic targeting of AKAP signaling complexes in nervous system disorders", Pharmacology & Therapeutics, Elsevier, GB, vol. 185, Dec. 17, 2017 (Dec. 17, 2017), pp. 99-121, XP085376491, ISSN: 0163-7258, DOI: 10.1016/J. PHARMTHERA.2017.12.004.

Lewis, P.A., et al. LRRK2 and Human Disease: A Complicated Question or a Question of Complexes? Science Signaling 2012, 5(207):e2.

Ness, D. et al. Leucine-rich repeat kinase 2 (LRRK2)-deficient rats exhibit tubule injury and perturbations in metabolic and immunological homeostasis. PLoS One 8, e66164, (2013) pp. 1-12.

Herzig, M.C. et al. LRRK2 protein levels are determined by kinase function and are crucial for kidney and lung homeostasis in mice. Hum. Mol. Genet. 20, pp. 4209-4223, (2011).

Tong, Y. et al. Loss of leucine-rich repeat kinase 2 causes age dependent bi-phasic alterations of the autophagy pathway. Mol. Neurodegener. 7, 2, (2012), pp. 1-16.

Ramirez, M.B. et al. GTP binding regulates cellular localization in Parkinson's disease-associated LRRK2. Hum. Mol. Genet. 26, 2747-2767 (2017).

Dzamko, N. et al. Inhibition of LRRK2 kinase activity leads to dephosphorylation of Ser(910)/Ser(935), disruption of 14-3-3 binding and altered cytoplasmic localization Biochem. J. 430, 405-413 (2010).

Kett L.R. et al. LRRK2 Parkinson disease mutations enhances its microtubule association. Hum. Mol. Genet. 21, 890-899 (2012).

Deniston, C. K. et al. (2020) Parkinson's Disease-linked LRRK2 structure and model for microtubule interaction. bioRxiv.

Webber, P. J. et al. Autophosphorylation in the leucine-rich repeat kinase 2 (LRRK2) GTPase domain modifies kinase and GTP-binding activity. J. Mol. Biol. 412, 94-110 (2011).

Greggio, E. et al. The Parkinson disease-associated leucine-rich repeat kinase 2 (LRRK2) is a dimer that undergoes intramolecular autophosphorylation. J. Biol. Chem. 283, 16906-14 (2008).

Berger, X. et al. Membrane localization of LRRK2 is associated with increased formation of the highly active LRRK2 dimer and changes in its phosphorylation. Biochemistry 49, 5511-5523.

Li, X. et al. Phosphorylation-Dependent 14-3-3 Binding to LRRK2 Is Impaired by Common Mutations of Familial Parkinson's Disease. PLoS One 6, 1-13 (2011).

Nichols, R. J. et al. 14-3-3 binding to LRRK2 is disrupted by multiple Parkinson's disease-associated mutations and regulations cytoplasmic localization. Biochem. J. 430, 393-404 (2010).

Rudenko, I. N. et al. 14-3-3-proteins are promising LRRK2 interactors. Biochem. J. 430, e5-6 (2010).

Purlyte, E. et al. Rab29 activation of the Parkinson's disease-associated LRRK2 kinase. EMBO J. e201798099 (2017). Doi:10. 15252/embj.201798099.

Verdine et al., Chapter One: Stapled Peptides for Intracellular Drug Targets, Methods Enzymol. 2012, 503:3-33.

Kutchukian et al., An all-atom model for stabilization of a-helical structure in peptides by hydrocarbon staples J. Am. Chem. Soc. 2009, 131:4622-4627.

Oller-Salvia, B. et al., Blood-brain barrier shuttle peptides: an emerging paradigm for brain delivery, Chem Soc Rev, 45 (2016) 4690-4707).

International Preliminary Report on Patentability for International Application No. PCT/US2021/019616 dated Sep. 9, 2022, 7 pages.

Civiero et al., Biochemical Characterization of Highly Purified Leucine-Rich Repeat Kinases 1 and 2 Demonstrates Formation of Homodimers. PLOS ONE 7, e43472 (2012).

Leemans et al., Allosteric modulation of the GTPase activity of a bacterial LRRK2 homolog by conformation-specific Nanobodies. Biochem J 477, 1203-1218 (2020).

Sen et al., Dependence of leucine-rich repeat kinase 2 (LRRK2) kinase activity on dimerization. J Biol Chem 284, 36346-36356 (2009).

Teng, Y. et al., The WASF3-NCKAPI-CYFIP1 Complex Is Essential for Breast Cancer Metastasis, Cancer Res 2016, 76(17):5133-42.

Wang, Y. et al., PKA-Type I Selective Constrained Peptide Disruptors of AKAP Complexes, ACS Chem Biol Jun. 9, 2015, 10(6):1502-10.

Wang, Y. et al., Isoform-Selective Disruption of AKAP-Localized PKA Using Hydrocarbon Stapled Peptides, ACS Chem Biol 2014, 9(3):635-642.

Blackwell, H. E. et al., Highly Efficient Synthesis of Covalently Cross-Linked Peptide Helices by Ring-Closing Metathesis. Angew Chem Int Ed Engl 37, 3281-3284, 1998.

Walensky, L.D. et al., Hydrocarbon-stapled peptides: principles, practice, and progress, J. Med. Chem. Aug. 14, 2014, 57:6275-6288.

Lau, Y. H. et al., Peptide stapling techniques based on different macrocyclisation chemistries, Chem. Soc. Rev. 2014, 00:1-12.

Joy, S.T., et al., Optimal Hydrogen-Bond Surrogate for alpha-Helices, Chem. Commun. Apr. 28, 2016, 52(33):5738-5741.

Zhao, H. et al., Crosslinked Aspartic Acids as Helix-Nucleating Templates, Angew. Chem. Int. Ed. 2016, 55:12088-12093.

Sambrook et al., Molecular Cloning: A Laboratory Manual, Second Edition, Cold Spring Harbor Laboratory Press, Cold Spring Harbor, N.Y. (1989).

Dorsey, E.R. et al., Projected No. of people with Parkinson disease in the most populous nations, 2005 through 2030. Neurology 68, 384-386 (2007).

Deyaert, E. et al., A homologue of the Parkinson's disease-associated protein LRRK2 undergoes a monomer-dimer transition during GTP turnover, Nat Commun, 8 (2017) 1008).

Gotthardt, K. et al., Structure of the Roc-COR domain tandem of C. tepidum, a prokaryotic homologue of the human LRRK2 Parkinson kinase. EMBO J 27, 2239-2249 (2008).

Terheyden, S. et al., Revisiting the Roco G-protein cycle. Biochem J 465, 139-147 (2015).

Gilsbach, B.K. et al., Structural biology of the LRRK2 GTPase and kinase domains: implications for regulation. Front Mol Neurosci 7, 32 (2014).

Rosenbusch, K.E. et al., Activation Mechanism of LRRK2 and Its Cellular Functions in Parkinson's Disease. Parkinsons Dis 2016, 7351985 (2016).

Dauer, W. et al., Parkinson's disease: mechanisms and models. Neuron 39, 889-909 (2003).

Klein, C. et al., Genetics of Parkinson's disease. Cold Spring Harb Perspect Med 2, a008888 (2012).

Kibat, J. et al., Utilisation of antibody microarrays for the selection of specific and informative antibodies from recombinant library binders of unknown quality, N Biotechnol, 33 (2016) 574-581.

Guaitoli, G. et al., Structural model of the dimeric Parkinson's protein LRRK2 reveals a compact architecture involving distant interdomain contacts, Proc Natl Acad Sci USA, 113 (2016) 30 E4357-4366.

Antoniou, N. et al., A motif within the armadillo repeat of Parkinson's-linked LRRK2 interacts with FADD to hijack the extrinsic death pathway. Sci Rep 8, 3455 (2018).

Gilsbach, B.K. et al., Roco kinase structures give insights into the mechanism of Parkinson disease-related leucine-rich-repeat kinase 2 mutations. Proc Natl Acad Sci U S 5 A 109, 10322-10327 (2012).

Deyaert, E. et al., Structure and nucleotide-induced conformational dynamics of the Chlorobium tepidum Roco protein. Biochem J 476, 51-66 (2019).

Nguyen, A.P. et al., Understanding the GTPase Activity of LRRK2: Regulation, Function, and Neurotoxicity. Adv Neurobiol 14, 71-88 (2017).

Baptista et al., Loss of leucine-rich repeat kinase 2 (LRRK2) in rats leads to progressive abnormal phenotypes in peripheral organs. PLoS One 8, e80705 (2013).

Mansuy D., et al. "Métathèse et catalyse à l'honneur," Med Sci (Paris). 2005 21(11):995-6. Machine Translation Included.

Flaherty, "Targeted Inhibition of Plasmodium falciparum Calcium-Dependent Protein Kinase 1 with a Constrained J Domain-Derived Disruptor Peptide" et al. ACS Infect Dis 2019, 5(4):506-514.

Blackwell et al., Ring-Closing Metathesis of Olefinic Peptides: Design, Synthesis, and Structural Characterization of Macrocyclic Helical Peptides. J. Org. Chem. 2001, 66, 5291-5302.

(56) References Cited

OTHER PUBLICATIONS

Sheng, Z. et al., Ser1292 autophosphorylation is an indicator of LRRK2 kinase activity and contributes to the cellular effects of PD mutations. Sci Transl Med 4, 164ra161 (2012).

Duvoisin, R.C., Recent advances in the genetics of Parkinson's disease. Adv Neurol 69, 33-40 (1996).

Polymeropoulos, M.H. et al., Mutation in the alpha-synuclein gene identified in families with Parkinson's disease. Science 276, 2045-2047 (1997).

Kruger, R. et al., Ala30Pro mutation in the gene encoding alpha-synuclein in Parkinson's disease. Nat Genet 18, 106-108 (1998.

Farrer, M. et al., A chromosome 4p haplotype segregating with Parkinson's disease and postural tremor. Hum Mol Genet 8, 81-85 (1999).

Gasser, T. et al., A susceptibility locus for Parkinson's disease maps to chromosome 2p13. Nat Genet 18, 262-265 (1998.

Gasser, T., Mendelian forms of Parkinson's disease. Biochim Biophys Acta 1792, 587-596 (2009).

Zimprich, A. et al., Mutations in LRRK2 cause autosomal-dominant parkinsonism with pleomorphic pathology. Neuron 44, 601-607 (2004).

Verstraeten, A. et al., Progress in unraveling the genetic etiology of Parkinson disease in a genomic era. Trends Genet 31, 140-149 (2015.

Biosa, A. et al., GTPase activity regulates kinase activity and cellular phenotypes of Parkinson's disease-associated LRRK2. Hum Mol Genet 22, 1140-1156 (2013).

Mata, I.F. et al., LRRK2 30 in Parkinson's disease: protein domains and functional insights. Trends Neurosci 29, 286-293 (2006).

Li, J.Q. et al., The role of the LRRK2 gene in Parkinsonism. Mol Neurodegener 9, 47 (2014).

Tolosa, et al., LRRK2 in Parkinson disease: challenges of clinical trials. Nat Rev Neurol 5 10.1038/s41582-019-0301-2 (2020).

Simon-Sanchez et al., Genome-wide association study reveals genetic risk underlying Parkinson's disease. Nat Genet 41, 1308-1312 (2009.

Di Maio et al., LRRK2 activation in idiopathic Parkinson's disease. Sci Transl Med 10 (2018)).

Deng et al., Leucine-rich repeat kinase 2 inhibitors: a patent review (2006-2011). Expert Opin Ther Pat 22, 1415-1426 (2012).

Fuji et al., Effect of selective LRRK2 kinase inhibition on nonhuman primate lung. Sci Transl Med 7, 273ra215 (2015).

Steger et al., Phosphoproteomics reveals that Parkinson's disease kinase LRRK2 regulates a subset of Rab GTPases. Elife 5, 2016.

James et al., Number and brightness analysis of LRRK2 30 oligomerization in live cells. Biophys J 102, L41-43, 2012.

Yin et al., alpha-Synuclein interacts with the switch region of Rab8a in a Ser129 phosphorylation-dependent manner. Neurobiol Dis 70, 149-161 (2014).

Liu et al., LRRK2 phosphorylates membrane-bound Rabs and is activated by GTP-bound Rab7L1 to promote recruitment to the trans-Golgi network. Hum Mol Genet 27, 385-395 (2018).

Wu et al., Parkinson's disease-associated mutations in the GTPase domain of LRRK2 impair its nucleotide-dependent conformational dynamics. J Biol Chem 294, 5907-5913 (2019).

Sanstrum et al., Fluctuation Imaging of LRRK2 Reveals that the G2019S Mutation Alters Spatial and Membrane Dynamics. Molecules 25, 2020.

Deniston, et al. Structure of LRRK2 in Parkinson's disease and model for microtubule interaction. Nature 2020, 588(7837):344-349).

Nichols et al., Genetic screening for a single common LRRK2 mutation in familial Parkinson's disease. Lancet 365, 410-412, 2005.

Kachergus et al., Identification of a novel LRRK2 mutation linked to autosomal dominant parkinsonism: evidence of a common founder across European populations. Am J Hum Genet 76, 672-680, 2005.

Bonifati, Parkinson's disease: the LRRK2-G2019S mutation: opening a novel era in Parkinson's disease genetics. Eur J Hum Genet 14, 1061-1062 (2006).

West et al., Parkinson's disease-associated mutations in leucine-rich repeat kinase 2 augment kinase activity. Proc Natl Acad Sci U S A 102, 16842-16847, 2005.

Watanabe et al., The In Situ Structure of Parkinson's Disease-Linked LRRK2. Cell 182, 1508-1518 (2020).

Berwick et al., LRRK2 Biology from structure to dysfunction: research progresses, but the themes remain the same. Mol Neurodegener 14, 49, 2019.

Schmidt et al., Conformation and dynamics of the kinase domain drive subcellular location and activation of LRRK2. bioRxiv 10.1101/2020.07.13.198069, 2020.

Taylor et al., Kinase Domain Is a Dynamic Hub for Driving LRRK2 Allostery. Front Mol Neurosci 13, 538219 (2020).

Saez-Atienzar et al., The LRRK2 inhibitor GSK2578215A induces protective autophagy in SH-SY5Y cells: involvement of Drp-1-mediated mitochondrial fission and mitochondrial-derived ROS signaling. Cell Death Dis 5, e1368, 2014.

Kim et al., Stereochemical effects of all-hydrocarbon tethers in i,i+4 stapled peptides. Bioorg Med Chem Lett 19, 2533-2536, 2009.

Helton et al., Targeting Plasmodium with constrained 10 peptides and peptidomimetics. IUBMB Life 72, 1103-1114, 2020.

Bendzunas et al., Investigating PKA-RII specificity using analogs of the PKA:AKAP peptide inhibitor STAD-2. Bioorg Med Chem 26, 1174-1178 (2018.

Manschwetus et al., A Stapled Peptide Mimic of the Pseudosubstrate Inhibitor PKI Inhibits Protein Kinase A. Molecules 24(8), 1567, 2019.

Cowell et al., Suppression of Breast Cancer Metastasis Using Stapled Peptides Targeting the WASF Regulatory Complex. Cancer Growth Metastasis 2017, 10, 1-9.

Heo et al., LRRK2 enhances oxidative stress-induced neurotoxicity via its kinase activity. Experimental Cell Research 316, 649-656 (2010).

Hanold et al., Targeting kinase signaling pathways with constrained peptide scaffolds. Pharmacol Ther 173, 159-170, 2017.

Daniels et al., Insight into the mode of action of the LRRK2 Y1699C pathogenic mutant. Journal of Neurochemistry 116, 304-315 (2011).

Kim et al., LRRK2 kinase plays a critical role in manganese-induced inflammation and apoptosis in microglia. PLoS One 14, e0210248 (2019).

Gardet et al., LRRK2 Is Involved in the IFN-γ Response and Host Response to Pathogens. The Journal of Immunology 200, 185, 5577.

Fernandez-Suarez et al., Protein-protein interaction detection in vitro and in cells by proximity biotinylation. J Am Chem Soc 2008, 130, 29, 9251-9253.

Nguyen et al., Dopaminergic neurodegeneration induced by Parkinson's disease-linked G2019S LRRK2 is dependent on kinase and GTPase activity. Proc Natl Acad Sci USA 117, 17296-17307, 2020.

Skibinski et al., Mutant LRRK2 toxicity in neurons depends on LRRK2 levels and synuclein but not kinase activity or inclusion bodies. J Neurosci 34, 418-433 (2014).

* cited by examiner

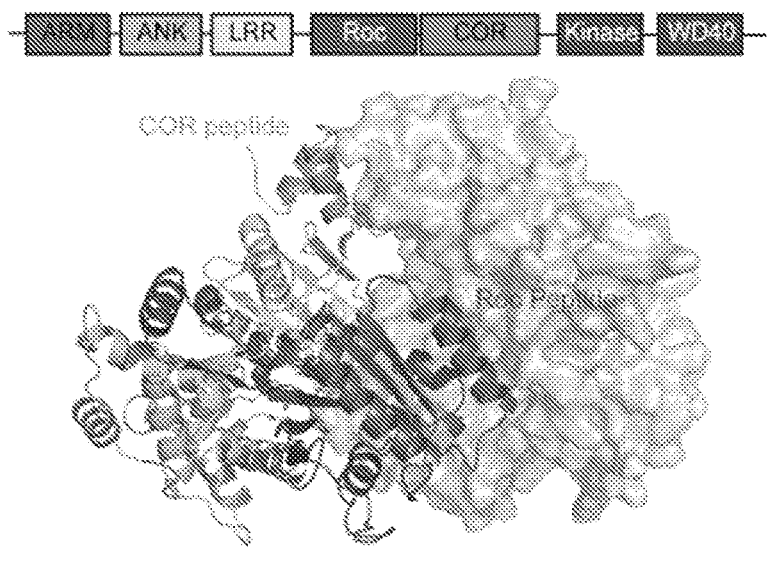

FIG. 1A

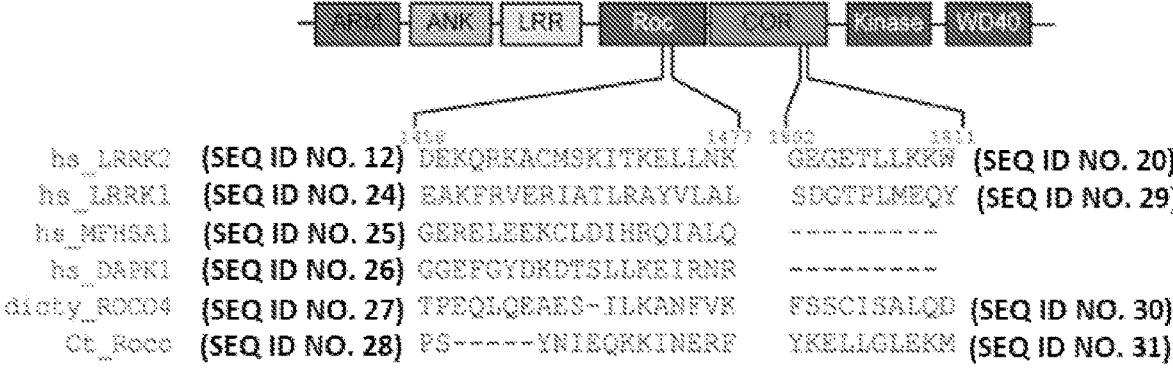

| hs_LRRK2 | (SEQ ID NO. 12) | DEKQRKACMSKITKELLNK | GEGETLLKKN | (SEQ ID NO. 20) |
|---|---|---|---|---|
| hs_LRRK1 | (SEQ ID NO. 24) | EAKFRVERIATLRAYVLAL | SDGTPLMEQY | (SEQ ID NO. 29) |
| hs_MFHSA1 | (SEQ ID NO. 25) | GERELEEKCLDIHRQIALQ | ---------- | |
| hs_DAPK1 | (SEQ ID NO. 26) | GGEFGYDKDTSLLKEIRNR | ---------- | |
| dicty_ROCO4 | (SEQ ID NO. 27) | TPEQLQEAES-ILKANFVK | FSSCISALQD | (SEQ ID NO. 30) |
| Ct_Roco | (SEQ ID NO. 28) | PS-----YNIEQRKINERF | YKELLGLEKM | (SEQ ID NO. 31) |

FIG. 1B

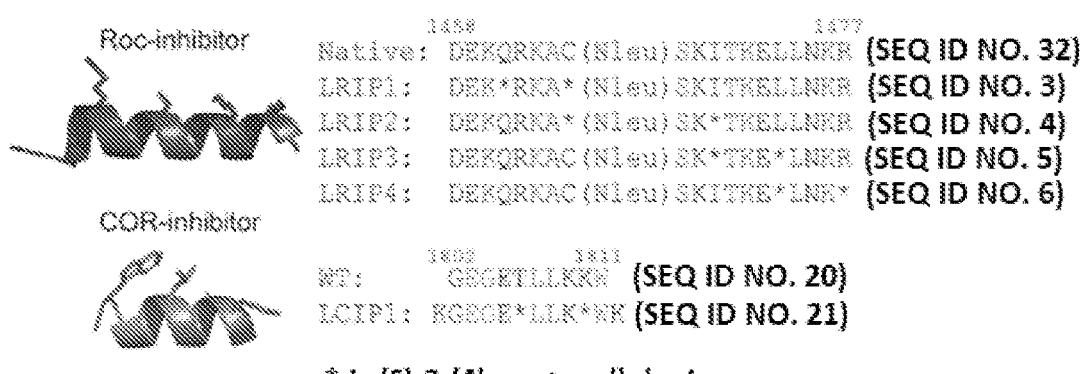

Roc-inhibitor

| Native: | DEKQRKAC(Nleu)SKITKELLNNR | (SEQ ID NO. 32) |
|---|---|---|
| LRIP1: | DEK*RKA*(Nleu)SKITKELLNNR | (SEQ ID NO. 3) |
| LRIP2: | DEKQRKA*(Nleu)SK*TKELLNNR | (SEQ ID NO. 4) |
| LRIP3: | DEKQRKAC(Nleu)SK*TKE*LNNR | (SEQ ID NO. 5) |
| LRIP4: | DEKQRKAC(Nleu)SKITKE*LNR* | (SEQ ID NO. 6) |

COR-inhibitor

| WT: | GEGETLLKKN | (SEQ ID NO. 20) |
|---|---|---|
| LCIP1: | KGEGE*LLK*NK | (SEQ ID NO. 21) |

\* is (S)-2-(4'-pentenyl)alanine

FIG. 1C

SEQUENCE LISTING

<160> NUMBER OF SEQ ID NOS: 32

<210> SEQ ID NO 1
<211> LENGTH: 20
<212> TYPE: PRT
<213> ORGANISM: Artificial Sequence
<220> FEATURE:
<223> OTHER INFORMATION: ROC domain peptide

<400> SEQUENCE: 1

Asp Glu Lys Gln Arg Lys Ala Cys Met Ser Lys Ile Thr Lys Glu Leu
1               5                   10                  15

Leu Asn Lys Arg
            20

<210> SEQ ID NO 2
<211> LENGTH: 15
<212> TYPE: PRT
<213> ORGANISM: Artificial Sequence
<220> FEATURE:
<223> OTHER INFORMATION: ROC domain peptide

<400> SEQUENCE: 2

Glu Lys Gln Arg Lys Ala Cys Met Ser Lys Ile Thr Lys Glu Leu
1               5                   10                  15

<210> SEQ ID NO 3
<211> LENGTH: 20
<212> TYPE: PRT
<213> ORGANISM: Artificial Sequence
<220> FEATURE:
<223> OTHER INFORMATION: ROC domain peptide
<220> FEATURE:
<221> NAME/KEY: MISC_FEATURE
<222> LOCATION: (4)..(4)
<223> OTHER INFORMATION: Xaa is (S)-2-(4'-pentenyl)alanine
<220> FEATURE:
<221> NAME/KEY: MISC_FEATURE
<222> LOCATION: (8)..(8)
<223> OTHER INFORMATION: Xaa is (S)-2-(4'-pentenyl)alanine
<220> FEATURE:
<221> NAME/KEY: MISC_FEATURE
<222> LOCATION: (9)..()
<223> OTHER INFORMATION: Xaa is Norleucine
<220> FEATURE:
<221> NAME/KEY: MISC_FEATURE
<222> LOCATION: (9)..(9)
<223> OTHER INFORMATION: Xaa is Norleucine

<400> SEQUENCE: 3

Asp Glu Lys Xaa Arg Lys Ala Xaa Xaa Ser Lys Ile Thr Lys Glu Leu
1               5                   10                  15

Leu Asn Lys Arg
            20

<210> SEQ ID NO 4
<211> LENGTH: 20
<212> TYPE: PRT
<213> ORGANISM: Artificial Sequence
<220> FEATURE:
<223> OTHER INFORMATION: ROC domain peptide
<220> FEATURE:
<221> NAME/KEY: MISC_FEATURE
<222> LOCATION: (8)..(8)
<223> OTHER INFORMATION: Xaa is (S)-2-(4'-pentenyl)alanine
<220> FEATURE:
<221> NAME/KEY: MISC_FEATURE
<222> LOCATION: (9)..(9)
<223> OTHER INFORMATION: Xaa is norleucine
<220> FEATURE:

```
<221> NAME/KEY: MISC_FEATURE
<222> LOCATION: (12)..(12)
<223> OTHER INFORMATION: Xaa is (S)-2-(4'-pentenyl)alanine

<400> SEQUENCE: 4

Asp Glu Lys Gln Arg Lys Ala Xaa Xaa Ser Lys Xaa Thr Lys Glu Leu
1               5                   10                  15

Leu Asn Lys Arg
            20

<210> SEQ ID NO 5
<211> LENGTH: 20
<212> TYPE: PRT
<213> ORGANISM: Artificial Sequence
<220> FEATURE:
<223> OTHER INFORMATION: ROC domain peptide
<220> FEATURE:
<221> NAME/KEY: MISC_FEATURE
<222> LOCATION: (9)..(9)
<223> OTHER INFORMATION: Xaa is norleucine
<220> FEATURE:
<221> NAME/KEY: MISC_FEATURE
<222> LOCATION: (12)..(12)
<223> OTHER INFORMATION: Xaa is (S)-2-(4'-pentenyl)alanine
<220> FEATURE:
<221> NAME/KEY: MISC_FEATURE
<222> LOCATION: (16)..(16)
<223> OTHER INFORMATION: Xaa is (S)-2-(4'-pentenyl)alanine

<400> SEQUENCE: 5

Asp Glu Lys Gln Arg Lys Ala Cys Xaa Ser Lys Xaa Thr Lys Glu Xaa
1               5                   10                  15

Leu Asn Lys Arg
            20

<210> SEQ ID NO 6
<211> LENGTH: 20
<212> TYPE: PRT
<213> ORGANISM: Artificial Sequence
<220> FEATURE:
<223> OTHER INFORMATION: ROC domain petide
<220> FEATURE:
<221> NAME/KEY: MISC_FEATURE
<222> LOCATION: (9)..(9)
<223> OTHER INFORMATION: Xaa is norleucine
<220> FEATURE:
<221> NAME/KEY: MISC_FEATURE
<222> LOCATION: (16)..(16)
<223> OTHER INFORMATION: Xaa is (S)-2-(4'-pentenyl)alanine
<220> FEATURE:
<221> NAME/KEY: MISC_FEATURE
<222> LOCATION: (20)..(20)
<223> OTHER INFORMATION: Xaa is (S)-2-(4'-pentenyl)alanine

<400> SEQUENCE: 6

Asp Glu Lys Gln Arg Lys Ala Cys Xaa Ser Lys Ile Thr Lys Glu Xaa
1               5                   10                  15

Leu Asn Lys Xaa
            20

<210> SEQ ID NO 7
<211> LENGTH: 15
<212> TYPE: PRT
<213> ORGANISM: Artificial Sequence
<220> FEATURE:
<223> OTHER INFORMATION: ROC domain peptide
<220> FEATURE:
<221> NAME/KEY: MISC_FEATURE
<222> LOCATION: (3)..(3)
<223> OTHER INFORMATION: Xaa is (S)-2-(4'-pentenyl)alanine
```

-continued

```
<220> FEATURE:
<221> NAME/KEY: MISC_FEATURE
<222> LOCATION: (7)..(7)
<223> OTHER INFORMATION: Xaa is (S)-2-(4'-pentenyl)alanine

<400> SEQUENCE: 7

Glu Lys Xaa Arg Lys Ala Xaa Met Ser Lys Ile Thr Lys Glu Leu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: ROC domain peptide
<220> FEATURE:
<221> NAME/KEY: MISC_FEATURE
<222> LOCATION: (4)..(4)
<223> OTHER INFORMATION: Xaa is (S)-2-(4'-pentenyl)alanine
<220> FEATURE:
<221> NAME/KEY: MISC_FEATURE
<222> LOCATION: (8)..(8)
<223> OTHER INFORMATION: Xaa is (S)-2-(4'-pentenyl)alanine

<400> SEQUENCE: 8

Glu Lys Gln Xaa Lys Ala Cys Xaa Ser Lys Ile Thr Lys Glu Leu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: ROC domain peptide
<220> FEATURE:
<221> NAME/KEY: MISC_FEATURE
<222> LOCATION: (7)..(7)
<223> OTHER INFORMATION: Xaa is (S)-2-(4'-pentenyl)alanine
<220> FEATURE:
<221> NAME/KEY: MISC_FEATURE
<222> LOCATION: (11)..(11)
<223> OTHER INFORMATION: Xaa is (S)-2-(4'-pentenyl)alanine

<400> SEQUENCE: 9

Glu Lys Gln Arg Lys Ala Xaa Met Ser Lys Xaa Thr Lys Glu Leu
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: ROC domain peptide
<220> FEATURE:
<221> NAME/KEY: MISC_FEATURE
<222> LOCATION: (8)..(8)
<223> OTHER INFORMATION: Xaa is (S)-2-(4'-pentenyl)alanine
<220> FEATURE:
<221> NAME/KEY: MISC_FEATURE
<222> LOCATION: (12)..(12)
<223> OTHER INFORMATION: Xaa is (S)-2-(4'-pentenyl)alanine

<400> SEQUENCE: 10

Glu Lys Asp Arg Lys Ala Cys Xaa Ser Lys Ile Xaa Lys Glu Leu
1               5                   10                  15

<210> SEQ ID NO 11
<211> LENGTH: 15
<212> TYPE: PRT
<213> ORGANISM: Artificial Sequence
<220> FEATURE:
```

```
<223> OTHER INFORMATION: ROC domain peptide
<220> FEATURE:
<221> NAME/KEY: MISC_FEATURE
<222> LOCATION: (11)..(11)
<223> OTHER INFORMATION: Xaa is (S)-2-(4'-pentenyl)alanine
<220> FEATURE:
<221> NAME/KEY: MISC_FEATURE
<222> LOCATION: (15)..(15)
<223> OTHER INFORMATION: Xaa is (S)-2-(4'-pentenyl)alanine

<400> SEQUENCE: 11

Glu Lys Gln Arg Lys Ala Cys Met Ser Lys Xaa Thr Lys Glu Xaa
1               5                   10                  15

<210> SEQ ID NO 12
<211> LENGTH: 19
<212> TYPE: PRT
<213> ORGANISM: Artificial Sequence
<220> FEATURE:
<223> OTHER INFORMATION: ROC domain peptide

<400> SEQUENCE: 12

Asp Glu Lys Gln Arg Lys Ala Cys Met Ser Lys Ile Thr Lys Glu Leu
1               5                   10                  15

Leu Asn Lys

<210> SEQ ID NO 13
<211> LENGTH: 20
<212> TYPE: PRT
<213> ORGANISM: Artificial Sequence
<220> FEATURE:
<223> OTHER INFORMATION: ROC domain peptide
<220> FEATURE:
<221> NAME/KEY: MISC_FEATURE
<222> LOCATION: (16)..(16)
<223> OTHER INFORMATION: Xaa is (S)-2-(4'-pentenyl)alanine
<220> FEATURE:
<221> NAME/KEY: MISC_FEATURE
<222> LOCATION: (20)..(20)
<223> OTHER INFORMATION: Xaa is (S)-2-(4'-pentenyl)alanine

<400> SEQUENCE: 13

Asp Glu Lys Gln Arg Lys Ala Cys Met Ser Lys Ile Thr Lys Glu Xaa
1               5                   10                  15

Leu Asn Lys Xaa
            20

<210> SEQ ID NO 14
<211> LENGTH: 12
<212> TYPE: PRT
<213> ORGANISM: Artificial Sequence
<220> FEATURE:
<223> OTHER INFORMATION: COR domain peptide

<400> SEQUENCE: 14

Lys Gly Glu Gly Glu Thr Leu Leu Lys Lys Trp Lys
1               5                   10

<210> SEQ ID NO 15
<211> LENGTH: 9
<212> TYPE: PRT
<213> ORGANISM: Artificial Sequence
<220> FEATURE:
<223> OTHER INFORMATION: COR domain peptide

<400> SEQUENCE: 15

Gly Glu Gly Glu Thr Leu Leu Lys Lys
1               5
```

```
<210> SEQ ID NO 16
<211> LENGTH: 12
<212> TYPE: PRT
<213> ORGANISM: Artificial Sequence
<220> FEATURE:
<223> OTHER INFORMATION: COR domain peptide
<220> FEATURE:
<221> NAME/KEY: MISC_FEATURE
<222> LOCATION: (6)..(6)
<223> OTHER INFORMATION: Xaa is (S)-2-(4'-pentenyl)alanine
<220> FEATURE:
<221> NAME/KEY: MISC_FEATURE
<222> LOCATION: (10)..(10)
<223> OTHER INFORMATION: Xaa is (S)-2-(4'-pentenyl)alanine

<400> SEQUENCE: 16

Lys Gly Glu Gly Glu Xaa Leu Leu Lys Xaa Trp Lys
1               5                   10

<210> SEQ ID NO 17
<211> LENGTH: 9
<212> TYPE: PRT
<213> ORGANISM: Artificial Sequence
<220> FEATURE:
<223> OTHER INFORMATION: COR domain peptide
<220> FEATURE:
<221> NAME/KEY: MISC_FEATURE
<222> LOCATION: (1)..(1)
<223> OTHER INFORMATION: Xaa is (S)-2-(4'-pentenyl)alanine
<220> FEATURE:
<221> NAME/KEY: MISC_FEATURE
<222> LOCATION: (5)..(5)
<223> OTHER INFORMATION: Xaa is (S)-2-(4'-pentenyl)alanine

<400> SEQUENCE: 17

Xaa Glu Gly Glu Xaa Leu Leu Lys Lys
1               5

<210> SEQ ID NO 18
<211> LENGTH: 9
<212> TYPE: PRT
<213> ORGANISM: Artificial Sequence
<220> FEATURE:
<223> OTHER INFORMATION: COR domain peptide
<220> FEATURE:
<221> NAME/KEY: MISC_FEATURE
<222> LOCATION: (4)..(4)
<223> OTHER INFORMATION: Xaa is (S)-2-(4'-pentenyl)alanine
<220> FEATURE:
<221> NAME/KEY: MISC_FEATURE
<222> LOCATION: (8)..(8)
<223> OTHER INFORMATION: Xaa is (S)-2-(4'-pentenyl)alanine

<400> SEQUENCE: 18

Gly Glu Gly Xaa Thr Leu Leu Xaa Lys
1               5

<210> SEQ ID NO 19
<211> LENGTH: 9
<212> TYPE: PRT
<213> ORGANISM: Artificial Sequence
<220> FEATURE:
<223> OTHER INFORMATION: COR domain peptide
<220> FEATURE:
<221> NAME/KEY: MISC_FEATURE
<222> LOCATION: (5)..(5)
<223> OTHER INFORMATION: Xaa is (S)-2-(4'-pentenyl)alanine
<220> FEATURE:
<221> NAME/KEY: MISC_FEATURE
<222> LOCATION: (9)..(9)
<223> OTHER INFORMATION: Xaa is (S)-2-(4'-pentenyl)alanine
```

```
<400> SEQUENCE: 19

Gly Glu Gly Glu Xaa Leu Leu Lys Xaa
1               5

<210> SEQ ID NO 20
<211> LENGTH: 10
<212> TYPE: PRT
<213> ORGANISM: Artificial Sequence
<220> FEATURE:
<223> OTHER INFORMATION: COR domain peptide

<400> SEQUENCE: 20

Gly Glu Gly Glu Thr Leu Leu Lys Lys Trp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: COR domain peptide
<220> FEATURE:
<221> NAME/KEY: MISC_FEATURE
<222> LOCATION: (6)..(6)
<223> OTHER INFORMATION: Xaa is (S)-2-(4'-pentenyl)alanine
<220> FEATURE:
<221> NAME/KEY: MISC_FEATURE
<222> LOCATION: (10)..(10)
<223> OTHER INFORMATION: Xaa is (S)-2-(4'-pentenyl)alanine

<400> SEQUENCE: 21

Lys Gly Glu Gly Glu Xaa Leu Leu Lys Xaa Trp Lys
1               5                   10

<210> SEQ ID NO 22
<211> LENGTH: 20
<212> TYPE: PRT
<213> ORGANISM: Artificial Sequence
<220> FEATURE:
<223> OTHER INFORMATION: LRIP4 scramble
<220> FEATURE:
<221> NAME/KEY: MISC_FEATURE
<222> LOCATION: (2)..(2)
<223> OTHER INFORMATION: Xaa is norleucine
<220> FEATURE:
<221> NAME/KEY: MISC_FEATURE
<222> LOCATION: (16)..(16)
<223> OTHER INFORMATION: Xaa is (S)-2-(4'-pentenyl)alanine
<220> FEATURE:
<221> NAME/KEY: MISC_FEATURE
<222> LOCATION: (20)..(20)
<223> OTHER INFORMATION: Xaa is (S)-2-(4'-pentenyl)alanine

<400> SEQUENCE: 22

Gln Xaa Asp Lys Ala Glu Ser Lys Asn Lys Glu Arg Lys Leu Cys Xaa
1               5                   10                  15

Thr Ile Lys Xaa
            20

<210> SEQ ID NO 23
<211> LENGTH: 12
<212> TYPE: PRT
<213> ORGANISM: Artificial Sequence
<220> FEATURE:
<223> OTHER INFORMATION: LCIP scramble
<220> FEATURE:
<221> NAME/KEY: MISC_FEATURE
<222> LOCATION: (6)..(6)
<223> OTHER INFORMATION: Xaa is (S)-2-(4'-pentenyl)alanine
```

-continued

```
<220> FEATURE:
<221> NAME/KEY: MISC_FEATURE
<222> LOCATION: (10)..(10)
<223> OTHER INFORMATION: Xaa is (S)-2-(4'-pentenyl)alanine

<400> SEQUENCE: 23

Gly Lys Trp Glu Lys Xaa Gly Glu Leu Xaa Lys Leu
1               5                   10

<210> SEQ ID NO 24
<211> LENGTH: 19
<212> TYPE: PRT
<213> ORGANISM: Artificial Sequence
<220> FEATURE:
<223> OTHER INFORMATION: hs_LRRK1 ROC

<400> SEQUENCE: 24

Glu Ala Lys Phe Arg Val Glu Arg Ile Ala Thr Leu Arg Ala Tyr Val
1               5                   10                  15

Leu Ala Leu

<210> SEQ ID NO 25
<211> LENGTH: 19
<212> TYPE: PRT
<213> ORGANISM: Artificial Sequence
<220> FEATURE:
<223> OTHER INFORMATION: hs_MFHSA1 ROC

<400> SEQUENCE: 25

Gly Glu Arg Glu Leu Glu Glu Lys Cys Leu Asp Ile His Arg Gln Ile
1               5                   10                  15

Ala Leu Gln

<210> SEQ ID NO 26
<211> LENGTH: 19
<212> TYPE: PRT
<213> ORGANISM: Artificial Sequence
<220> FEATURE:
<223> OTHER INFORMATION: hs_DAPK1 ROC

<400> SEQUENCE: 26

Gly Gly Glu Phe Gly Tyr Asp Lys Asp Thr Ser Leu Leu Lys Glu Ile
1               5                   10                  15

Arg Asn Arg

<210> SEQ ID NO 27
<211> LENGTH: 18
<212> TYPE: PRT
<213> ORGANISM: Artificial Sequence
<220> FEATURE:
<223> OTHER INFORMATION: dicty_ROCO4 ROC

<400> SEQUENCE: 27

Thr Pro Glu Gln Leu Gln Glu Ala Glu Ser Ile Leu Lys Ala Asn Phe
1               5                   10                  15

Val Lys

<210> SEQ ID NO 28
<211> LENGTH: 14
<212> TYPE: PRT
<213> ORGANISM: Artificial Sequence
<220> FEATURE:
<223> OTHER INFORMATION: CT_Roco ROC

<400> SEQUENCE: 28
```

-continued

```
Pro Ser Tyr Asn Ile Glu Gln Lys Lys Ile Asn Glu Arg Phe
1               5               10

<210> SEQ ID NO 29
<211> LENGTH: 10
<212> TYPE: PRT
<213> ORGANISM: Artificial Sequence
<220> FEATURE:
<223> OTHER INFORMATION: hs_LRRK1 COR

<400> SEQUENCE: 29

Ser Asp Gly Thr Pro Leu Met Glu Gln Tyr
1               5               10

<210> SEQ ID NO 30
<211> LENGTH: 11
<212> TYPE: PRT
<213> ORGANISM: Artificial Sequence
<220> FEATURE:
<223> OTHER INFORMATION: dicty_ROCO4 COR

<400> SEQUENCE: 30

Phe Ser Ser Cys Ile Ala Ser Ala Leu Gln Asp
1               5               10

<210> SEQ ID NO 31
<211> LENGTH: 10
<212> TYPE: PRT
<213> ORGANISM: Artificial Sequence
<220> FEATURE:
<223> OTHER INFORMATION: Ct_Roco COR

<400> SEQUENCE: 31

Tyr Lys Glu Leu Leu Gly Leu Glu Lys Met
1               5               10

<210> SEQ ID NO 32
<211> LENGTH: 20
<212> TYPE: PRT
<213> ORGANISM: Artificial Sequence
<220> FEATURE:
<223> OTHER INFORMATION: Native ROC peptide
<220> FEATURE:
<221> NAME/KEY: MISC_FEATURE
<222> LOCATION: (9)..(9)
<223> OTHER INFORMATION: Xaa is norleucine

<400> SEQUENCE: 32

Asp Glu Lys Gln Arg Lys Ala Cys Xaa Ser Lys Ile Thr Lys Glu Leu
1               5               10                  15

Leu Asn Lys Arg
            20
```

CHEMICALLY-STABILIZED ALLOSTERIC MODULATORS OF LEUCINE-RICH REPEAT KINASE 2 (LRRK2)

CROSS-REFERENCE TO RELATED APPLICATIONS

This application claims the benefit of priority to U.S. Provisional Application No. 62/981,276, filed Feb. 25, 2020, and European Patent Application No. 20170251.1, filed Apr. 17, 2020, the disclosures of which are incorporated herein by reference in their entirety.

INCORPORATION BY REFERENCE OF SEQUENCE LISTING PROVIDED AS A TEXT FILE

A Sequence Listing is provided herewith as a text file entitled "10067_063US1_SequenceListing_ST25.txt" created Mar. 28, 2022, and having a size of 11,856 bytes. The contents of the text file are incorporated by reference herein in their entirety.

TECHNICAL FIELD

This disclosure relates to stapled polypeptides, and more particularly to stapled polypeptides that inhibit or modulate the activity of leucine-rich repeat kinase 2 (LRRK2).

BACKGROUND

Parkinson's disease (PD) is a relatively common age-related neurodegenerative disorder resulting from the progressive loss of dopamine-producing neurons and which affects up to 4% of the population over age 80. PD is characterized by both motor symptoms, such as tremor at rest, rigidity, akinesia and postural instability as well as non-motor symptoms such as impairment of cognition, sleep and sense of smell. Genome-wide association (GWA) studies have linked LRRK2 to PD and many patients with point mutations in LRRK2 present symptoms that are indistinguishable from those with idiopathic PD. Furthermore, recent GWA studies have implicated LRRK2 in the pathogenesis of various other human diseases such as inflammatory bowel disease (Crohn's disease), cancer and leprosy (see Lewis, P. A., et al. Science Signaling 2012, 5(207):e2). LRRK2 is a large multi-domain protein (~280 kD) that belongs to the Roco family of proteins. The catalytic core region of LRRK2 consists of a Ras-of-complex proteins (Roc) G-domain, a C-terminal-of-Roc (COR) dimerization domain, and a kinase domain. This region is flanked by protein interaction domains: armadillo repeats (ARM), ankyrin repeats (ANK) and leucine-rich repeats (LRR) at the N-terminus, and a WD40 repeat domain at the C-terminus. Over 20 LRRK2 mutations have been associated with auto-somal-dominant Parkinsonism, and the R1441C, R1441G, R1441H, Y1699C, G2019S, I2020T and N1437H missense mutations are considered to be pathogenic. Several of the PD-mutations have been linked to a decrease in GTPase and/or an increase in kinase activity. Therefore, both academics and industry have developed several ATP competitive kinase inhibitors that are brain penetrant and selective for LRRK2; however, long-term inhibition of LRRK2 by these inhibitors leads to kidney abnormalities in rodent and an accumulation of lamellar bodies in the lungs of non-human primate (see Ness, D. et al. Leucine-rich repeat kinase 2 (LRRK2)-deficient rats exhibit tubule injury and perturbations in metabolic and immunological homeostasis. PLoS One 8, e66164 (2013); Herzig, M. C. et al. LRRK2 protein levels are determined by kinase function and are crucial for kidney and lung homeostasis in mice. Hum. Mol. Genet. 20, 4209-23 (2011); Tong, Y. et al. Loss of leucine-rich repeat kinase 2 causes age dependent bi-phasic alterations of the autophagy pathway. Mol. Neurodegener. 7, 2 (2012)). On a cellular level it has been shown that all so far characterized ATP-competitive LRRK2 inhibitors induce accumulation of LRRK2 into filament structures bound to microtubules (see Ramirez, M. B. et al. GTP binding regulates cellular localization in Parkinson's disease-associated LRRK2. Hum. Mol. Genet. 26, 2747-2767 (2017); Dzamko, N. et al. Inhibition of LRRK2 kinase activity leads to dephosphorylation of Ser(910)/Ser(935), disruption of 14-3-3 binding and altered cytoplasmic localization Biochem. J. 430, 405-413 (2010); and Kett L. R. et al. LRRK2 Parkinson disease mutations enhances its microtubule association. Hum. Mol. Genet. 21, 890-899 (2012)). Furthermore, these LRRK2 filaments disturb vesicular membrane transport along the microtubules (see Deniston, C. K. et al. (2020) Parkinson's Disease-linked LRRK2 structure and model for microtubule interaction. Nature 2020, 588(7837):344-349). Therefore, alternative approaches that target other domains and functions of LRRK2 may have significantly improved therapeutic benefits.

LRRK2 can exist as a monomer in the cytosol and as an active kinase dimer/oligomer at the membrane (Webber, P. J. et al. Autophosphorylation in the leucine-rich repeat kinase 2 (LRRK2) GTPase domain modifies kinase and GTP-binding activity. J. Mol. Biol. 412, 94-110 (2011); Greggio, E. et al. The Parkinson disease-associated leucine-rich repeat kinase 2 (LRRK2) is a dimer that undergoes intra-molecular autophosphorylation. J. Biol. Chem. 283, 16906-14 (2008); Berger, X. et al. Membrane localization of LRRK2 is associated with increased formation of the highly active LRRK2 dimer and changes in its phosphorylation. Biochemistry 49, 5511-5523). GTP-bound monomeric LRRK2 is uniformly distributed in the cytosol. A state that is stabilized by 14-3-3 proteins which bind to LRRK2 upon phosphorylation of its N-terminally located serine residues and prevent LRRK2 aggregation in cytosolic inclusion pools (see Li, X. et al. Phosphorylation-Dependent 14-3-3 Binding to LRRK2 Is Impaired by Common Mutations of Familial Parkinson's Disease. PLoS One 6, 1-13 (2011); Nichols, R. J. et al. 14-3-3 binding to LRRK2 is disrupted by multiple Parkinson's disease-associated mutations and regulations cytoplasmic localization. Biochem. J. 430, 393-404 (2010); and Rudenko, I. N. et al. 14-3-3-proteins are promising LRRK2 interactors. Biochem. J. 430, e5-6 (2010)). In this stabilized monomeric state, both the GTPase and kinase presumably have only low basal activity (Berger, Z. et al. Membrane localization of the highly active LRRK2 dimer and changes in its phosphorylation. Biochemistry 49, 5511-5523 (2010)). GTP-bound Rab proteins, recruit GTP-bound LRRK2 to the membrane, by binding to the N-terminus of LRRK2. This recruitment has, for example, been demonstrated for Rab29, which binds the Ankyrin domain of LRRK2 and in this way recruits the protein to the Golgi apparatus (Purlyte, E. et al. Rab29 activation of the Parkinson's disease-associated LRRK2 kinase. EMBO J. e201798099 (2017). Doi:10.15252/embj.201798099). At the membrane LRRK2 goes through a multi-step hydrolysis cycle, resulting in a dimeric, GDP-bound conformation of LRRK2 at the membrane. It is unclear during which step dimerization occurs; however it is mediated via the RocCOR domain and is crucial for hydrolysis, maximum kinase activity and LRRK2 functioning. Moreover, mutations analogous to PD-linked mutations decrease the GTPase and increase the kinase activity by interfering with this dimer-monomer cycle (Leandrou et al. 2019).

Stapled peptides are conformationally locked using peptide "stapling" to stabilize and constrain an alpha-helical structure (see Verdine, G. L. et al. Methods Enzymol. 2012, 503:3-33). Stabilization of the secondary structure introduces an entropically favorable pre-ordered binding state where key interacting residues are spatially poised for target binding while deeming the peptide product cell permeable and therefore do not require transfections or other methods such as conjugation to the cell-penetrating peptide TAT or aliphatic anchors for delivery (see Verdine et al.; and Kutchukian, P. S. et al. J. Am. Chem. Soc. 2009, 131:4622-4627). Further, these compounds can be synthetically designed to incorporate affinity or imaging moieties such as biotin or fluorophores to aid in cell localization and interaction experiments. Stapled peptides target protein-protein interaction (PPI) interfaces by providing an elongated binding surface that can bind to shallow protein pockets and surfaces. Therefore, stapled peptides can target proteins that may otherwise not be amenable using a small molecule approach which often requires a reasonably well-defined deep binding pocket.

There is a clear need for therapeutics that inhibit or modulate the activity of LRRK2 in vivo for the treatment of neurological diseases or disorders.

SUMMARY

Provided herein are synthetic stapled polypeptides that inhibit or modulate the activity of leucine-rich repeat kinase 2 (LRRK2) which are useful in the treatment of neurological diseases, disorders or conditions. Methods of treatment for such conditions with the disclosed polypeptides are also provided. The presently disclosed synthetic stapled peptides mimic either the ROC domain or the COR domain that is involved in homodimerization of LRRK2 and subsequently downregulate LRRK2 kinase activity. These compounds also different from other catalytic inhibitors of LRRK2 because they do not alter LRRK2 localization in cells, an effect that has been associated with subsequent toxicity. Indeed, the stapled polypeptides described herein modulate LRRK2 kinase activity without affecting its subcellular localization. Cytosolic LRRK2 protein localization has been observed to be disturbed and redirected to the microtubules for all so far characterized Type I kinase ATP-competitive inhibitors of LRRK2. The differentiating potential in therapeutic approaches of the LRRK2 allosteric modulators of the present disclosure is therefore expected to emerge from its more precise and/or highly specific effect on LRRK2 activity without further disturbing vesicular membrane transport or other downstream effects caused by relocalized LRRK2 bound to microtubules.

Thus in one aspect, a synthetic polypeptide is provided comprising an amino acid sequence having an α-helical shape that mimics the Ras of complex proteins (ROC) domain of LRRK2, wherein the polypeptide comprises at least one pair of non-natural amino acids inserted into the amino acid sequence that are cross-linked to stabilize the α-helical shape. In some embodiments, the polypeptide comprises a variant of the amino acid sequence of SEQ ID NO. 1 or SEQ ID NO. 2, wherein the variant comprises at least one pair of amino acids that are cross-linked to stabilize the α-helical shape. In some embodiments, the polypeptide is formed from a peptide comprising an amino acid sequence selected from SEQ ID NO. 3 to 11.

In another aspect, a synthetic polypeptide is provided comprising an amino acid sequence that mimics the C-terminal of ROC (COR) domain of LRRK2, wherein the polypeptide comprises at least one pair of non-natural amino acids inserted into the amino acid sequence that are cross-linked to stabilize the α-helical shape. In some embodiments, the polypeptide comprises a variant of SEQ ID NO. 14 or SEQ ID NO. 15, wherein the variant comprises at least one pair of amino acids that are cross-linked to stabilize the α-helical shape. In some embodiments, the polypeptide is formed form a peptide comprising an amino acid sequence selected from SEQ ID NO. 16 to 19.

In other aspects, method of treating a neurological disease, disorder, or condition in a subject in need thereof are provided comprising administering a therapeutically effective amount of a polypeptide desired herein. In some embodiments, the neurological disease, disorder, or condition may include Parkinson's disease, Huntington's disease, Alzheimer's disease, or amyotrophic lateral sclerosis (ALS). In other aspects, a method of treating Crohn's disease in a subject in need thereof is provided comprising administering a therapeutically effective amount of the polypeptide described herein.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIGS. 1A-ID show the design and synthesis of stapled peptide dimerization disruptors of LRRK2. FIG. 1A shows the domain architecture of LRRK2 and a homology model of the RocCOR dimer interface. FIG. 1B shows sequence alignments of LRRK2 to other Roco proteins at the indicated interfaces. FIG. 1C shows that peptide library sequences were designed to preserve amino acids at the predicted interface. Non-natural amino acids were substituted on the predicted non-binding interface.

In FIG. 2A, that fluorescence polarization assays indicated that while LRIP4 bound its RocCOR target with a $K_D$ of approximately 50 nM, LCIP1 bound its CORB target with considerably less affinity with a $K_D$ of 1 μM. Both scrambled peptide controls exhibited no binding. Each data point is representative of n=3. In FIG. 2B, shows that lysates derived from HEK293 cells overexpressing GFP-tagged LRRK2 were treated with 10 μM biotin-labeled peptides (LCIP1 and LRIP4) and pulldowns were performed using avidin-coated resin. LRRK2 was detected via immunoblotting, demonstrating that both peptides bound LRRK2. Blot is representative of n=3. In FIG. 2C, HEK293 cells were transiently transfected with Strep-tagged LRRK2 and GFP or GFP-tagged LRRK2. Whereas Strep-LRRK2 did not bind non-specifically to GFP, it was pulled down with GFP-LRRK2. Incubation with inhibitory peptides LRIP4 and LCIP1 resulted in reduced dimerization. GFP alone is indicated in the bottom panel. Blot is representative of n=3.

In FIG. 3A, HEK293 cells were treated with 10 μM FAM-labeled LRIP4 or LCIP1 for 6 hours at 37° C. Flow cytometry experiments demonstrate that both peptides yielded an increased shift in fluorescence. In FIG. 3B, confocal fluorescence microscopy images indicate that LRIP4 and LCIP1 can be detected in the cytosol with LRIP4 demonstrating greater cytosolic accumulation. Scale bar corresponds to 20 μm. In FIG. 3C, LRRK2 dimerization was measured in cells using a proximity biotinylation ELISA-based assay. Dimeric LRRK2 was biotinylated in situ and purified on streptavidin-coated ELISA plates. LRIP4 was found to inhibit dimerization of both wild-type/G2019S LRRK2 heterodimers or G2019S LRRK2 homodimers in HEK293 cells. *p<0.05 and n=3.

In FIG. 4A, autophosphorylation of LRRK2 (pS1292) was monitored in HEK293 cells in the presence of inhibitor peptides (10 μM) or the ATP-competitive LRRK2 inhibitor MLi-2 (100 nM). HEK293 cells were transiently transfected with GFP-tagged LRRK2 and treated with 10 μM of inhibitor peptides for 12 hours prior to lysis. Both peptides inhibited LRRK2 autophosphorylation as compared to the DMSO control. Blot is representative of n=3. In FIG. 4B, quantification of FIG. 4A by densitometric analysis is shown. Levels of pS1292-LRRK2 were normalized to total LRRK2 expression and shown as LRRK2 activity relative to the DMSO control. Data was averaged from three independent experiments and are shown as means±SD. The inhibitor peptides downregulated autophosphorylation by 50-70% but were not as potent as MLi-2 which demonstrated near complete inhibition. In FIG. 4C, HEK293T cells were transfected with SF-tagged LRRK2 (R1441G) and FLAG-HA-tagged Rab29 and treated with 10 μM of inhibitor peptides for 12 h prior to lysis. Endogenous Rab10 phosphorylation was reduced after treatment with LRIP4 or LCIP1, with LRIP4 having a larger inhibitory effect. Blot is representative of n=3. In FIG. 4D, untransfected A549 cells were used to investigate the inhibitory effect of LRIP4 and LCIP1 (10 μM) on endogenous LRRK2 kinase activity as measured by Rab10 phosphorylation. LRIP4 demonstrated inhibition of Rab10 phosphorylation. Blot is representative of n=3. In FIG. 4E, HEK293 cells were transiently transfected with GFP-tagged LRRK2 and treated with biotin-labeled peptides (10 μM of LRIP4 or LCIP1) for 12 h. As a control, cells were treated with 100 nM MLi-2. Unlike cells treated with MLi-2, LRIP4 and LCIP1 did not induce mislocalization of LRRK2 in cells. Scale bar represents 5 μm. Images are representative of n=3.

In FIG. 5A, reactive oxygen species (ROS) was measured via fluorescence emission of the CellROX deep red dye. RAW 264.7 cells were treated with 10☐M of each peptide for 9 hours then stimulated with Zymosan for 30 mins (50 μg/mL). LRIP1 significantly downregulated ROS production. n=4. In FIG. 5B, cultured primary cortical neurons transiently overexpressing WT or G2019S-LRRK2 were treated with 10 μM of each peptide for 48 h, or 200 nM of MLi-2. Fixed neurons were immunostained for flag-LRRK2 and counterstained with DAPI. Scale bar represents 10 μm. n=3 In FIG. 5C, quantification of apoptotic neurons from FIG. 5B is shown. Neurons from three biological replicates (independent transfections) were counted in a blinded manner. n=3. *p<0.05; p<0.01; *p<0.001.

Like reference symbols in the various drawings indicate like elements.

DETAILED DESCRIPTION

Figure 1D:
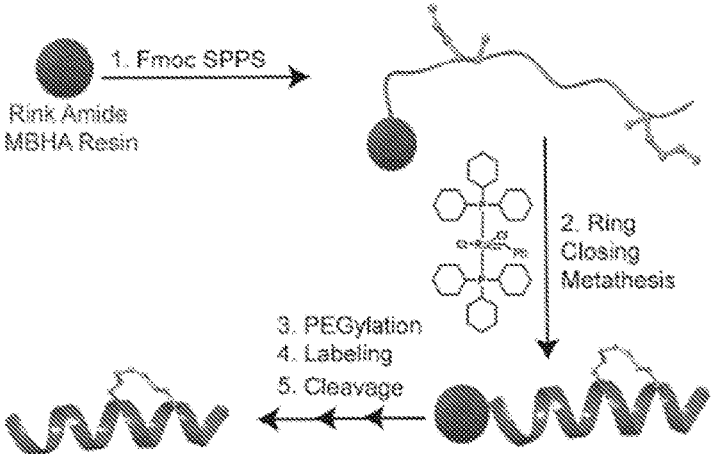
FIG. 1D is a schematic of Fmoc-based Solid Phase Peptide Synthesis (SPPS) and ring-closing metathesis.

The materials, compounds, compositions, and methods described herein may be understood more readily by reference to the following detailed description of specific aspects of the disclosed subject matter and the Figures and Examples included therein.

Before the present materials, compounds, compositions, and methods are disclosed and described, it is to be understood that the aspects described below are not limited to specific synthetic methods or specific reagents, as such may, of course, vary. It is also understood that the terminology used herein is for the purpose of described particular aspects only and is not intended to be limited.

Also, throughout this specification, various publications are reference. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In the specification and in the claims that follow, reference will be made to a number of terms, which shall be defined to have the following meanings:

Through the specification and claims the word "comprise" and other forms of the word, such as "comprising" and "comprises", means including but not limited to, and is not intended to exclude, for example, other additives, components, integers, or steps.

As used in the description and the appended claims, the singular forms "a", "an", and "the" include plural referents unless the context clearly dictates otherwise. Thus, for example, reference to "a composition" includes mixtures of two or more such compositions, and the like.

"Optional" or "optionally" means that the subsequently described event or circumstance can or cannot occur, and that the description includes instances where the event or circumstance occurs and instances where it does not.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in the respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about", it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about".

The term "subject" refers to any individual who is the target of administration or treatment. The subject can be a vertebrate, for example, a mammal. Thus, the subject can be a human or veterinary subject. The term "patient" refers to a subject under the treatment of a clinician, e.g., a physician. The term "patient" preferably to a human in need of treatment with one or more agents or treatments described herein for any purpose. However, the term "patient" can also refer to non-human animals, preferably mammals such as dogs, cats, horses, cows, pig, sheep and non-human primates, among others, that are in need of treatment with an agent or treatment described herein.

By "reduce" or other forms of the word, such as "reducing" or "reduction", is meant lowering of an event or characteristic. It is understood that this is typically in relation to some standard or expected value, in other words it is relative, but that is not always necessary for the standard or relative value to be referred to.

By "prevent" or other forms of the word, such as "preventing" or "preventing", is meant to stop a particular event or characteristic, or to minimize the changes that a particular event or characteristic will occur. Prevent does not require comparison to a control, as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the other word is also expressly disclosed.

As used herein, "treatment" refers to obtaining beneficial or desired clinical results, such as the medical management of a patient with the intent to cure, ameliorate, or stabilize a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; and supportive treatment, that is, treatment employed to supplement another specific therapy directed toward the improvement of the associated disease, pathological condition, or disorder.

"Amino acid" as used herein refers to a molecule containing both an amino group and a carboxyl group. Amino acids include α-amino acids and -amino acids. In certain forms, an amino acid is an alpha amino acid. Amino acids can be natural or synthetic. Amino acids include, but are not limited to, the twenty standard or canonical amino acids: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trk, W), Tyrosine (Tyr, Y), and Valine (Val, V). Common non-standard or non-canonical amino acids include, but are not limited to, selenocysteine, pyrrolysine, and N-formyl-methionine. The term "synthetic amino acid" or "non-natural amino acid" as used herein refers to an organic compound that a structure similar to a natural amino acid so that it mimics the structure and reactivity of a natural amino acid. The synthetic amino acid as defined herein generally increases or enhances the properties of a peptide (e.g., selectivity or stability) when the synthetic amino acid is either substituted for a natural amino acid or incorporated into a peptide.

The terms "peptide", "protein", "polypeptide", or "polyamino acid" are used interchangeably to refer to a natural or synthetic molecule comprising two or more amino acids linked by the carboxyl group of one amino acid to the amino group of another. In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translation processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in the given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleoside or nucleotide derivative, covalent attachment of a lipid or lipid derivative, covalent attachment of a phosphatidylinositol, disulfide bond formation, demethylation, formation of cysteine or pyroglutamate, formylation, gamma-carboxylation, glycosylation, GPI anchor formation, hydroxylating, iodination, methylation, myristoylation, oxidation, PEGylation, proteolytic processing, phosphorylation, prenylation, racemization, selenoylation, sulfation, and transfer-RNA mediated addition of amino acids to proteins such as arginylation. Also included in the term "polypeptides" are cis- and trans-isomers, R- and S-enantiomers, D-isomers, L-isomers, diastereomers, conformers, and mixtures thereof.

The term "residue" as used herein refers to an amino acid that is incorporated into a polypeptide. The amino acid may be a naturally occurring amino acid and, unless otherwise limited, may encompass analogs of natural amino acids that can function in a similar manner as naturally occurring amino acids.

A "variant" as used herein means a polypeptide comprising one or more modifications such as substitutions, deletions, and/or truncations of one or more specific amino acid residues in the corresponding wild-type peptide. A variant of a polypeptide may be naturally occurring or synthetic, and may have 50%, 55%, 60%, 65%, 70%, 75%, 80%, 85%, 90%, 95%, 96%, 97%, 98% or 99% identity with the wild-type polypeptide.

The term "inhibit" refers to a decrease in an activity, response, condition, disease, or other biological parameter. This can include, but is not limited to, the complete ablation of the activity, response, condition, or disease. This may also include, for example, a 10% reduction in the activity, response, condition, or disease as compared to the native or control level. Thus, the reduction can be a 10%, 20%, 30%, 40%, 50%, 60%, 70%, 80% 90%, 100% or any amount of reduction in between as compared to native or control levels.
Stapled Peptides Non-natural, synthetic polypeptides are disclosed that contain a chemically stabilized α-helical shape that mimics domains that facilitate the dimerization of LRRK2, allowing them to bind to LRRK2 in physiological, or supraphysiological, conditions and diminish these interactions that may play a role in various medical disorders or conditions, for example such as Parkinson's disease.

A strategic method to bestow drug-like properties onto α-helical peptides was developed called peptide "stapling" (see Schafmeister C. E., et al. J. Am. Chem. Soc. 2000 122(24):5891-2). This strategy involves the incorporation of two non-natural amino acids within the peptide sequence that are disubstituted to contain α-methyl and α-alkenyl groups. The peptide secondary structure is conformationally locked via, e.g., a Grubbs I catalyzed ring-closing metathesis reaction to form a macrocyclic ring using the α-alkenyl groups (see Mansuy D., et al. Med Sci (Paris). 2005 21(11): 995-6). Further studies have shown that this chemical modification introduces an entropically favorable pre-ordered binding state that increases substrate binding affinity, causes resistance to proteolytic degradation, and greatly enhances cell permeability (see Manschwetus, J. T. et al. Molecules 2019, 24(8):E1567; Flaherty, B. R. et al. ACS Infect Dis 2019, 5(4):506-514; Fulton, M. D. et al. Bioorg Med Chem 2018, 26(6):1167-1173; Teng, Y. et al. Cancer Res 2016, 76(17):5133-42; Wang, Y. et al. ACS Chem Biol 2015, 10(6):1502-10; and Wang, Y. et al. ACS Chem Biol 2014, 9(3):635-642). By applying this chemical modification to a peptide-based scaffold, large binding areas on protein surfaces can be targeted with a high degree of specificity that would otherwise be elusive for targeting using a small molecule approach.

"Peptide stapling" is a term coined from a synthetic methodology wherein two olefin-containing side-chains present in a polypeptide chain are covalently joined (e.g., "stapled together") using a ring-closing metathesis (RCM) reaction to form a cross-linked ring (see, the cover art for J. Org. Chem. 2001 66(16) describing metathesis-based cross-linking of alpha-helical peptides; Blackwell et al. Angew. Chem. Int. Ed. 1994 37:3281). However, the term "peptide stapling" as used herein encompasses the joining of two double bond-containing side chains, two triple bond-containing side chains, or one double bond-containing and one triple bond-containing side chain, which may be present in a polypeptide chain, using any number of reaction conditions and/or catalysts to facilitate such a reaction, to provide a single "staple" polypeptide. Additionally, the term "peptide stitching" as used herein refers to multiple and tandem "stapling" events in a single polypeptide chain to provide a "stitched" (multiply stapled) polypeptide. The disclosed polypeptides can contain a hydrocarbon staple to chemically stabilize an α-helical shape.

In some embodiments, the disclosed peptides include a hydrocarbon staple. The genesis of the hydrocarbon stapling technique can be traced to the ruthenium-based Grubb's catalyst used for ring-closing metathesis. The α-helix features 3.6 residues per complete turn, which places the i, i+4, i+7, and i+11 side chains on the same face of the folded structure. Therefore, stapling cross-links two α,α disubstituted amino acids bearing olefinic chains of variable length at positions "i" and "i+4" or "i+7" in the peptide sequence. In general, the first step in designing stapled peptides for macromolecular targets is the identification of appropriate sites for incorporating the non-natural amino acids used to from the hydrocarbon cross-link. Generally, residues which are not involved in the target recognition are chosen as potential sites for incorporation of olefin-bearing building blocks. These sites are subsequently used to incorporate various suitable stapling systems such as i and i+3; i and i+4; or i and i+7. The classical strategy to stabilize the α-helical conformation in peptides employs covalent bonds between the i and i+3, i and i+4, or i and i+7 side chain groups.

In some embodiments, the polypeptide comprises two non-natural amino acids on the same side of the α-helix that are crosslinked to stabilize the α-helical shape. For example, two non-natural amino acids can be four (i and i+4) or seven (i and i+7) amino acids apart. In some cases, the non-natural amino acids can comprise olefinic side chains, such as: (S)-2-(2'-propenyl)alanine ("S3"); (S)-2-(4'-pentenyl)alanine ("S5"); (S)-2-(5'-hexenyl)alanine ("S6"); (S)-2-(7'-octenyl)alanine ("S8"); (R)-2-(2'-propenyl)alanine ("R3"); (R)-2-(4'-pentenyl)alanine ("R5"); (R)-2-(5'-hexenyl)alanine ("R6"); and (S)-2-(7'-octenyl)alanine ("S8").

The disclosed peptides can be stapled in any suitable pairing, including, but not limited to, a pairing selected from the group consisting of an S5-S5 pairing (i.e., i and i+4), an S5-R8 pairing (i.e., i and i+7), an S8-R5 pairing (i.e., i and i+7), an R3-S6 pairing (i.e., i and i+3), an R6-S3 pairing (i.e., i and i+3), and R3-S5 pairing (i.e., i and i+3), an R5-S3 pairing (i.e., i and i+3), or combinations of pairings within the polypeptide sequence.

The hydrocarbon bridge can then be formed, for example, by a ring-closing metathesis reaction catalyzed by benzylidenebis(tricyclohexyl-phosphine)-dichlororuthenium (Grubb's catalyst). In other embodiments, the ring-closing metathesis reaction can be performed by any other suitable metathesis catalyst as would be available to a person of ordinary skill in the art.

Stapling a peptide using an all-hydrocarbon cross-link has been shown to help maintain its native conformation and/or secondary structure, particularly under physiologically relevant conditions. For example, stapling a polypeptide predisposed to having an α-helical secondary structure can constrain the polypeptide to its native α-helical conformation. The constrained secondary structure may, for example, increase the peptide's resistance to proteolytic cleavage, may increase the peptide's hydrophobicity, may allow for better penetration of the peptide into the target cell's membrane (e.g., through an energy-dependent transport mechanism such a pinocytosis), and/or may lead to an improvement in the peptide's biological activity relative to the corresponding uncrosslinked (e.g., "unstapled") peptide.

A number of alternative stapling methods are known to those in the art, each using a different form of macrocyclization chemistry and giving rise to stapled peptides with different bioactive properties. For example, the stapling may be one-component stapling. One-component stapling involves a direct bond-forming reaction between the side-chains of two amino acids. In some embodiments, the one-component stapling method may comprise formation of an amide bond between two side chains of amino acids in the peptide. In some embodiments, the one-component stapling technique may comprise, for example, a ring-closing metathesis, a lactamization, a cycloaddition (such as the Cu(I)-catalyzed azide-alkyne cycloaddition (CuAAC, "copper-catalyzed click reaction") or ring-strained azide-alkyne cycloaddition), a reversible reaction (such as formation of a disulfide bride or an oxime linkage), or thioether formation. The stapling technique may alternatively be a two-component stapling. Two-component stapling involves a bifunctional linker compound which forms a staple by reacting with two complementary native or non-native amino acids in the peptide of interest. Two-component stapling may employ, for example, a photoswitchable linker or a functionalized "double click" linker. In some embodiments, the precursors may independently comprise residues that are an amino acid analog having an alkyne group on the side chain or an amino acid having an azide group on the side chain, and these groups react with a precursor to the staple having complementary alkyne and/or azide groups to from a triazole. Additional examples of staples and stapling methods appropriate for use in the stapled peptides disclosed herein are described in Walensky, L. D. et al., *J. Med. Chem.* 2014, 57:6275-6288; Lau, Y. H. et al., Chem. Soc. Rev. 2014, 00:1-12; Joy, S. T., et al., Chem. Commun. 52(33):5738-5741; and Zhao, H. et al. Angew. Chem. Int. Ed. 2016, 55:12088-12093, each of which are incorporated herein by reference in their entireties.

Other forms of chemical stabilization may also be used in the disclosed peptides. For example, amino acids, and unstapled, partially stapled, and stapled peptides and proteins, and unstitched, partially stitched, and stitched peptides and proteins may exist in particular geometric or stereoisomeric forms. The disclosed peptides can include all such compounds, including cis- and trans-isomers, R- and S-enantiomers, diastereomers, (D)-isomers, (L)-isomers, racemic mixtures thereof, and other mixtures thereof. Where an isomer-enantiomer is preferred, it may, in some embodiments, be provided substantially free of the corresponding enantiomer, and may also be referred to as "optically enriched". "Optically enriched", as used herein, means that the compound is made up of a significantly greater proportion of one enantiomer. In certain embodiments, the compound of the present invention is made up of at least about 90% by weight of a preferred enantiomer. In other embodiments, the compound is made up of at least about 95%, 98%, or 99% or more by weight of a preferred enantiomer.

The polypeptide can be a synthetic peptide containing non-natural amino acids, or a peptidomimetic. As used herein, "peptidomimetic" means a mimetic of a peptide which includes some alteration of the normal peptide chemistry. Peptidomimetics typically enhance some property of the original peptide, such as increased stability, increased efficacy, enhanced delivery, increased half-life, etc. Use of peptidomimetics can involve the incorporation of a non-amino acid residue with non-amide linkages at a given position. One embodiment of the present invention is a peptidomimetic wherein the compound has a bond, a peptide backbone, or an amino acid component replaced with a suitable mimic. Some non-limiting examples of non-natural amino acids which may be suitable amino acid mimics include, but are not limited to, β-alanine, L-α-aminobutyric acid, L-γ-aminobutyric acid, L-α-aminoisobutyric acid, L-ε- aminocaproic acid, 7-aminoheptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δ-Cbz-L-ornithine, N-δ-Boc-N-α-Cbz-L-orinithine, Boc-p-nitro-L-phenylalanine, Boc-hydroxyproline, and Boc-L-thioproline.

The disclosed peptides may also be substituted with any number of substituents or functional moieties. In general, the term "substituted" refers to the replacement of a hydrogen group in a given structure with a specified substituent group. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example aliphatic, alkyl, alkenyl, alkynyl, heteroaliphatic, heterocyclic, aryl, heteroaryl, acyl, oxo, imino, thioxo, cyano, isocyano, amino, azido, nitro, hydroxyl, thio, halo, etc.), and any combination thereof (for example, aliphatic amino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The disclosed peptides can contain any and all such combinations in order to arrive at a stable substituent/moiety. For the disclosed peptides, heteroatoms such as nitrogen may have hydrogen substituents and/or any suitable substituent as described herein which satisfy the valencies of the heteroatoms and results in the formation of a stable moiety.

Peptides and peptidomimetics can be prepared by any method, such as by synthesizing the peptide or peptidomimetic, or by expressing a nucleic acid encoding an appropriate amino acid sequence in a cell and harvesting the peptide from the cell. Of course, a combination of such methods also can be used.

Examples of chemical synthesis technologies are solid phase synthesis and liquid phase synthesis. Solid phase synthesis methods are largely classified by the tBoc method and the Fmoc method, depending on the type of protective group used. Typically used protective groups include tBoc (t-butoxycarbonyl), Cl—Z (2-chlorobenzyloxycarbonl), Br—Z (2-bromobenzyloxycarbonyl), Bzl (benzyl), Fmoc (9-fluorenylmethoxycarbonyl), Mbh (4,4'-dimethoxydibenzyhydryl), Mtr (4-methoxy-2,3,6-trimethylbenzenesulfonyl), Trt (trityl), Tos (tosyl), Z (Benzyloxycarbonyl), and Clz-Bzl (2,6-dichlrobenzyl) for the amino groups; NO2 (nitro) and Pmc (2,2,5,7,8-pentamethylchromane-6-sulfonyl) for the guanidino groups; and t-Bu (t-butyl) for the hydroxyl groups. After synthesis of the desired peptide, it is subjected to one or more deprotection reactions and cut out from the solid support. Such peptide cutting reactions may be carried out with hydrogen fluoride or trifluoromethane sulfonic acid for the Boc method, or with TFA for the Fmoc method. Methods of de novo synthesizing of peptides and peptidomimetics are described, for example, in Chan et al., Fmoc Solid Phase Peptide Synthesis, Oxford University Press, Oxford, United Kingdom, 2005; and Peptide and Protein Drug Analysis, ed. Redi., R., Marcel Dekker, Inc., 2000.

Alternatively, the peptide may be synthesized using recombinant techniques. In this case, a nucleic acid encoding the peptide is cloned into an expression vector under the control of expression control sequences (e.g., a promoter, a terminator and/or an enhancer) allowing its expression. The expression vector is then transfected into a host cell (e.g., a human, CHO, mouse, monkey, fungal or bacterial host cell), and the transfected host cell is cultivated under conditions suitable for the expression of the peptide. Standard recombinant DNA and molecular cloning techniques are described, for example, in: Sambrook and Maniatis, Molecular Cloning: A Laboratory Manual, Second Edition, Cold Spring Harbor Laboratory Press, Cold Spring Harbor, N.Y. (1989); Silhavy et al., Experiments with Gene Fusions, Cold Spring Harbor Laboratory Press, Cold Spring Harbor, N.Y. (1984); and Ausubel et al., Current Protocols in Molecular Biology, published by Greene Publishing Assoc. and Wiley-Interscience (1987).

The method of producing the peptide may optionally comprise the steps of purifying said peptide, chemically modifying said peptide, and/or formulating said peptide into a pharmaceutical composition.

In some embodiments, the stapled peptide includes a helical motif (i.e., a stapled helical peptide). Different amino acid residues have different propensities for forming different secondary structures. For example, methionine (M), alanine (A), leucine (L), glutamate (E), and lysine (K) all have especially high α-helix forming propensities. Thus in some embodiments, the stapled polypeptide includes one or more amino acid residues selected from methionine (M), alanine (A), leucine (L), glutamate (E), and lysine (K). In contrast, proline (P) and glycine (G) are α-helix disruptors. Thus in some embodiments, the stapled polypeptide does not include one or more proline (P) and glycine (G) amino acid residues.

In some embodiments, stapled peptides that target interactions between the Ras of complex proteins (ROC) G-domain and the C-terminal of Roc (COR) domains of LRRK2 are provided. These domains are shown to be involved in homodimerization of LRRK2.

Non-natural synthetic polypeptides are disclosed that contain a chemically stabilized α-helical shape that mimics the interface between the ROC domain and the COR domain of LRRK2 during homodimerization, allowing them to bind to an endogenous ROC domain or COR domain of LRRKS in physiological, or supraphysiological, conditions and to inhibit homodimerization of LRRK2.

In some embodiments, the polypeptide mimics the ROC domain of LRRK2, for example the residues 1459-1473 of LRRK2 (UniProtKB—Q5S007). In some embodiments, the polypeptide mimics the α-helix forming peptide having the sequence: DEKQRKACMSKITKELLNKR (SEQ ID NO. 1). In some embodiments, the polypeptide mimics the α-helix forming peptide having the sequence: EKQRKACMSKITKEL (SEQ ID NO. 2) For example, the polypeptide can comprise a variant of the amino acid sequence SEQ ID NO. 1 or SEQ ID NO. 2, wherein the variant comprises a pair of olefin-terminated, non-natural amino acids (for example selected from (S)-2-(4'-pentenyl) alanine, (R)-2-(4'-pentenyl)alanine, (S)-2-(7'-octenyl)alanine, (R)-2-(7'-octenyl)alanine, or variants thereof) that form a hydrocarbon staple to stabilize the α-helical shape. For example, the polypeptide can be formed from a peptide comprising an amino acid sequence selected from the sequences provided in Table 1 below:

TABLE 1

| ROC Domain LRRK2 Stapled Peptide Precursors | |
| --- | --- |
| Sequence | |
| DEKXRKAX(Nle)SKITKELLNKR | SEQ ID NO. 3 |
| DEKQRKAX(Nle)SKXTKELLNKR | SEQ ID NO. 4 |
| DEKQRKAC(Nle)SKXTKEXLNKR | SEQ ID NO. 5 |
| DEKQRKAC(Nle)SKITKEXLNKX | SEQ ID NO. 6 |
| EKXRKAXMSKITKEL | SEQ ID NO. 7 |
| EKQXKACXSKITKEL | SEQ ID NO. 8 |
| EKQRKAXMSKXTKEL | SEQ ID NO. 9 |
| EKQRKACXSKIXKEL | SEQ ID NO. 10 |
| EKQRKACMSKXTKEX | SEQ ID NO. 11 | wherein Nle is norleucine and X is (S)-2-(4'-pentenyl) alanine.

Representative examples of stapled peptides derived from the ROC domain of LRRK2 include:

(I-a)

(I-b)

(I-c)

and (I-d)

wherein:

$R^A$ is —$CH_3$ or a substituted or unsubstituted derivative thereof, $R^C$ is —$CH_2$—SH or a substituted or unsubstituted derivative thereof;

$R^D$ is —$CH_2$—COOH or a substituted or unsubstituted derivative thereof;

$R^E$ is —$(CH_2)_2$—COOH or a substituted or unsubstituted derivative thereof;

$R^I$ is —$CH(CH_3)$—$CH_2$—$CH_3$ or a substituted or unsubstituted derivative thereof, $R^K$ is —$(CH_2)_4$—$NH_2$ or a substituted or unsubstituted derivative thereof, $R^L$ is —$CH_2$—$CH(CH_3)_2$ or a substituted or unsubstituted derivative thereof, $R^N$ is —$CH_2$—$CONH_2$ or a substituted or unsubstituted derivative thereof, $R^{NL}$ is —$(CH_2)_3$—$CH_3$ or a substituted or unsubstituted derivative thereof;

$R^Q$ is —$(CH_2)_2$—$CONH_2$ or a substituted or unsubstituted derivative thereof;

$R^R$ is —$(CH_2)_3$—NH—(C=NH)—$NH_2$ or a substituted or unsubstituted derivative thereof, $R^S$ is —$CH_2$—OH or a substituted or unsubstituted derivative thereof; and $R^T$ is —$CH(OH)$—$CH_3$ or a substituted or unsubstituted derivative thereof.

Further representative examples of stapled peptides derived from the ROC domain of LRRK2 include:

(II-a)

(II-b)

(II-c)

-continued (II-d)

(II-e)

wherein: $R^M$ is —$(CH_2)_2$—S—$CH_3$ or a substituted or unsubstituted derivative thereof, and all other variables are as defined herein.

In some embodiments, the polypeptide mimics the α-helix forming peptide having the sequence: DEKQRKACMSKITKELLNK (SEQ ID NO. 12). In some embodiments, the polypeptide can be formed from a peptide comprising the amino acid sequence: DEKQRKACMSKITKEXLNKX (SEQ ID NO. 13), wherein X is (S)-2-(4'-pentenyl)alanine.

In some embodiments, the polypeptide mimics the COR domain of LRRK2, for example the residues 1802-1810 of LRRK2 (UniProtKB—Q5S007). In some embodiments, the polypeptide mimics the α-helix forming peptide having the sequence: KGEGETLLKKWK (SEQ ID NO. 14). In some embodiments, the polypeptide mimics the α-helix forming peptide having the sequence GEGETLLKK (SEQ ID NO. 15). For example, the polypeptide can comprise a variant of the amino acid sequence SEQ ID NO. 14 or SEQ ID NO. 15, wherein the variant comprises a pair of olefin-terminated, non-natural amino acids (for example selected from (S)-2-

(4'-pentenyl)alanine, (R)-2-(4'-pentenyl)alanine, (S)-2-(7'-octenyl)alanine, (R)-2-(7'-octenyl)alanine, or variants thereof) that form a hydrocarbon staple to stabilize the α-helical shape. For example, the polypeptide can be formed from a peptide comprising an amino acid sequence selected from the sequences provided in Table 2 below:

TABLE 2

| COR Domain LRRK2 Stapled Peptide Precursors | |
| --- | --- |
| Sequence | |
| KGEGEXLLKXWK | SEQ ID NO. 16 |
| XEGEXLLKK | SEQ ID NO. 17 |
| GEGXTLLXK | SEQ ID NO. 18 |
| GEGEXLLKX | SEQ ID NO. 19 | wherein X is (S)-2-(4'-pentenyl)alanine.

Representative examples of stapled peptides derived from the COR domain of LRRK2 include:

(III)

(IV-a)

(IV-b)

(IV-c)

wherein:

$R^G$ is hydrogen; and $R^W$ is or a substituted or unsubstituted derivative thereof;

and all other variables are as defined herein.

In some embodiments, the polypeptide mimics the α-helix forming peptide having the sequence: GEGETLLKKW (SEQ ID NO. 20). In some embodiments, the polypeptide can be formed from a peptide comprising the amino acid sequence: KGEGEXLLKXWK (SEQ ID NO. 21), wherein X is (S)-2-(4'-pentenyl)alanine.

In some embodiments, the peptide is about 5 to 100 amino acids in length, including about 5 to 50 amino acids in length. In some embodiments, the peptide is less than 51 amino acids in length, including less than 50, 45, 40, 53, 30, 25, 20, 15, or 10 amino acids in length. Therefore, the provided polypeptide can further constitute a fusion protein or otherwise have additional N-terminal, C-terminal, or intermediate amino acid sequences.

In some embodiments, introduction of a hydrocarbon staple results in poor water solubility and cell permeability. To increase cell permeability and solubility of these peptides, the disclosed polypeptide can be linked to a cell permeability moiety. A "cell permeability" or a "cell-penetration" moiety refers to any molecule known in the art which is able to facilitate or enhance penetration of molecules through membranes. Non-limiting examples include: hydrophobic moieties such as lipids, fatty acids, steroids, and bulky aromatic or aliphatic compounds; moieties which may cell-membrane receptors or carriers, such a steroids, vitamins and sugars, natural and non-natural amino acids and transporter peptides. Examples for lipidic moieties which may be used according to the present invention include: Lipofectamine, TransfectACE, Trasfectam, Cytofectic, DMRIE, DLRIE, GAP-DLRIE, DOTAP, DOPE, DMEAP, DODMP, DPOC, DDAB, DOSPA, EDLPC, EDMPC, DPH, TMADPH, CTAB, lysyl-PE, DC-Cho, -alanyl cholesterol, DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethyl ammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, N-succinyldioleoylphosphatidylethanoleamine. 1,2-dioleoyl-sn-glycerol, 1,3-dipalmitoyl-2-succinylglycerol, 1,2-dipalmatoyl-sn-3-succinylglycerol, 1-hexadecyl-2-palmitoylglycerophosphatidylethanolamine, palmitoylhomocysteine, N,N'-bis(dodecylaminocarbonylmethylene)-N,N'-bis(N,N,N-trimethylammoniumethylaminocarbonylmethylene)ethylene diamine tetraiodide; N5,N"-bis(hexadecylaminocarbonylmethylene)-N,N',N"-tris(N,N,N-trimethylammoniumetyhlaminocarbonylmetylene) diethyltriamine hexaiodide; N,N-bis(dodecylaminocarbonylmethylene-N,N-bis(N,N,N-trimethylammoniumethylaminocarbonylmethylene) cyclohexene-1,4-diamine tetraiodide; 1,7,7-tetra(N,N,N,N-tetramethylammoniumethylaminocarbonylmethylene)-3-hexadecylaminocarbonylmethylene-1,3,7-triazaheptane heptaiodide; N5,N5,N',N'-tetra(N,N,-trimethylammonium-ethylaminocarbonylmethylene)-N'-(15,2-dioleoylglycero-3-phosphoethanolaminocarbonylmethylene)diethylene triamine tetraiodide; dioleolylphosphatidyletanolamine; a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6 to 8 carbons in length, a phospholipid with asymmetric acyl chains, 6-(5-cholesten-3b-yloxy)-1-thio-b-D-galactopyranoside, digalactosylglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-α-D-mannopyranoside, 12(((7'-diethylamino-coumarin-3-yl)carbonyl)methylamino)-octadecanoic acid; N-[12-(((7'-diethylaminocoumarin-3-yl)carbonyl)methylamino)octadecanoyl]-2-aminopalmitic acid, (cholesteryl)-4'-trimethylammonio)butanoate; N-succinyldioleoyl-phosphatidylethanoleamine; 1,2-dioleoyl-sn-glycerol; 1'-dipalmitoyl-sn-S-succinyl-glycerol, 1,3-dipalmitoyl-2-succinylglycerol, 1-hexadecyl-2-palmitoylglycero-phosphoethanolamine, and palmitoylhomocysteine.

In some embodiments, the disclosed polypeptide can be linked to a protein transduction domain to effectively enter a cell. The protein transduction domain sequence can be any internalization sequence known or newly discovered in the art, or conservative variants thereof. Non-limiting examples of cellular internalization transporters and sequences include polyarginine (e.g., R), Antennapedia sequences, TAT, HIV-TAT, Pentratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholestero), and BGTG (Bis-Guanidinium-Tren-Cholesterol).

Addition of water soluble polymers or carbohydrates to polypeptide drugs has been shown to prevent their degradation and increase their half-life. For instance, "PEGylation" of polypeptide drugs protects them and improves their pharmacodynamic and pharmacokinetic profiles. The PEGylation process attaches repeating units of polyethylene glycol (PEG) to a polypeptide drug. PEGylation of molecules can lead to increased resistance of drugs to enzymatic degradation, increase half-life in vivo, reduced dosing frequency, decreased immunogenicity, increased physical and thermal stability, increased solubility, increase liquid stability, and reduced aggregation. Therefore, in some embodiments the disclosed polypeptide is covalently linked to a water soluble polymer, such as polyethylene glycol.

The most common route for PEG conjugation of polypeptides has been to activate the PEG with functional groups suitable for reactions with lysine and N-terminal amino acid groups. The monofunctionality of methoxyPET makes it particularly suitable for protein and peptide modification because it yields reactive PEGs that do not produce cross-linked polypeptides, as long as diol PEG has been removed. Branched structures of PEG have also been proven to be useful for PEGylation of a protein or a peptide. For example, a branched PEG attached to a protein has properties of a much larger molecule than a corresponding linear mPEG of the same molecular weight. Branched PEGs also have the advantage of adding two PEG chains per attachment site on the protein, therefore reducing the chance of protein inactivation due to attachment. Furthermore, these structures are more effective in protecting proteins from proteolysis, in reducing antigenicity, and in reducing immunogenicity.

To increase cell permeability and solubility of these peptides, the peptides can be optimized to increase their amphipathic properties. In some cases, an overall net charge (neutral or positive) is needed for permeability. Any method that alters the overall net charge can affect permeability. In some cases, 1, 2, 3, 4, or more hydrophilic residues can be added on the solvent-exposed face of the helix. For example, the hydrophilic residue can be a lysine, aspartic acid, glutamic acid, arginine, histidine, serine, asparagine, or glutamine. In some cases, lysine and/or arginine is used since they have positive charges that help increase permeability. Non-natural amino acids bearing hydrophilic or charged properties can also be added.

Methods of Making

The polypeptides described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups, can be determined by one skilled in the art. The chemistry of protecting groups can be found, for example, in Wuts and Greene, Protective Groups in Organic Synthesis, 4$^{th}$ Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, WI), Acros Organics (Morris Plains, NJ.), Fisher Scientific (Pittsburgh, PA), Sigma (St. Louis, MO), Pfizer (New York, NY), GlaxoSmithKline (Raleigh, NC), Merck (Whitehouse Station, NJ), Johnson & Johnson (New Brunswick, NJ), Aventis (Bridgewater, NJ), AstraZeneca (Wilmington, DE), Novartis (Basel, Switzerland), Wyeth (Madison, NJ), Bristol-Myers-Squibb (New York, NY), Roche (Basel, Switzerland), Lilly (Indianapolis, IN), Abbott (Abbott Park, IL), Schering Plough (Kenilworth, NJ), or Boehringer Ingelheim (Ingelheim, Germany), or are prepared by methods known to those skilled in the art following procedures set forth in the references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry (John Wiley and Sons, 4$^{th}$ Edition); and Larock's Comprehensive Organic Transformations (VCH Publishers Inc., 1989). Other materials, such as the pharmaceutical carriers disclosed herein, can be obtained from commercial sources.

Reactions to produce the compounds described herein can be carried out in solvents, which can be selected by one of skill in the art of organic synthesis. Solvents can be substantially reactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formulation can be monitored by spectroscopic means, such as nuclear magnetic resonance spectroscopy (e.g., $^1$H or $^{13}$C), infrared spectroscopy, spectrophotometry (e.g. UV-visible), or mass spectrometry, or by chromatography such as high-performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chin or racemization of any of the chiral centers contained therein. Suitable protecting groups are 9-fluorenylmethyl-oxycarbonyl (Fmoc), t-butyloxycarbonyl (Boc), benzyloxy-carbonyl (Cbz), biphenylisopropyloxycarbonyl, t-amyloxy-carbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenyl-methyloxycarbonyl (Fmoc) protecting group is particularly preferred for the synthesis of the disclosed compounds. Other preferred side chain protecting groups are: for side chain amino groups like lysine and arginine, 2,2,5,7,8-pentamethylchroman-6-sulfonyl (pmc), nitro, p-toluene-sulfonyl, 4-methoxybenzene-sulfonyl, Cbz, Boc, and ada-mantyloxycarbonyl; for tyrosine, benzyl, o-bromobenzyloxycarbonyl, 2,6-dichlorobenzyl, isopropyl, t-butyl (t-Bu), cyclohexyl, cyclopentyl, and acetyl (Ac); for serine, t-butyl, benzyl, and tetrahydropyranyl; for histidine, trityl, benzyl, Cbz, p-toluenesulfonyl and 2,4-dinitrophenyl; for tryptophan, formyl; for aspartic and glutamic acid, benzyl and t-butyl; and for cysteine, triphenylmethyl (trityl). In solid phase peptide synthesis methods, the α-C-terminal amino acid is attached to a suitable solid support or resin. Suitable solid supports useful for the above synthesis are those materials which are inert to the reagents and reaction of the stepwise condensation-deprotection reactions, as well as being insoluble in the media use. Solid supports for synthesis of α-C-terminal carboxy peptides include 4-hy-droxymethylphenoxymethyl-copoly(styrene-1% divinyl-benzene) or 4-(2',4'-dimethoxyphenyl-Fmoc-aminomethyl) phenoxyacetamidoethyl resin available from Applied Biosystems (Foster City, CA). N,N'-diisopropylcarbodiimide (DIC) or O-benzotriazol-1-yl-N,N,N'N'-tetramethyluronium hexafluorophosphate (HBTU), with or without 4-di-methylaminopyridine (DMAP), 1-hydroxybenzotriazole (HOBt), benzotriazole-1-yloxy-tris(dimethylamino)phosphonium hexafluorophosphate (BOP) or bis(2-oxo-3-oxazolidinyl)phosphine chloride (BOPCl), mediate coupling for from about 0.5 to about 24 hours at a temperature of between 10° C. and 50° C. in a solvent such as dichloromethane, DMF, or NMP. When the solid support is 4-(2',4'-dimethoxy-phenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected (3',4'-dimethoxyphenyl-Fmoc-aminomethyl)phenoxy-acetamidoethyl resin is O-benzotriazol-1-yl-N,N,N',N'-tetramethyluronium hexafluorophosphate (HBTU, 1 equiv.) and 1-hydroxybenzotriazole (HOBt, 1 equiv.) in DMF or O-(1H-6-chlorobenzotriazol-1-yl)-1,1,3, 3,-tetramethyluronium hexafluorophosphate (HCTU, 1 equiv.) and N,N-diisopropylethylamine (DIEA, 1 equiv.) in NMP. The coupling of successive protected amino acids can be carried out in an automatic polypeptide synthesize. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluronium hexafluorophosphate (HBTU, 1 equiv.) and 1-hydroxybenzotriazole (HOBt, 1 equiv.). At the end of the solid phase synthesis, the polypeptide is removed from the resin and deprotected, either successively or in a single operation. Removal of the polypeptide and deprotection can be accomplished in a single operation by treating the resin-bound polypeptide with a cleave reagent comprising thianisole, water, ethanedithiol, and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography or underivatized polystyrene-divinylbenzene (for example, Amberlite XED); silica gel adsorption chromatography; ion exchange chromatography on carboxymethylcellulose; partition chromatography, e.g. on Sephadex G-25, LH-20 or countercurrent distribution; or high performance liquid chromatography (HPLC), especially reverse-phase HPLC on octyl- or octadecylsilyl-silica bonded column packing.

Pharmaceutical Compositions

Also disclosed are pharmaceutical composition comprising any of the polypeptides disclosed herein in a pharmaceutically acceptable carrier. The disclosed polypeptides can be incorporated in the formulations described below as neutral compounds, pharmaceutically acceptable salts, and/or prodrugs thereof. Pharmaceutical formulations can be designed for immediate release, sustained release, delayed release and/or a burst release of one or more of the disclosed polypeptides in a therapeutically effective amount.

The compounds described herein can be formulated for parenteral administration. Parenteral formulations can be prepared as aqueous compositions using techniques known in the art. Typically, such compositions can be prepared as injectable formulations, for example, solutions or suspensions; solid forms suitable for use in preparing solutions or suspensions upon the addition of a reconstitution medium prior to injection; emulsions, such as water-in-oil (w/o)

emulsions, oil-in-water (o/w) emulsions, and microemulsions thereof; liposomes, or emulsomes.

The carrier can be a solvent or dispersion medium containing, for example, water, ethanol, one or more polyols (e.g., glycerol, propylene glycol, and liquid polyethylene glycol), oils such as vegetable oils (e.g., peanut oil, corn oil, sesame oil, etc.) and combinations thereof.

Solutions and dispersions of the polypeptides as neutral compounds or pharmaceutically acceptable salts thereof can be prepared in water or another solvent or dispersion medium suitable mixed with one or more pharmaceutically acceptable excipients including, but not limited to, surfactants, dispersants, emulsifiers, pH modifying agents, or combinations thereof.

Suitable surfactants for use in the disclosed pharmaceutical compositions may be anionic, cationic, amphoteric, or nonionic surface active agents. Suitable anionic surfactants include, but are not limited, to, carboxylate, sulfonate, and sulfate ions. Examples of anionic surfactants include sodium, potassium, and/or ammonium salts of long chain alkyl sulfonates and alkyl aryl sulfonates such as sodium dodecylbenzene sulfonate; dialkyl sodium sulfosuccinates, such as sodium dodecylbenzene sulfonate and sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostereate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer 401, stearoyl monoisopropanolamide, and polyoxyethylene hydrogenated tallow amide. Examples of amphoteric surfactants include sodium N-dodecyl-β-alanine, sodium-N-lauryl-β-iminodipropionate, myristoamphoacetate, lauryl betaine, and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the one or more polypeptides.

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the one or more polypeptides described herein in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required additional ingredients from those listed above. In the case of sterile powders for the preparation of sterile injectable solutions, the preferred methods of preparation are vacuum-drying and freeze-drying techniques which yield a powder of the one or more disclosed polypeptides plus any additional desired ingredient from a previously sterile-filtered solution thereof. The powders can be prepared in such a manner that the particles are porous in nature, which can increase dissolution of the particles. Methods for making porous particles are well known in the art.

The parenteral formulations described herein can be formulated for controlled release including immediate release, delayed release, extended release, pulsatile release, and combinations thereof. For parenteral administration, the polypeptides described herein and optionally one or more additional active agents can be incorporated into microparticles, nanoparticles, or combinations thereof that provide controlled release. For example, the compounds and/or one or more additional active agents can be incorporated into polymeric microparticles which provide controlled release of the polypeptide(s). Release of the polypeptide(s) is controlled by diffusion of the polypeptide(s) out of the microparticles and/or degradation of polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as material for drug-containing microparticles. Other polymers include, but are not limited to, polyanhydrides, poly(ester anhydrides), polyhydroxyacids such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

The polypeptide can also be formulated for depot injection. In a depot injection, the active agent is formulated with one or more pharmaceutically acceptable carriers that provide for the gradual release of the polypeptide over a period of hours or days after injection. The depot formulation can be administered by any suitable means; however, the depot formulation is typically administered via subcutaneous or intramuscular injection. A variety of carriers may be incorporated into the depot to provide for the controlled release of the active agent. In some cases, depot formulations contain one or more biodegradable polymeric or oligomeric carriers. Suitable polymeric carriers include, but are not limited to, poly(lactic acid) (PLA), poly(lactic-co-glycolic acid) (PLGA), poly(lactic acid)-polyethylene glycol (PLA-PEG) block copolymers, polyanhydrides, poly(ester anhydrides), poly(glycolic acid) (PGA), poly-3-hydroxybutyrate (PHB) and copolymers thereof, poly-4-hydroxybutyrate (P4HB) and copolymers thereof, polycaprolactone, cellulose, hydroxypropyl methylcellulose, ethylcellulose, as well as blends, derivatives, copolymers, and combinations thereof. In depot formulations containing a polymeric or oligomeric carrier, the carrier and the polypeptide can be formulated as a solution, an emulsion, or a suspension. One or more polypeptides, and optionally one or more additional active agents, can also be incorporated into polymeric or oligomeric microparticles, nanoparticles, or combinations thereof.

Formulations may also be in the form of an organogel (assuming the polypeptide is relatively water insoluble) or a hydrogel. Numerous gel formulations are known. See, for example, U.S. Pat. No. 5,411,737. Hydrogels, especially those further including nanoparticles or microparticles for sustained, immediate and/or delayed release, can also be used.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

The polypeptides may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the polypeptides alone or in combination with other pharmaceutically acceptable excipients can also be administered. These solutions, particularly those intended for ophthalmic use, may be formulated as 0.01%-10% isotonic solutions, having a pH of about 5-7, with appropriate salts.

Other routes of administration, such as transdermal patches, including iontophoretic and electrophoretic devices, vaginal and rectal administration, are also contemplated herein. Transdermal patches, including iontophoretic and electrophoretic devices, are well known to those of skill in the art. For example, pharmaceutical dosage forms for rectal administration are rectal suppositories, capsules and tablets for systemic effect. Rectal suppositories as used herein mean solid bodies for insertion into the rectum which melt and soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*Theobroma* oil), glycerin-gelatin, carbowax (polyoxyethylene glycol) and appropriate mixtures of mono-, di-, and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 g.

Method of Treatment

The polypeptides described herein can be used to treat or prevent a disease, disorder, or condition in a patient in need thereof. In some embodiments, treatment refers to partial or complete alleviation, amelioration, relief, inhibition, delaying onset, reducing severity, and/or incidence of the disease, disorder, or condition in the patient.

The terms "improve", "increase", "reduce", "decrease", and the like, as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein.

In some embodiments, the patient is an individual who has recently been diagnosed with a disease, disorder, or condition. Typically, early treatment (treatment commencing as soon as possible after diagnosis) is important to minimize the effects of the disease, disorder or condition and to maximize the benefits of treatment.

In some embodiments, the polypeptides described herein can be used to treat or prevent a neurological disease or condition. In some embodiments, the disease, disorder, or condition is a neurodegenerative disease. In some embodiments, the neurological or neurogenerative disease or condition that may be treated includes, for example, Alzheimer's disease, cerebral edema, cerebral ischemia, multiple sclerosis, neuropathies, Parkinson's disease, Huntington's disease, blunt or surgical trauma (including postsurgical cognitive dysfunction and spinal cord or brain stem injury), as well as neurological aspects of disorders such as degenerative disc disease and sciatica.

Further examples of neurodegenerative disorders include, but are not limited to, Alexander's disease, Alper's disease, Alzheimer's disease, amyotrophic lateral sclerosis, ataxia telangiectasia, Batten disease, bovine spongiform encephalopathy, Canavan disease, Cockayne syndrome, corticobasal degeneration, Creutzfeldt-Jakob disease, Huntington's disease, HIV-associated dementia, Kennedy's disease, Krabbe's disease, lewy body dementia, Machado-Joseph disease, multiple sclerosis, multiple system atrophy, narcolepsy, neuroborreliosis, Parkinson's disease, Pelizaeus-Merzbacher disease, Pick's disease, primary lateral sclerosis, prion diseases, Refsum's disease, Sandhoff's disease, Schilder's disease, subacute combined degeneration of spinal cord secondary to pernicious anemia, schizophrenia, spinocerebellar ataxia, spinal muscular atrophy, Steele-Richardson-Olszewski disease, and tabes dorsalis.

In some embodiments, a neurodegenerative disease includes any pathological state involving neuronal degeneration, including Parkinson's disease, Huntington's disease, Alzheimer's disease, and amyotrophic lateral sclerosis. Polyglutamine disease, including Huntington's disease, are neurodegenerative diseases caused by an abnormally expanded polyglutamine tract in the causative gene products.

Thus in one aspect, a method of treating a neurodegenerative disease in a subject is provided, comprising administering to the subject a therapeutically effective amount of a polypeptide described herein. In some embodiments, the subject is an individual suffering from or susceptible to a neurodegenerative disease. In some embodiments, the subject is a human.

In some embodiments, a method of treating Parkinson's disease in a subject is provided comprising administering to the subject a therapeutically effective amount of a polypeptide described herein.

In some embodiments, a method of treating Huntington's disease in a subject is provided comprising administering to the subject a therapeutically effective amount of a polypeptide described herein.

In some embodiments, a method of treating Alzheimer's disease in a subject is provided comprising administering to the subject a therapeutically effective amount of a polypeptide described herein.

In some embodiments, a method of treating amyotrophic lateral sclerosis (ALS) in a subject is provided comprising administering to the subject a therapeutically effective amount of a polypeptide described herein.

In another aspect, a method is provided for treating a disorder or condition that is treated by inhibiting LRRK2 activity in a subject in need thereof, the method comprising administering to the subject a therapeutically effective amount of a polypeptide described herein.

In another aspect, a method is provided for treating or preventing nerve cell degeneration, the method comprising administering to a subject suffering or susceptible to nerve cell degeneration a therapeutically effective amount of a polypeptide described herein.

In particular embodiments, the disorder or condition comprises Parkinson's disease or a Parkinson-plus syndrome. Parkinson-plus syndromes include multiple system atrophy and progressive supranuclear party (PSP). In certain embodiments, the polypeptides described herein are used to treat Parkinson's disease that presents in one or more forms, including, but not limited to sporadic Parkinson's disease, a familial form of Parkinson's disease, autosomal recessive early-onset Parkinson's disease, or post-encephalitic Parkinson's disease. In some embodiments, a therapeutically effective amount of the polypeptides described herein, when administered to a subject having Parkinson's disease or a Parkinson-plus syndrome, ameliorates or lessens the severity of one or more of the symptoms of the disease, including but not limited to tremor, rigidity of the limbs and trunk, akinesia, bradykinesia, and postural abnormalities.

Further provided herein are methods to treat, prevent, delay the onset or progression of, or alleviate the symptoms of a disorder or condition that can be treated by inhibiting or diminishing LRRK2 activity in a subject in need of such treatment, the method comprising administering a therapeutically effective amount of a polypeptide described herein.

The polypeptides provided herein can treat the above-described diseases, disorders, or conditions, for instance, by disrupting native protein-protein interactions with LRRK2. In some particular embodiments, the polypeptides provided herein may prevent dimerization of LRRK2.

In some embodiments, the polypeptides described herein may be used in a method of treating a disorder or condition selected from: Parkinson's disease; migraine; epilepsy; Alzheimer's disease; brain injury; stroke; cerebrovascular disease (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment); mental deficiency (including spasticity, Down syndrome and fragile X syndrome); sleep disorders (including hypersomnia, circadian rhythm sleep disorder, insomnia, parasomnia, and sleep deprivation); psychiatric disorders such as anxiety (including acute stress disorder, generalized anxiety disorder, social anxiety disorder, panic disorder, post-traumatic stress disorder, agoraphobia, and obsessive compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, premenstrual syndrome (PMS), premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema) and pediatric psychiatric disorders (including attention deficit disorder, attention deficit/hyperactivity disorder, conduct disorder, and autism) in a subject, preferably a human, wherein the method comprises administering to a subject a therapeutically effective amount of the polypeptides described herein.

Other disorder which may be treated with the compounds described herein include, but are not limited to, lysosomal disorders (for example Niemann-Pick Type C disease, Gaucher disease), Crohn's disease, thyroid, renal (including papillary renal), breast, lung, and prostate cancers, leukemias (including acute myelogenous leukemia), lymphomas, multiple sclerosis, rheumatoid arthritis, system lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies.

In some embodiments, a method of treating Crohn's disease in a subject in need thereof is provided comprising administering a therapeutically effective amount of a synthetic stapled peptide to the subject.

EXAMPLES

By way of non-limiting illustration, examples of certain embodiments of the present disclosure are given below.

Example 1. From Structure and Function to
Allosteric Targeting of LRRK2-Mediated
Parkinson's Disease Recombinant purified LRRK2 can form constitutive dimers via the COR domain, however other parts of the protein may additionally contribute to dimerization. Consistent with these results, cell fractionation after chemical cross-linking revealed that dimeric LRRK2 was predominantly present in the membrane fraction, while the monomer was present in the cytosolic fraction (see Z. Berger, K. A. Smith, M. J. Lavoie, Membrane localization of LRRK2 is associated with increased formation of the highly active LRRK2 dimer and changes in its phosphorylation, Biochemistry, 49 (2010) 5511-5523). Moreover, time resolved FRET and EM showed that the GTP-induced monomerization occurs over a catalytically relevant time scale and that the monomer-dimer cycle occurs concomitant with GTP turnover (see E. Deyaert, L. Wauters, G. Guaitoli, A. Konijnenberg, M. Leemans, S. Terheyden, A. Petrovic, R. Gallardo, L. M. Nederveen-Schippers, P. S. Athanasopoulos, H. Pots, P. J. M. Van Haastert, F. Sobott, C. J. Gloeckner, R. Efremov, A. Kortholt, W. Versees, A homologue of the Parkinson's disease-associated protein LRRK2 undergoes a monomer-dimer transition during GTP turnover, Nat Commun, 8 (2017) 1008). A naturally occurring PD mutation was also found to decrease the GTPase activity by interfering with the monomer-dimer equilibrium (see E. Deyaert, L. Wauters, G. Guaitoli, A. Konijnenberg, M. Leemans, S. Terheyden, A. Petrovic, R. Gallardo, L. M. Nederveen-Schippers, P. S. Athanasopoulos, H. Pots, P. J. M. Van Haastert, F. Sobott, C. J. Gloeckner, R. Efremov, A. Kortholt, W. Versees, A homologue of the Parkinson's disease-associated protein LRRK2 undergoes a monomer-dimer transition during GTP turnover, Nat Commun, 8 (2017) 1008). Taken together, this shows a direct link between dimerization, LRRK2 catalytic activity and a naturally occurring PD mutation in LRRK2 that disrupts this balance.

In order to investigate these questions, whether it was possible synthetically disrupt RocCOR dimerization as a tool to probe dimer-mediated regulation was sought. As a strategy for disruption, constrained peptide libraries were developed using sequences derived from the Roc or COR domains of the dimerization interface of LRRK2.

A peptide derived from site 2 (derived from the COR domain) was subsequently tested in various assays to determine whether dimerization and signaling could effectively be disrupted. To first determine whether this stapled peptide could disrupt RocCOR dimerization of LRRK2, two labeled constructs (SNAP or GFP) of CORB were transiently transfected in HEK293 cells. Cell lysates were incubated overnight in the presence or absence of 1 µM stapled site 2 peptide and pull-downs were performed using GFP_TRAP beads. The peptide significantly disrupted dimerization where a weak band appeared only after a 3 hr exposure time. Next, to determine whether the site 2 stapled peptide could disrupt dimerization of full-length LRRK2, N-terminally Strep-Flap and GFP tagged versions of LRRK2 were transfected in HEK293 cells. Cell lysates were incubated overnight in the presence or absence of 1 µM stapled site 2 peptide and pull-downs performed using GFP_Trap beads demonstrated that the peptide was sufficient to block full-length LRRK2 dimerization. To assess whether the stapled peptide could affect kinase activity, the LRRK2 autophosphorylation site S1292 was investigated. In the presence of stapled peptide treatment, autophosphorylation was reduced. Lastly, to demonstrate that the stapled site 2 peptide was cell permeant, HEK293 cells were treated with FAM-labelled stapled peptide (10 µM) for 6 hrs prior to imaging. Fluorescein was readily detected in cells after treatment and showed broad distribution within the cell including the cytoplasm. Thus, preliminary data from these experiments demonstrate that the stapled peptide tested is cell permeable, nearly completely blocks LRRK2 dimerization and down-regulates LRRK2 kinase activity. The LRRK2 dimerization disruptor peptides can be further refined and used to investigate regulation of dimerization and kinase/GTPase activity in LRRK2 and LRRK2 PD mutants.

Stapled Peptides were Designed and Synthesized Based on Structural Models:

Purification and crystallization of full-length LRRK2 has been elusive, in large part due to the large, complex nature of the protein; therefore, significant structural studies have focused on the bacterial homologs, namely "Roco" proteins (see K. Gotthardt, M. Weyand, A. Kortholt, P. J. Van Haastert, A. Wittinghofer, Structure of the Roc-COR domain tandem of C. tepidum, a prokaryotic homologue of the human LRRK2 Parkinson kinase. EMBO J 27, 2239-2249 (2008); S. Terheyden, F. Y. Ho, B. K. Gilsbach, A. Wittinghofer, A. Kortholt, Revisiting the Roco G-protein cycle. Biochem J 465, 139-147 (2015); B. K. Gilsbach, A. Kortholt, Structural biology of the LRRK2 GTPase and kinase domains: implications for regulation. Front Mol Neurosci 7, 32 (2014); and K. E. Rosenbusch, A. Kortholt, Activation Mechanism of LRRK2 and Its Cellular Functions in Parkinson's Disease. Parkinsons Dis 2016, U.S. Pat. No. 7,351,985 (2016)). As the RocCOR GTPase domain is thought to be an important component of LRRK2 dimerization, we analyzed a structural model of this dimer interface to identify key contributors to dimer formation. We identified two alpha helices, one in the Roc domain "Roc" and one in the "COR" domain "COR", that energetically contribute to dimerization by binding along large, hydrophobic clefts. Sequence alignment of these peptide sequences across the family of human ROCO proteins indicates lack of sequence conservation for this protein-protein interface (PPI). After analyzing the sequence, homologous protein structures, and the structural model of LRRK2, amino acids that were predicted to form the PPI were identified, and these amino acids remained unchanged. Standard Fmoc-based solid phase peptide synthesis (SPPS) on solid support was then performed and Fmoc-(S)-2-(4-pentenyl)alanine amino acids were incorporated at an i, i+4 position along the non-binding interface to allow a full helical turn between olefinic amino acids. As the Roc-targeting peptide had a series of amino acids along the non-binding interface, a small library of peptides with shifted staple positions was developed to identify the ideal position for binding. The COR-targeting peptide had a much smaller sequence, so olefinic amino acids were incorporated at the only i, i+4 position that was suitable for replacement. The peptides were macrocyclized while on solid support to yield the chemically constrained alpha-helical products. Further modification included incorporation of a $PEG_3$ linker to improve hydrophilicity of the peptide.

Target Affinity Measurements:

Binding of peptides to LRRK2 are characterized by using FP, SPR and ITC to determine the affinity of each allosteric regulator peptide towards its intended monomeric target. All measurements are performed using recombinantly expressed proteins. Bacterial strains were recently generated that express properly folded wild-type and PD-related LRRK2 fragments, including the LRRK2 RocCOR tandem and the C-terminal subdomain of the COR domain that mediates dimerization (see E. Deyaert, L. Wauters, G. Guaitoli, A. Konijnenberg, M. Leemans, S. Terheyden, A. Petrovic, R. Gallardo, L. M. Nederveen-Schippers, P. S. Athanasopoulos, H. Pots, P. J. M. Van Haastert, F. Sobott, C. J. Gloeckner, R. Efremov, A. Kortholt, W. Versees, A homologue of the Parkinson's disease-associated protein LRRK2 undergoes a monomer-dimer transition during GTP turnover, Nat Commun, 8 (2017) 1008).

Expression and purification of the $His_6$-MBP-tagged Roc-COR was performed similar to the purification of the COR-B construct. The pBADcLIC vector containing the RocCOR coding region was transformed into an E. coli strain (E. coli RCEv9) that was custom evolved in-house starting from a MC1061 □acrB strain for optimal expression of the RocCOR protein, using previously described protocols (see E. Purlyte, H. S. Dhekne, A. R. Sarhan, R. Gomez, P. Lis, M. Wightman, T. N. Martinez, F. Tonelli, S. R. Pfeffer, D. R. Alessi, Rab29 activation of the Parkinson's disease-associated LRRK2 kinase, EMBO J, 37 (2018) 1-18; and Z. Berger, K. A. Smith, M. J. Lavoie, Membrane localization of LRRK2 is associated with increased formation of the highly active LRRK2 dimer and changes in its phosphorylation, Biochemistry, 49 (2010) 5511-5523). An overnight culture was used to inoculate 4 L of TB medium (37° C.), and when an OD of about 0.7 was reached protein expression was induced with 0.01% of arabinose and allowed to proceed overnight at 20° C. Cells were harvested and resuspended into a buffer containing 50 mM Tris-HCl pH 7.5, 500 mM NaCl, 10 mM $MgCl_2$, 2 mM β-mercaptoethanol and 20 mM imidazole and supplemented with 1 mM of PMSF, 1 µg/mL of Leupeptin, 0.1 µg/mL of AEBSF and 50 µg/mL of DNaseI. Finally, either 0.5 mM GDP or 0.5 mM Guanosine-5'-[(β,γ)-imido]triphosphate (GppNHp) was added to the buffer prior to cell lysis. Cells were lysed using a Cell Disrupter (Constant Systems Ltd.) and after clearance via centrifugation the cell lysate was loaded on a 5 mL Ni-NTA column. First, the column matrix was washed with 10 column volumes (CV) of resuspension buffer supplemented with 300 mM KCl and 5 mM ATP to reduce contamination with chaperones. Subsequently, the column was washed with 10 CV of a buffer containing 50 mM Tris-HCl pH 7.5, 150 mM NaCl, 10 mM $MgCl_2$, 20 mM imidazole, 5% glycerol, 2 mM β-mercaptoethanol and either 0.5 mM GDP or GppNHp, and the proteins were eluted in the same buffer supplied with 300 mM imidazole. After a concentration step, a final purification step consisted of a gel filtration on a Superdex S200 10/300 column using 30 mM HEPES pH 7.5, 150 mM NaCl, 5 mM $MgCl_2$, 5% glycerol, 1 mM DTT as a buffer supplemented with either 0.5 mM GDP or GppNHp.

A construct of the Roc domain spanning the residues 1329-1520 was cloned in the pET-28a vector providing an N-terminal $His_6$-tag, and the vector was transformed in the E. coli BL21(DE3) strain. An overnight culture was used to inoculate 4 L of TB medium (37° C.), and when an OD of about 0.7 was reached protein expression was induced with 0.1 mM isopropyl β-D-1-thiogalactopyranoside (IPTG) and allowed to proceed overnight at 20° C. Cells were harvested and resuspended into a buffer containing 30 mM HEPES pH 7.5, 250 mM NaCl, 10 mM $MgCl_2$, 10 mM glycine and 20 mM imidazole and supplemented with 1 mM of PMSF, 1 µg/mL of Leupeptin, 0.1 µg/mL of AEBSF and 50 µg/mL of DNaseI. Cells were lysed using a Cell Disrupter (Constant Systems Ltd.) and after clearance via centrifugation, the cell lysate was loaded on a 5 mL Ni-NTA column. After extensive washing with 10 CV of the resuspension buffer, proteins were eluted in the same buffer containing 300 mM imidazole. A final purification step consisted of a gel filtration on a Superdex S75 10/300 column using 30 mM HEPES pH 7.5, 150 mM NaCl, 5 mM $MgCl_2$, 5% glycerol, 1 mM DTT as buffer.

A construct of the C-terminal part of the COR domain (COR-B) spanning the residues 1672-1840 was cloned in the pDEST-566 vector providing an N-terminal $His_6$-MBP-tag, and the vector was transformed in the E. coli BL21(DE3) strain. An overnight culture was used to inoculate 4 L of TB medium (37° C.), and when an OD of about 0.7 was reached protein expression was induced with 0.5 mM IPTG and allowed to proceed for 2 h at 20° C. Cells were harvested and resuspended into a buffer containing 30 mM HEPES pH 7.5, 200 mM NaCl, 1 mM EDTA and 1 mM DTT and supplemented with 1 mM of PMSF, 1 µg/mL of Leupeptin, 0.1 µg/mL of AEBSF and 50 µg/mL of DNaseI. Cells were lysed using a Cell Disrupter (Constant Systems Ltd.) and after clearance via centrifugation, the cell lysate was loaded on a 5 mL MBPTrap column (GE Healthcare). After washing with 10 CV of resuspension buffer, the protein was eluted in the same buffer containing 10 mM maltose. A final purification step consisted of a gel filtration on a Superdex S200 10/300 column using 30 mM HEPES pH 7.5, 150 mM NaCl as buffer.

A variety of different constructs are used. For FP-based experiments, peptides are modified to contain an N-terminal fluorescein and are tested with the RocCOR construct in triplicate over a concentration range of 2 pm to 5 µM. Subsequent analysis by SPR using analogs lacking the fluorescein moiety is performed to account for any potential binding effects that may be caused by the fluorescein addition. For extremely weak or strong affinity compounds, concentration ranges are adjusted as needed to achieve suitable binding curves.

The candidate allosteric regulator peptides are further analyzed by SPR. Experiments are done using Biacore T200 and 3000 instruments where biotinylated analogs of the candidate peptide regulators are captured by employing CAP chip technology over a surface concentration range (see J. Kibat, T. Schirrmann, M. J. Knape, S. Helmsing, D. Meier, M. Hust, C. Schroder, D. Bertinetti, G. Winter, K. Pardes, M. Funk, A. Vala, N. Giese, F. W. Herberg, S. Dubel, J. D. Hoheisel, Utilisation of antibody microarrays for the selection of specific and informative antibodies from recombinant library binders of unknown quality, N Biotechnol, 33 (2016) 574-581). Non-specific binding is determined using blank runs on a CAP chip lacking peptide or with scrambled immobilized peptides and these values are subtracted. The RocCOR construct is injected over a concentration range. Both association and dissociation phases are recorded to allow initial insights into the binding mechanism. Rate constants ($k_a$ and $k_d$) and equilibrium binding constants ($K_D$) are calculated. Binding studies are performed using at least two independent protein preps and measurements are performed in triplicate.

Cell-Based Disruption of Dimerization and Effect on Kinase Activity:

Although it is clear that LRRK2 is dimeric and active when bound at the plasma membrane, it is unknown if the protein is first activated in the cytosol, then dimerizes and translocates to the membrane, or vice versa where it first binds to the membrane and is then activated and dimerizes. The allosteric regulator peptides are used to correlate LRRK2 activation, dimerization and localization in cells. HEK293 cells are used. LRRK2 activity in these strains is measured in the presence or absence of stapled peptides by measuring LRRK2 autophosphorylation (Anti-LRRK2 phospho S1292 antibody [MJFR-19-7-8] (ab203181) and substrate phosphorylation (Anti-RAB10 (phospho T73) antibody [MJF-R21] (ab230261)).

HEK 293T cells were cultured in DMEM (supplemented with 10% Fetal Bovine Serum, 25 mM L-Glutamine and 0.5% Pen/Strep). For the assay, the cells were seeded onto six-well plates and transfected at a confluency of 50-70% with the individual Nb-GFP expression constructs, SF-tagged LRRK2(G2019S) and FLAG-HA Rab29 using a self-made polyethylenimine (PEI)-based transfection reagent (see G. Guaitoli, F. Raimondi, B. K. Gilsbach, Y. Gomez-Llorente, E. Deyaert, F. Renzi, X. Li, A. Schaffner, P. K. Jagtap, K. Boldt, F. von Zweydorf, K. Gotthardt, D. D. Lorimer, Z. Yue, A. Burgin, N. Janjic, M. Sattler, W. Versees, M. Ueffing, I. Ubarretxena-Belandia, A. Kortholt, C. J. Gloeckner, Structural model of the dimeric Parkinson's protein LRRK2 reveals a compact architecture involving distant interdomain contacts, Proc Natl Acad Sci USA, 113 (2016) E4357-4366). After 48 hrs cells were lysed in lysis buffer [30 mM Tris-HCL (pH7.4), 150 mM NaCl, 0.5% Nonident-P40, complete protease inhibitor cocktail, phosphatase inhibitor cocktail II & III (all Sigma)]. Lysates were cleared by centrifugation at 10,000×g and adjusted to a protein concentration of 1 μg/μl in 1×Laemmli Buffer. Samples were subsequently subjected to SDS PAGE and Western Blot analysis to determine LRRK2 pS1292 and Rab10 T72 phosphorylation levels, as described below. Total LRRK2 and Rab10 levels were determined as a reference.

For western blot analysis, protein samples were separated by SDS-PAGE using NuPAGE 10% Bis-Tris gels (Invitrogen) and transferred onto PVDF membranes (Thermo Fisher). To allow simultaneous probing for LRRK2 on the one hand and Rab and the Nb-GFP fusions on the other hand, membranes were cut horizontally at the 140 kDa MW marker band. After blocking non-specific binding sites with 5% non-fat dry milk in TBST (1 h, RT) (25 mM Tris, pH 7.4, 150 mM NaCl, 0.1% Tween-20), membranes were incubated overnight at 4° C. with primary antibodies at dilutions specified below. Phospho-specific antibodies were diluted in TBST/5% BSA (Roth GmbH). Non-phospho-specific antibodies were diluted in TBST/5% non-fat dry milk powder (BioRad). Phospho-Rab10 levels were determined by the site-specific rabbit monoclonal antibody anti-pRAB10 (pT73) (Abcam, ab230261) and LRRK2 autophosphorylation was determined by the site-specific rabbit monoclonal antibody anti-pLRRK2(pS1292) (Abcam, ab203181), both at a dilution of 1:2,000. Total LRRK2 levels were determined by the in-house rat monoclonal antibody anti-pan-LRRK2 (clone 24D8; 1:10,000) (see Y. Wang, T. G. Ho, D. Bertinetti, M. Neddermann, E. Franz, G. C. Mo, L. P. Schendowich, A. Sukhu, R. C. Spelts, J. Zhang, F. W. Herberg, E. J. Kennedy, Isoform-selective disruption of AKAP-localized PKA using hydrocarbon stapled peptides, ACS Chem Biol, 9 (2014) 635-642). Total Rab10 levels were determined by the rabbit monoclonal antibody anti-RAB10/ERP13424 (Abcam, ab181367) at a dilution of 1:5,000. Nb-GFP fusion proteins were detected using the rat monoclonal antibody anti-GFP (clone 3H9, ChromoTec) at a dilution of 1:2,000. For detection, goat anti-rat IgG or anti-rabbit IgG HRP-coupled secondary antibodies (Jackson ImmunoResearch) were used at a dilution of 1:15,000 in TBST/5% non-fat dry milk powder. Antibody-antigen complexes were visualized using the ECL plus chemiluminescence detection system (GE Healthcare) on Hyperfilms (GE Healthcare). Localization of fluorescently tagged overexpressed LRRK2 is analyzed by confocal microscopy.

Peptides Selectively Bind LRRK2 and Disrupt Dimerization:

As expression and purification of full-length LRRK2 has been highly variable, protein constructs were used to conduct fluorescence polarization (FP) assays. Protein concentrations ranged from 10 uM to 1 uM, and each concentration was treated with 10 nM peptide. To determine the binding affinity of CORB, an MBP-tagged CORB construct was treated with CORB and the measurement was taken 2 hours after incubation. The process remained the same for the MBP_RocCOR protein in the presence of Roc(v) with the addition of 4 mM GTP. Consistent with cell uptake, kinase activity, and dimerization disruption, Roc(v) exhibits binding affinity in the mid nanomolar (~50 nM) range while the CORB inhibitor binds in the low micromolar range (~2 uM).

Analysis of Potential Off-Target Effects:

To determine whether each of the LRRK2 dimerization disruptors interacts with, or adversely affects, other proteins within the cellular environment beyond its intended target, pull-down experiments are performed using biotin-labeled versions of the top two identified allosteric regulators as assessed from cell-based experiments. Using this approach, pull-downs are performed in HEK293 cell lysates over expressing LRRK2. If there are either large numbers of interacting proteins, or strong associations with proteins that can be predicted to have adverse consequences as a result of interactions with these proteins (e.g. major metabolizing proteins, transcription factors), making minor modifications to the peptide are potentially made to minimize these interactions, such as increasing the overall peptide length derived from its parent compound.

Effect on LRRK2 Localization:

Inhibition of LRRK2 kinase activity was shown to induce cellular recruitment of LRRK2 to microtubules. Such altered localization of LRRK2 has recently been linked to reduction of kinesin and dynamin-mediated transport (see E. Purlyte, H. S. Dhekne, A. R. Sarhan, R. Gomez, P. Lis, M. Wightman, T. N. Martinez, F. Tonelli, S. R. Pfeffer, D. R. Alessi, Rab29 activation of the Parkinson's disease-associated LRRK2 kinase, EMBO J, 37 (2018) 1-18). To investigate whether identified dimerization disruptor peptides will result in a similar phenotype, HEK293 cells are transfected with a construct encoding GFP_LRRK2 and are treated with stapled peptide 24 hrs hours after transfection. Cells are examined with a confocal microscopy after 6 hrs and data acquisition was done with a ×63 oil-immersion objective with a Zeiss LSM800 confocal laser scanning microscope. Image analysis of z-scan was done using the Zeiss microscope software ZEN. Results showed that LRRK2 maintained its cytoplasmic distribution after treatment with dimerization disruptor peptides and no relocalization to microtubules is observed, suggesting that induced monomeric LRRK2 is adopting a different conformation compared to the conformation induced by classical pharmacological inhibitors.

Design Optimization:

Although the disruptor peptides in these studies range from 9-15 amino acids in length, only a fraction of the amino acid side chains are expected to directly interact at the dimerization interface while the other residues of the peptide regulator are expected to remain solvent-exposed. Since approximately 4-7 residues comprise the anticipated protein-protein interface upon binding, a rational design approach can be undertaken to determine whether side chain modifications at these positions will increase affinity. Each of these 7 positions can be analyzed independently via in silico modeling (Rosetta) as previously described (see M. D. Fulton, L. E. Hanold, Z. Ruan, S. Patel, A. M. Beedle, N. Kannan, E. J. Kennedy, Conformationally constrained peptides target the allosteric kinase dimer interface and inhibit EGFR activation, Bioorg Med Chem, (2017)). Different amino acids with distinct physical properties such as size (small versus large; i.e. Gly versus Trp), charge (acidic versus basic; i.e. Asp versus Arg) and polarity (polar versus non-polar; i.e. Cys, Ser, Thr, Tyr versus Leu, Ile, Pro, Trp) can be introduced at each of the binding face positions to explore their effects on target binding. An alternative, more high-throughput library approach such as "split and pool" synthesis may also be taken. Using this solid support synthesis strategy, all 20 amino acids or non-natural amino acids are introduced into sites of interest, in this case, the 7 amino acid side chains that comprise the binding interface. A spacer is incorporated to avoid steric hindrance between the bead-peptide complex and the RocCOR target protein. After synthesis is completed, these support-bound libraries can be screened directly against a fluorescently labeled RocCOR construct. Positive hits are isolated and individually sequenced by Orbitrap MS/MS mass spectrometry. Therapeutic candidate stapled peptides can also be additionally modified to bestow blood-brain barrier permeability once active allosteric regulators are identified (see B. Oller-Salvia, M. Sanchez-Navarro, E. Giralt, M. Teixido, Blood-brain barrier shuttle peptides: an emerging paradigm for brain delivery, Chem Soc Rev, 45 (2016) 4690-4707).

Example 2. Allosteric Inhibition of Parkinson's-linked LRRK2 by Constrained Peptides Parkinson's Disease (PD) is the second most common neurodegenerative disorder worldwide, with over 10 million active cases globally and at least 60,000 new diagnoses in the US each year (E. R. Dorsey et al., Projected number of people with Parkinson disease in the most populous nations, 2005 through 2030. *Neurology* 68, 384-386 (2007)). PD can result in bradykinesia, resting tremor, postural instability, rigidity, and memory loss, with the severity of the disease varying among individuals (W. Dauer, S. Przedborski, Parkinson's disease: mechanisms and models. *Neuron* 39, 889-909 (2003)). While aging remains the largest risk factor for PD, the relatively recent identification of over 20 genes associated with familial PD highlights potential signaling pathways involved in disease pathogenesis (C. Klein, A. Westenberger, Genetics of Parkinson's disease. *Cold Spring Harb Perspect Med* 2, a008888 (2012); R. C. Duvoisin, Recent advances in the genetics of Parkinson's disease. *Adv Neurol* 69, 33-40 (1996); M. H. Polymeropoulos et al., Mutation in the alpha-synuclein gene identified in families with Parkinson's disease. *Science* 276, 2045-2047 (1997); R. Kruger et al., Ala30Pro mutation in the gene encoding alpha-synuclein in Parkinson's disease. *Nat Genet* 18, 106-108 (1998); M. Farrer et al., A chromosome 4p haplotype segregating with Parkinson's disease and postural tremor. *Hum Mol Genet* 8, 81-85 (1999); and T. Gasser et al., A susceptibility locus for Parkinson's disease maps to chromosome 2p13. *Nat Genet* 18, 262-265 (1998)). Despite only 5-10% of PD cases exhibiting a genetic basis, identifying pathways altered in the genetic form of the disease could provide insight into innovative therapeutic targets and treatment strategies (T. Gasser, Mendelian forms of Parkinson's disease. *Biochim Biophys Acta* 1792, 587-596 (2009)).

Missense mutations in Leucine-Rich Repeat Kinase 2 (LRRK2) are the most common cause of genetic PD and are also present in a significant portion of idiopathic PD (iPD) cases (A. Zimprich et al., Mutations in LRRK2 cause autosomal-dominant parkinsonism with pleomorphic pathology. *Neuron* 44, 601-607 (2004)). LRRK2 mutations are relatively common, accounting for 5-6% of familial PD cases and 1-2% of sporadic PD cases; this prevalence is significantly larger in specific ethnic groups (A. Verstraeten, J. Theuns, C. Van Broeckhoven, Progress in unraveling the genetic etiology of Parkinson disease in a genomic era. *Trends Genet* 31, 140-149 (2015)). Containing an Armadillo domain (ARM), an Ankyrin Repeat (ANK), a Leucine-Rich Repeat (LRR), a Ras-like GTPase (RocCOR) domain, a Ser/Thr kinase domain and a C-terminal WD40 domain, the large 2,527 amino acid structure and complex activation mechanism of LRRK2 has incited investigation into the underlying mechanism(s) driving its pathogenesis (A. Biosa et al., GTPase activity regulates kinase activity and cellular phenotypes of Parkinson's disease-associated LRRK2. *Hum Mol Genet* 22, 1140-1156 (2013); and I. F. Mata, W. J. Wedemeyer, M. J. Farrer, J. P. Taylor, K. A. Gallo, LRRK2 in Parkinson's disease: protein domains and functional insights. *Trends Neurosci* 29, 286-293 (2006)). PD-associated LRRK2 mutations are most abundant in the catalytic core of the protein: the RocCOR GTPase domain (R1437H, R1441G/H/C, Y1699C) and the protein kinase domain (G2019S, I2020T) (J. Q. Li, L. Tan, J. T. Yu, The role of the LRRK2 gene in Parkinsonism. *Mol Neurodegener* 9, 47 (2014)). Each mutation results in altered GTPase and/or kinase activity, and this aberrant activity triggers alterations in vesicular trafficking, cytoskeletal dynamics, autophagy, lysosomal function, oxidative stress, neurotransmission, and mitochondrial function (E. Tolosa, M. Vila, C. Klein, O. Rascol, LRRK2 in Parkinson disease: challenges of clinical trials. *Nat Rev Neurol* 10.1038/s41582-019-0301-2 (2020)). Importantly, a common non-coding variation in LRRK2 modulates risk for PD (J. Simon-Sanchez et al., Genome-wide association study reveals genetic risk underlying Parkinson's disease. *Nat Genet* 41, 1308-1312 (2009)). Moreover, elevated LRRK2 kinase activity, independent of mutations, was even reported in iPD (R. Di Maio et al., LRRK2 activation in idiopathic Parkinson's disease. *Sci Transl Med* 10 (2018)), indicating that targeting LRRK2 is not only beneficial for the population who carry pathogenic LRRK2 coding variants but might also be relevant for iPD patients carrying a wild-type version of this gene.

Successful inhibition of the kinase domain of LRRK2 using ATP-competitive small molecule inhibitors leads to downregulated kinase activity, reduced oxidative stress, and limited neuronal toxicity (X. Deng, H. G. Choi, S. J. Buhrlage, N. S. Gray, Leucine-rich repeat kinase 2 inhibitors: a patent review (2006-2011). *Expert Opin Ther Pat* 22, 1415-1426 (2012)). However, a major shortcoming of these small molecule inhibitors is that they also induce mislocalization of LRRK2, resulting in altered vesicular trafficking and lysosomal function, mitochondrial dysfunction, and lung and kidney abnormalities (R. N. Fuji et al., Effect of selective LRRK2 kinase inhibition on nonhuman primate lung. *Sci Transl Med* 7, 273ra215 (2015)). Therefore, this has severely limited the translational potential of currently available small molecule inhibitors of LRRK2 and underscores the need for alternative targeting strategies to inhibit LRRK2 function. One possible strategy would be to take advantage of the different states LRRK2 cycles between, as part of the regulation of its kinase function. Structural and functional assays have shown that LRRK2 cycles between the cytoplasm and membranous organelles (Z. Berger, K. A. Smith, M. J. Lavoie, Membrane localization of LRRK2 is associated with increased formation of the highly active LRRK2 dimer and changes in its phosphorylation. *Biochemistry* 49, 5511-5523 (2010); N. G. James et al., Number and brightness analysis of LRRK2 oligomerization in live cells. *Biophys J* 102, L41-43 (2012); and E. Greggio et al., The Parkinson disease-associated leucine-rich repeat kinase 2 (LRRK2) is a dimer that undergoes intramolecular autophosphorylation. *J Biol Chem* 283, 16906-16914 (2008)). In the cytosol, LRRK2 appears to be mostly monomeric and has low kinase activity, while it is predominantly dimeric and active when localized at membranes. Furthermore, several LRRK2 PD variants result in an impaired monomer-dimer equilibrium (E. Leandrou et al., Kinase activity of mutant LRRK2 manifests differently in hetero-dimeric vs. homo-dimeric complexes. *Biochem J* 476, 559-579 (2019); C. X. Wu et al., Parkinson's disease-associated mutations in the GTPase domain of LRRK2 impair its nucleotide-dependent conformational dynamics. *J Biol Chem* 294, 5907-5913 (2019); B. J. Sanstrum et al., Fluctuation Imaging of LRRK2 Reveals that the G2019S Mutation Alters Spatial and Membrane Dynamics. *Molecules* 25 (2020); and E. Deyaert et al., A homologue of the Parkinson's disease-associated protein LRRK2 undergoes a monomer-dimer transition during GTP turnover. *Nat Commun* 8, 1008 (2017)). These data thus suggest that dimer formation and kinase activation are directly linked (W. C. Nichols et al., Genetic screening for a single common LRRK2 mutation in familial Parkinson's disease. *Lancet* 365, 410-412 (2005); J. Kachergus et al., Identification of a novel LRRK2 mutation linked to autosomal dominant parkinsonism: evidence of a common founder across European populations. *Am J Hum Genet* 76, 672-680 (2005); V. Bonifati, Parkinson's disease: the LRRK2-G2019S mutation: opening a novel era in Parkinson's disease genetics. *Eur J Hum Genet* 14, 1061-1062 (2006); and A. B. West et al., Parkinson's disease-associated mutations in leucine-rich repeat kinase 2 augment kinase activity. *Proc Natl Acad Sci USA* 102, 16842-16847 (2005)).

Furthermore, recent structural work (R. Watanabe et al., The In Situ Structure of Parkinson's Disease-Linked LRRK2. *Cell* 10.1016/j.cell.2020.08.004 (2020); and C. K. Deniston et al., Parkinson's Disease-linked LRRK2 structure and model for microtubule interaction. 10.1101/2020.01.06.895367% J bioRxiv, 2020.2001.2006.895367 (2020)) and molecular dynamics simulations (J.-H. W. Sven H. Schmidt, Phillip C. Aoto, Daniela Boassa, Sebastian Mathea, Steven Silletti, Junru Hu, Maximilian Wallbott, Elizabeth A Komives, Stefan Knapp, Friedrich W. Herberg, Susan S. Taylor, Conformation and dynamics of the kinase domain drive subcellular location and activation of LRRK2. bioRxiv 10.1101/2020.07.13.198069 (2020)) indicate that changes in the kinase domain allosterically signal back and forth throughout the entire molecule (S. S. Taylor et al., Kinase Domain Is a Dynamic Hub for Driving LRRK2 Allostery. *Front Mol Neurosci* 13, 538219 (2020)). This could potentially be exploited as an effective strategy for allosteric inhibition of LRRK2 kinase activity.

In order to analyze the role of LRRK2 dimerization on kinase regulation, all-hydrocarbon stapled peptides to allosterically disrupt the dimer interface were designed. In contrast to small molecule inhibitors, which rely on hydrophobic pockets and the engagement of a few key amino acids for binding, peptides can target elongated binding surfaces that are typically ill-suited to small molecules (G. L. Verdine, G. J. Hilinski, Stapled peptides for intracellular drug targets. *Methods Enzymol* 503, 3-33 (2012)). By incorporating a staple along the non-binding interface, the hydrophobic backbone of the peptide is embedded and can result in improved peptide solubility while also improving resistance to proteolytic cleavage (Y. W. Kim, G. L. Verdine, Stereochemical effects of all-hydrocarbon tethers in i,i+4 stapled peptides. *Bioorg Med Chem Lett* 19, 2533-2536 (2009)). The design and synthesis of stapled peptides to effectively disrupt protein-protein interactions has been applied to a diverse array of targets across multiple diseases (for example, see L. G. Helton, E. J. Kennedy, Targeting Plasmodium with constrained peptides and peptidomimetics. *IUBMB Life* 72, 1103-1114 (2020); N. G. Bendzunas et al., Investigating PKA-RII specificity using analogs of the PKA: AKAP peptide inhibitor STAD-2. *Bioorg Med Chem* 26, 1174-1178 (2018); J. T. Manschwetus et al., A Stapled Peptide Mimic of the Pseudosubstrate Inhibitor PKI Inhibits Protein Kinase A. *Molecules* 24 (2019); J. K. Cowell et al., Suppression of Breast Cancer Metastasis Using Stapled Peptides Targeting the WASF Regulatory Complex. *Cancer Growth Metastasis* 10, 1179064417713197 (2017); M. D. Fulton et al., Conformationally constrained peptides target the allosteric kinase dimer interface and inhibit EGFR activation. *Bioorg Med Chem* 26, 1167-1173 (2018); and L. E. Hanold, M. D. Fulton, E. J. Kennedy, Targeting kinase signaling pathways with constrained peptide scaffolds. *Pharmacol Ther* 173, 159-170 (2017)). Here, stapled peptides were developed designed to target the LRRK2 Roc-COR dimerization interface. These peptides permeate cells, bind to LRRK2 and reduce kinase activity as well as reactive oxygen species (ROS) production. Furthermore, the peptides reduce the toxic cellular effects seen with pathogenic LRRK2 in primary cortical neurons. Additionally, the allosteric inhibitors do not induce mislocalization of LRRK2 to the microtubules that is frequently seen with small molecule inhibitors. This examples thus supports the hypothesis that dimerization is an important regulator of kinase activity and dimerization disruption may serve as a valid therapeutic target for treatment of LRRK2-mediated PD pathogenesis.

Materials and Methods

Constructs. Cloning of the Strep-FLAG (SF) tagged LRRK2 (pDEST(N)SF.LRRK2 constructs has been described previously (G. Guaitoli et al., Structural model of the dimeric Parkinson's protein LRRK2 reveals a compact architecture involving distant interdomain contacts. *Proceedings of the National Academy of Sciences* 113, E4357 (2016)). The generation of N-terminal Flag-tagged LRRK2 for the transfection of neuronal cultures has been described in V. Daniëls et al., Insight into the mode of action of the LRRK2 Y1699C pathogenic mutant. *Journal of Neurochemistry* 116, 304-315 (2011). N-terminal GFP-tagged LRRK2 (pcDNA3.1_GFP.LRRK2) has been generated by Gateway cloning. For the proximity biotinylation assay, two constructs were created encoding LRRK2 fusions with biotin ligase (BirA; N-term, Flag-tagged) and an acceptor peptide (AP, N-term; c-Myc tagged) (E. Leandrou et al., Kinase activity of mutant LRRK2 manifests differently in heterodimeric vs. homo-dimeric complexes. *Biochem J* 476, 559-579 (2019)). The cDNAs encoding Rab10 and Rab29 were ordered as synthetic genes and subcloned via the Gateway system into the pcDNA3.0-based pDEST N-HA/FLAG vector, generated in-house.

Cell culture. LRRK2 parental RAW 264.7 cells (ATCC, SC-6003) were cultured in Dulbecco's Modified Eagle's medium (DMEM, ATCC, 30-2002) supplemented with 10% FBS and 1% penicillin-streptomycin (Gibco, 15070063). HEK293(T) cells (ATCC, CRL-1573 and CRL-3216) and A549 cells (ATCC, CCL-185) were grown in Dulbecco's Modified Eagle's medium (DMEM, Gibco, 11960044) supplemented with 10% FBS and 1% penicillin-streptomycin-Glutamine (Gibco, 10378016).

Peptide synthesis. Peptide synthesis was performed using standard Fmoc solid phase peptide synthesis on Rink amide MBHA resin using standard N-Fmoc amino acids. All synthesis reagents and solvents were purchased from Fisher, Sigma-Aldrich, or Acros. Deprotection was performed using 25% (v/v) piperidine in 75% (v/v) N-methyl-pyrrolidinone (NMP) for 25 minutes with agitation. After each deprotection, resin was washed 3x for 30 seconds with NMP and agitation. Standard amino acids were coupled by adding 10 equivalents of amino acids followed by the addition of 9.9 equivalents of 2-(6-chloro-1H-benzotriazole-1-yl)-1,1,3,3-tetramethylaminium hexafluorophosphate (HCTU in NMP). 20 equivalents of N,N-diisopropyl ethylamine (DIEA, Fisher) was added to catalyze the addition of the amino acid. This solution was agitated for 45 minutes. For S5 ((S)—N-Fmoc-2-(4-pentenyl) alanine, Sigma Aldrich) and $PEG_3$ (Fmoc-11-amino-3,6,9-trioxaundecanoic acid, ChemPep), we added 4 equivalents of S5 or $PEG_3$, followed by the addition of 3.9 equivalents of HCTU. For LRIP4, Methionine 1466 was mutated to norleucine to improve synthetic yield. This substitution was contingent on evidence suggesting the Methionine was not essential for mediating dimerization.

To cyclize the olefinic amino acids and form the staple, we performed Ring Closing Metathesis (RCM) using $1^{st}$ generation Grubbs Catalyst. This reaction was performed on resin with 1,2-dichloroethane (DCE) using 0.4 equivalents of $1^{st}$ generation Grubbs catalyst for two separate 1-hour time periods. Upon completion of the sequence and closing of the staple, we made modifications to the N-terminus based on experimental needs. These modifications included the addition of a $PEG_3$ linker (previously described in J. K. Cowell et al., Suppression of Breast Cancer Metastasis Using Stapled Peptides Targeting the WASF Regulatory Complex. *Cancer Growth Metastasis* 10, 1179064417713197 (2017)) and labeling with either 5,6-carboxyfluorescein (FAM, Sigma Aldrich) or D-biotin (GoldBio). For FAM labeling, 2 equivalents of FAM were added with 1.8 equivalents HCTU and 4.6 equivalents of DIEA overnight in dimethylformamide (DMF) with agitation. For biotin labeling, 10 equivalents of biotin were added with 9.9 equivalents of HCTU, and 20 equivalents of DIEA in a 1:1 mixture of dimethylsulfoxide (DMSO) and DMF overnight with agitation. After overnight labeling, the peptides were cleaved from resin using 95% (v/v) trifluoroacetic acid (TFA), 2.5% (v/v) triisopropylsilane, and 2.5% (v/v) water then rotated for 5 hours at room temperature. Peptides were then precipitated in methyl-tert-butyl ether at 4° C. via centrifugation.

Peptide characterization. Following cleavage from resin, peptides were separated via RP-HPLC using a Zorbax analytical SB-C18 column. The mobile phase linear gradient was 10-100% water to acetonitrile with 0.1% TFA at a flow rate of 0.5 mL/minute. Peptides were then characterized via ESI-MS (Agilent 6120 Single Quadrupole) following separation over a Zorbax analytical SB-C18 column via HPLC (Agilent 1200). Peptide purification was performed using the same conditions over a semi-preparatory column with a flow rate of 4 mL/minute. To confirm peptide purity, products were analyzed by ESI-MS over a Zorbax analytical SB-C18 column.

To quantify peptides, intrinsic qualities of the N-terminal labels were used. For FAM labeled peptides, quantification was based on the absorbance at 495 nm in 10 mM Tris (pH 8) using an extinction coefficient of 69,000 $M^{-1}$ $cm^{-1}$. Biotin-labeled peptides were quantified by measuring decreased absorbance of the 2-hydroxyazobenzen-4'-carboxylic acid (HABA)-avidin complex at 500 nm.

The peptide for FAM-labeled LRIP4 was formed from a peptide of SEQ ID NO. 6 and had a mass of 2928.0 (expected=2929.39). The peptide for Biotin-labeled LRIP4 was formed from a peptide of SEQ ID NO. 6 and had a mass of 2796.6 (expected=2797.4).

The peptide for FAM-labeled LRIP4 scramble was formed from a peptide having a sequence Q(Nle) DKAESKNKERKLCXTIKX (SEQ ID NO. 22), where X is (S)-2-(4'-pentenyl)alanine, and had a mass of 2928.9 (expected=2929.4). The peptide for Biotin-labeled LRIP4 scramble was formed from a peptide of SEQ ID NO. 22 and had a mass of 2796.9 (expected=2797.4).

The peptide for FAM-labeled LCIP1 was formed from a peptide of SEQ ID NO. 16 and had a mass of 1983.6 (expected=1984.3). The peptide for Biotin-labeled LCIP1 was formed from a peptide of SEQ ID NO. 16 and had a mass of 1851.6 (expected=1852.3).

The peptide for FAM-labeled LCIP1 scramble was formed from a peptide having the sequence GKWEKXGELXKL (SEQ ID NO. 23), where X is (S)-2-(4'-pentenyl)alanine, and had a mass of 1983.6 (expected=1984.3). The peptide for Biotin-labeled LCIP1 scramble was formed from a peptide of SEQ ID NO. 23 and had a mass of 1851.6 (expected mass=1852.3).

Fluorescence Polarization (FP) Assays. Direct binding of the compounds (LRIP4 and LCIP1) to LRRK2 constructs was assessed via FP assays. For LRIP4, binding was measured with purified MBP-tagged RocCOR LRRK2 protein in the presence of 2 mM GTP and 10 mM $MgCl_2$. For LCIP1, binding was measured to purified MBP-tagged CORB. Each FAM-labeled peptide was plated at a final in-well concentration of 10 nM in 384-well microtiter plates. 1:2 dilutions of the protein were then performed from a concentration range of 5 μM to 1 nM. For each peptide: protein interaction, a range of at least 10 protein concentrations was examined, and each concentration was performed in triplicate. The assay was performed in FP buffer (20 mM MOPS pH 7, 150 mM NaCl, and 0.005% CHAPS) at room temperature. The peptide:protein mixture was incubated at room temperature for 2 hours with readings taken every 30 minutes. The final readings were obtained at 2 hours.

Pulldown experiments. Fresh lysate of HEK293 cells overexpressing GFP-tagged LRRK2 was mixed and incubated with biotin-labeled peptide (added to a final concentration of 10 μM) and incubated at 4° C. overnight. The mixture was then applied to Magnetic Strep-beads (Mag-Strep 'Type3' XT Beads (IBA, Gottingen, Germany)) and the immune complex was washed twice (10 mM Tris/HCl pH 7.5, 150 mM NaCl) and subjected to immunoblot analysis. Samples were separated on 6% Tris-Glycine gels, transferred onto a nitrocellulose membrane (GE Life-sciences), and processed for western analysis. Membranes were blocked in 5% dry milk in Tris-buffered saline plus Tween-20 for 1 hour and probed with rat monoclonal anti-LRRK2 (clone 24D8 1:1000, Gloeckner lab(69)) and incubated overnight at 4° C. with gentle shaking. Membranes were then washed three times for 10 min at room temperature in PBS containing 0.1% or 0.05% Tween-20 and then incubated for 1 hour with anti-rat IgG-HRP (sc-2750, Santa Cruz Biotechnology). Membranes were again washed three times for 10 min at room temperature in PBS containing 0.1% or 0.05 Tween-20. The membranes were coated with enhanced chemiluminescent (ECL) reagent (WesternSure PREMIUM, Li-COR biosciences), and proteins were detected using the C-Digit Imaging System (Li-COR Biosciences).

In vitro dimerization assay. HEK293 cells were co-transfected using JetPEI reagent (Polyplus transfection) with pcDNA3.1_GFP.LRRK2 and pDEST(N)SF.LRRK2. Cells were cultivated for 48 hours. The cells were then lysed with 200 μL ice-cold lysis buffer (10 mM Tris/HCl pH 7.5; 150 mM NaCl; 0.5 mM EDTA; 0.5% NP-40), complete EDTA-free protease inhibitor cocktail (Sigma-Aldrich Cat #11836170001) and Protease Inhibitor Cocktail, Sigma (cat. no. P-2714). The mixture was incubated and rotated on ice for 30 minutes with extensively pipetting every 10 minutes. Lysate was cleared by centrifugation for 10 min at 14000 g for 10 min at 4° C. The supernatant was transferred to a precooled tube and 300 μL dilution buffer (same as lysis buffer without NP-40) was added to the lysate. Peptides were added to a final concentration of 10 μM and the mixture was allowed to rotate at 4° C. overnight. GFP-LRRK2 was immunoprecipitated with Magnetic GFP nanotrap beads (ChromoTek). Immune complexes were washed twice with 10 mM Tris/HCl pH 7.5 and subjected to immunoblot analysis by boiling samples in sample buffer with a reducing agent. Samples were separated on 6% Tris-Glycine gels, transferred onto a nitrocellulose membrane (GE Healthcare), and processed for western analysis. Membranes were blocked in 5% dry milk in Tris-buffered saline plus Tween-20 for 1 hour and probed with mouse anti-Strep tag LRRK2, 1:1000 (34850, Qiagen) or Rabbit anti-GFP antibodies, 1:2500 (MA5-15256, Invitrogen) and incubated overnight at 4° C. with gentle shaking. Membranes were then washed three times for 10 min at room temperature in PBS containing 0.1% or 0.05% Tween 20 and then incubated for at least 1 hour (light protected) with secondary antibodies: mouse IgG kappa binding protein (m-IgG□ BP) conjugated to horseradish peroxidase (HRP), (sc-516102, Santa Cruz Biotechnology, 1:5000), or anti-rabbit HRP conjugated (#7074, Cell Signaling, 1:500). Membranes were again washed three times for 10 min at room temperature in PBS containing 0.1% or 0.05% Tween-20. The membranes were coated with enhanced chemiluminescent (ECL) reagent (WesternSure PREMIUM, Li-COR biosciences), and proteins were detected by C-Digit Imaging System (Li-COR Biosciences).

Flow Cytometry. HEK293 cells were plated in 96-well plates (50 000/well) and allowed to grow 24 h in complete growth medium (DMEM supplemented with 10% fetal bovine serum, L-glutamine). DMEM was carefully aspirated and cells were treated with fresh pre-warmed complete growth medium supplemented with 10 μM of peptide or DMSO. After 6 hours, cells were analyzed on Beckman Cytoflex flow cytometer (Beckman Coulter). Using forward and side scattered light, a gate for intact, non-aggregated cells was defined and the fluorescence of 10,000 events was collected within this cell gate. The fluorescent channel for FITC (488-nm excitation [ex], 525-nm emission [em]) was used. Data was analyzed using FlowJo software and the reported fluorescent intensity values represent arithmetic means of the results determined for the analyzed cells.

Confocal Microscopy. HEK293 cells were plated (40,000/well) on p-Slide (chambered coverslip, tissue-culture treated, 80826, Ibidi) and cultured for 24 hours in complete growth medium (DMEM supplemented with 10% fetal bovine serum, and L-glutamine). Then, DMEM was carefully aspirated and cells were treated with fresh pre-warmed growth medium (DMEM supplemented with FAM-labeled stapled peptide (10 μM) or DMSO). After 6 hours, cells were washed three times in warm PBS to remove excess peptide from the cell surface and left in pre-warmed low fluorescence imaging medium (FluroBrite DMEM, Gibco). Cells were immediately analyzed under a LSM800 confocal laser scanning microscope a pre-warmed incubation chamber (37° C.). By scanning through the z-planes of each cell, the outer plasma membrane borders were determined. Images were taken between the plasma membrane z-planes to obtain signals from internalized peptides and to minimize artificial signals from cell surface adhered peptides. The distribution of FAM-labeled peptides was analyzed using a 63× Plan-Apochromat oil-immersion objective (Zeiss). Image analysis of z-scan was done using the Zeiss microscope software ZEN.

Proximity biotinylation of LRRK2. To purify LRRK2 dimers, we relied on the proximity biotinylation technique recently described (E. Leandrou et al., Kinase activity of mutant LRRK2 manifests differently in hetero-dimeric vs. homo-dimeric complexes. *Biochem J* 476, 559-579 (2019); and M. Fernandez-Suarez, T. S. Chen, A. Y. Ting, Protein-protein interaction detection in vitro and in cells by proximity biotinylation. *J Am Chem Soc* 130, 9251-9253 (2008)). Briefly, two cDNAs were created encoding LRRK2 fusions with biotin ligase (BirA; N-term, Flag-tagged) and an acceptor peptide (AP, N-term; c-Myc tagged), and over-expressed in HEK293T cells grown in biotin-depleted medium (OptiMEM+2% FBS). The following day, the cells were treated with the indicated concentrations of the stapled peptides: LRIP4 and LCIP1. Stock peptides, fluorescently tagged, were diluted in serum-free medium, and added every 24 hours after transfection. After 48 hours following initiation of treatment (i.e. 72 hr of total expression), the cells were extensively washed in PBS, given a brief biotin pulse (50 μM, 5 min, 37° C.), followed by another 3× washes in PBS, centrifuged and the pellet snap frozen in a dry-ice/MeOH bath. Following lysis, extracts were diluted in TBST/BSA (10 mM Tris HCl, pH 7.6; 100 mM NaCl; 0.1% Triton X-100; 1% BSA) and 2.5 µg of protein loaded in parallel ELISA plates, coated with streptavidin (SA; to capture biotinylated LRRK2 dimers) and anti-LRRK2 (to quantify LRRK2 over-expression). To detect and quantify dimeric LRRK2, SA-coated plates were incubated with HRP-con-jugated anti-Flag antibodies (1 hour, room temperature). Since the biotin tag is only present on AP-LRRK2 fusions, and the flag epitope tag is located on the BirA-LRRK2 fusion, by using HRP-Flag as our detector reagent, we are specifically labeling dimeric LRRK2 present in the ELISA plates. On the parallel anti-LRRK2 coated plates (clone c41-2), total over-expressed LRRK2 was quantified using HRP-LRRK2 antibodies (clone N241) and used to normal-ize the relative amounts of dimeric LRRK2. The following LRRK2 dimers were assessed: WT/WT homodimers, WT/G2019S, and G2019S/G2019S homodimers.

LRRK2 Immunoblotting. Protein content per sample was determined by a bicinchoninic acid colorimetric assay (BCA), using bovine serum albumin as a standard (23225; Life Technologies). Next, 100 µg protein resolved on 6% Tris-glycine gels and transferred to nitrocellulose membrane (GE Lifesciences). Membranes were then blocked in 5% dry milk in Tris-buffered saline plus Tween-20 for 1 hour and probed with rabbit anti-LRRK2-pSer1292 (1:1000, ab203181, Abcam) overnight at 4° C. Membranes were washed three times for 10 min at room temperature in PBS containing 0.1% or 0.05% Tween 20 and then incubated for 1 hour min with anti-rabbit HRP conjugated (1:500, #7074, Cell Signaling). The membranes were coated with enhanced chemiluminescent (ECL) reagent (WesternSure PREMIUM, Li-COR biosciences) and proteins were detected by C-Digit Imaging System (Li-COR Biosciences). For total LRRK2 detection, membranes were subsequently stripped (0.2M Glycine pH 2.2, 0.1% SDS, 1% Tween-20), reblocked as above, and probed with rat monoclonal anti-LRRK2 (clone 24D8, 1:1000, Gloeckner lab(69)) overnight at 4° C. Mem-branes were then incubated with anti-rat IgG-HRP (sc-2750, Santa Cruz Biotechnology). Membranes were again washed three times for 10 min at room temperature in PBS contain-ing 0.1% or 0.05 Tween 20. The membranes were coated with enhanced chemiluminescent (ECL) reagent (Western-Sure PREMIUM, Li-COR biosciences), and proteins were detected by C-Digit Imaging System (Li-COR Biosciences). For quantification, images were analyzed with Image Studio (Li-COR) and signals were normalized to total LRRK2 and expressed as percentage of within-gel DMSO controls.

Rab10 Immunoblotting. HEK293T cells were co-trans-fected at a confluency of 50-60% with Strep-FLAG tagged LRRK2 R1441G and Rab29 as well as Rab10 (both HA-FLAG tagged) using polyethylenimine (PEI, Polyscience) as previously described(46). At a confluency of approximately 80%, cells were treated with either 1 µM MLi-2, DMSO or 10 µM of LRIP4 or LCIP1. After an additional 15 hours, cells were lysed in twice, first in lysis buffer (30 mM Tris-HCL (pH7.4), 150 mM NaCl, 0.5% NP-40, complete protease Inhibitor cocktail and phosphatase inhibitor cock-tail II & III (Sigma Aldrich) and again after centrifugation in 1% SDS. Cleared lysates were adjusted to 2 µg/µl with 5× Laemmli Buffer and lysis buffer. Samples were used for denaturing electrophoresis using 10% Bis-Tris gels (Nu-PAGE) and for western blotting onto PVDF membranes. Membranes were blocked with 5% non-fat dry milk dis-solved in TBS-T (30 mM Tris-HCL (pH 7.4), 0.1% Tween 20) and separated horizontally at 140 kDa. Primary anti-bodies were added TBS-T with 5% BSA (pT73 Rab10)

1:2,000 (ab230261) and pS1292 LRRK2 1:2,000 (ab203181)) or total protein antibodies (Rab10(ERP13424) 1:5,000 (ab181367) or LRRK2 (clone 24D8) 1:5,000 (Gloeckner lab)), respectively. Membranes were incubated with HRP-conjugated secondary antibodies diluted in TBS-T with 5% milk prior to imaging using ECL Plus (Pierce) with exposure to photometric films (Hyperfilms, GE Healthcare).

ROS production assay. Flow cytometry was used to measure reactive oxygen species (ROS) through fluores-cence emission of the CellROX deep red dye (Life Tech-nologies). RAW264.7 cells (ATCC® SC-6003™) were plated at 120,000/well in a 96-well low-adherence tissue culture plate (Costar). Cells were pre-incubated with stapled peptide or DMSO for 9 hours then stimulated with Zymosan particles (Sigma Aldrich) (for 30 mins (50 µg/mL). The CellROX staining was done according to the manufacturer's instructions; the CellROX reagent was added to the cell cultures at a final concentration of 2.5 µM, and the mixture was incubated for an additional 30 min. Cells were lifted, kept on ice, and analyzed immediately. Cells were then analyzed on Beckman Cytoflex flow cytometer (Beckman Coulter). The fluorescent channel was APC (638-nm exci-tation [ex], 660-nm emission [em]). Reported fluorescent intensity values represent arithmetic means of the results determined for analyzed cells.

Preparation of primary mouse neuronal cultures, and assessment of neuronal death. Embryonic day 16 (E16) pregnant C57BL mice were used in this study, with primary cortical neurons prepared as described (N. Antoniou et al., A motif within the armadillo repeat of Parkinson's-linked LRRK2 interacts with FADD to hijack the extrinsic death pathway. Sci Rep 8, 3455 (2018)). Briefly, under aseptic conditions, cortices were removed and cut into small pieces before enzymatic digestion (trypsin 0.05% and 100 µg/ml DNAse) and mechanical dissociation. Cells were centri-fuged and counted and plated at a density of 150,000/cm² in BrainPhys neuronal culture medium (StemCell Technolo-gies) supplemented with SM1 Neuronal Supplement (Stem-Cell Technologies), L-glutamine (0.5 mM) and penicillin/ streptavidin. After 3-4 DIV, neurons were transfected using Lipofectamine 2000 (Thermo Scientific) as per the manu-facturer's instructions. Neurons were transfected with Flag-tagged WT or mutant (G2019S) human LRRK2 (as described previously). The following day, the treatment of neurons with fluorescently labeled peptides (at 10 µM final concentration) was initiated. The peptides were replenished in the neuronal medium after 24 hours, and the indicated concentrations. After three days following transfection, and two days of treatment, the coverslips were washed in PBS and fixed in 3.7% paraformaldehyde for 20 min at 4° C. The neurons were processed for immunofluorescence labeling with the following antibodies: GFP (chicken; Abcam), Flag (M2 mouse; Sigma-Aldrich), active caspase-3 (rabbit; R&D Systems), and DAPI nuclear stain. Mounted coverslips were imaged on a Leica TSP5 multi-photon confocal microscope, and the Z-stacks processed in ImageJ, and Adobe Photo-shop. For quantification of apoptotic neuronal profiles, the approach described previously was used.

StatisticalAnalysis. GraphPad Prism was used for statis-tical analysis. One-way ANOVA and Dunnett's multiple comparisons test were used for analysis of western blots and ROS production. n.s.=not significant, *=p<0.05, =p<0.01, *=p<0.001, ****=p<0.0001. For neuronal apoptosis assay and in vitro dimerization assays, one-way ANOVA with Tukey post-hoc tests were performed. All experiments were performed in triplicate, at minimum. Unless otherwise stated, graphed data are presented as means±SEM.

Results

Design of Stapled Peptides Targeting the RocCOR Dimerization Interface of LRRK2

Until recently, purification and crystallization of LRRK2 constructs has proven elusive, in large part due to the large, complex nature of the protein; therefore, structural studies have initially focused on characterization of bacterial homologs, namely "Roco" proteins (B. K. Gilsbach et al., Roco kinase structures give insights into the mechanism of Parkinson disease-related leucine-rich-repeat kinase 2 mutations. *Proc Natl Acad Sci USA* 109, 10322-10327 (2012); and E. Deyaert et al., Structure and nucleotide-induced conformational dynamics of the *Chlorobium tepidum* Roco protein. Biochem J 476, 51-66 (2019)). As the RocCOR GTPase domain is considered essential for mediating LRRK2 dimerization (A. P. Nguyen, D. J. Moore, Understanding the GTPase Activity of LRRK2: Regulation, Function, and Neurotoxicity. *Adv Neurobiol* 14, 71-88 (2017)), we analyzed a structural model of this dimer interface to identify components of the interface that may contribute to dimer formation(46). We identified two alpha helices, one in the Roc domain and one in the COR domain, that contribute to the dimerization interface by binding along large hydrophobic clefts (FIG. 1A). Sequence alignment of these peptide sequences across the family of human Roco proteins indicates a lack of sequence conservation for this protein-protein interface (FIG. 1B). Upon closer examination of the peptide sequences, we sought to determine which amino acids were essential for dimer formation. After analyzing the sequence, homologous protein structures, and the structural model of LRRK2 (G. Guaitoli et al., Structural model of the dimeric Parkinson's protein LRRK2 reveals a compact architecture involving distant interdomain contacts. *Proceedings of the National Academy of Sciences* 113, E4357 (2016)), amino acids that were predicted to be involved in mediating the protein-protein interaction (PPI) were identified via structural analysis (FIG. 1C), and these amino acids remained unchanged. Olefinic amino acids were introduced in amino acid positions that were predicted to not contribute to dimerization (FIG. 1C). The olefinic amino acid Fmoc-(S)-2-(4-pentenyl)alanine was incorporated at i, i+4 positions along the nonbinding interface to allow a full helical turn between these non-natural amino acids (H. E. Blackwell, R. H. Grubbs, Highly Efficient Synthesis of Covalently Cross-Linked Peptide Helices by Ring-Closing Metathesis. *Angew Chem Int Ed Engl* 37, 3281-3284 (1998)). As the Roc-targeting peptide has a series of amino acids along the non-binding interface, we designed a small library of peptides with shifted stapled positions to identify the ideal position for minimal interference with binding. The COR-targeting peptide had a much smaller sequence; so olefinic amino acids were incorporated at only the i, i+4 positions that were suitable for replacement (FIG. 1C). Peptides were synthesized using Fmoc-based solid phase peptide synthesis (SPPS) on solid support and the olefinic amino acids were cyclized using Grubbs I Catalyst while on solid support to yield the constrained peptide products (FIG. 1D). Further modification included incorporation of an N-terminal PEG$_3$ linker to improve hydrophilicity of the peptide and additional N-terminal labelling with either biotin or 5,6-carboxyfluorescein (FAM) for relevant biochemical and cellular assays.

LCIP1 and LRIP4 Bind to LRRK2 and Disrupt Dimerization

Figure 2A:
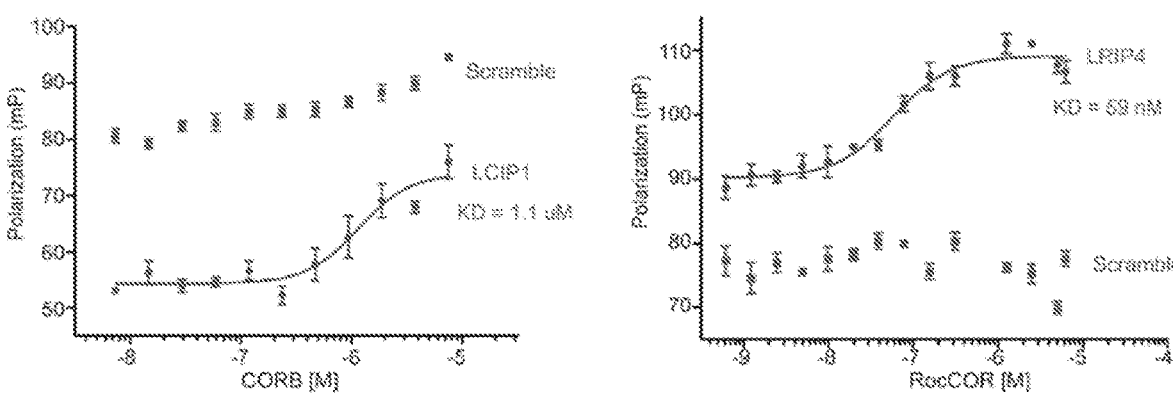
FIGS. 2A-2C show LCIP1 and LRIP4 bind LRRK2 in vitro and downregulate LRRK2 dimerization.

Peptides designed to target the Roc domain (LRRK2 Roc Interacting Peptides, LRIP) and COR domain (LRRK2 COR Interacting Peptides, LCIP) were first passed through a preliminary screen to determine whether they had any inhibitory effects LRRK2 dimerization (FIG. 6) by assessing co-immunoprecipitation of differently tagged LRRK2 constructs. From this first pass screen, LRIP4 and LCIP1 reduced the co-immunoprecipitation of the two LRRK2 proteins; therefore, we focused on these two peptides moving forward. The binding affinities of these two peptides towards LRRK2 was measured using fluorescence polarization (FP). Two MBP-tagged protein constructs, CORB and RocCOR, were purified and plated in concentrations ranging from 5 μM to 1 nM along with 10 nM FAM-labeled peptide, 2 mM GTP and 10 mM MgCl$_2$. LRIP4 exhibited a binding affinity in the mid nanomolar range (~50 nM) while LCIP1 bound to the CORB construct with significantly weaker interaction in the low micromolar range (~1 μM) (FIG. 2A).

Figure 2B:
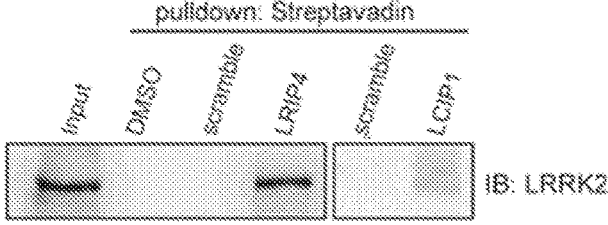

Next, we wanted to determine whether the lead peptides could bind their target, LRRK2, within the cellular environment. To test this, HEK293 cells overexpressing GFP-tagged LRRK2 were lysed and incubated with biotin-labeled peptides. Pulldowns were performed using avidin-coated resin. As compared to DMSO and scrambled controls, LRIP4 and LCIP1 successfully bound to LRRK2 (FIG. 2B). Of note, LRIP4 pulled down considerably more LRRK2 as compared to LCIP1, which correlates with this peptide binding LRRK2 with a higher affinity.

Figure 2C:
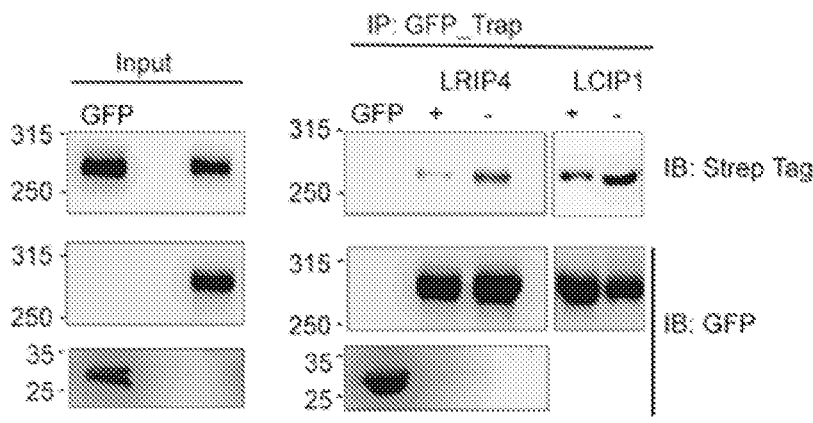
Figure 3A:
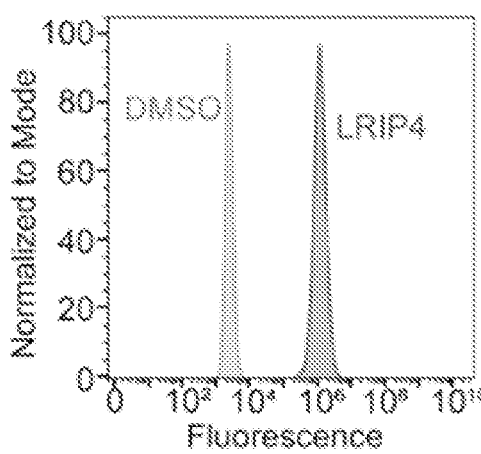
FIGS. 3A-3C show that LCIP1 and LRIP4 permeate cells and are detected in the cytoplasm.
Figure 3A:
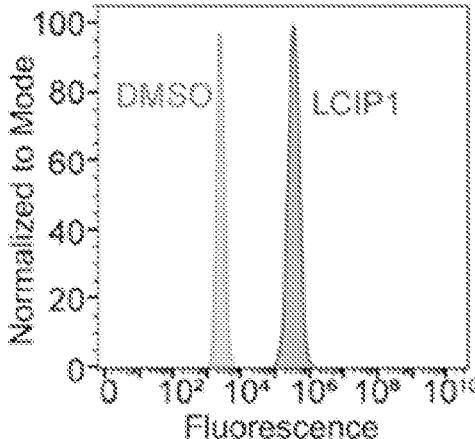
Figure 3B:
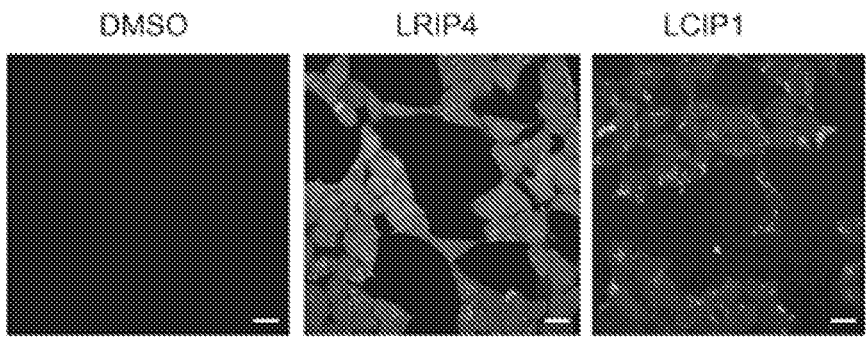
Figure 6:
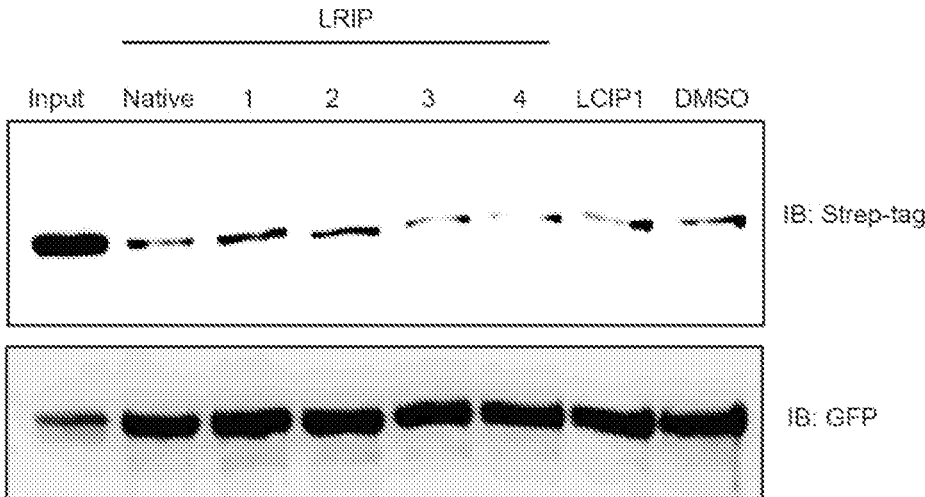
FIG. 6 shows that LRIP4 and LCIP1 disrupt LRRK2 dimerization. HEK293 cells were co-transfected with GFP tagged LRRK2 and Strep-tagged LRRK2 before peptide treatment. Co-immunoprecipitation revealed that LRIP4 and LCIP1 had an inhibitory effect on LRRK2. Blot is representative of n=3.
Figure 7:
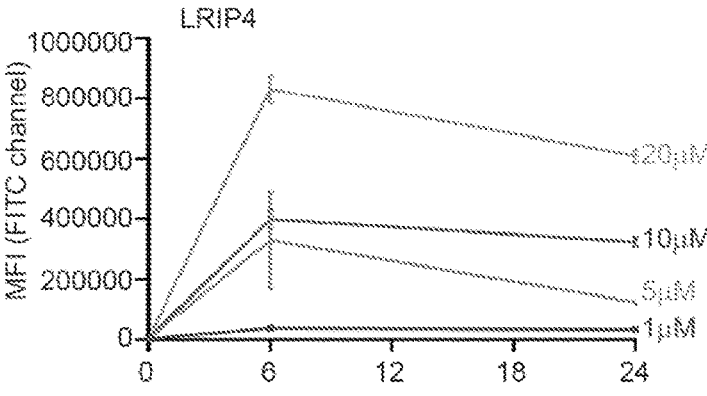
FIG. 7 shows dose-dependent uptake of LCIP1 and LRIP4. HEK293 cells were treated with 1-20 μM FAM-labeled LRIP4 or LCIP1 over a 24-hour time course at 37° C. Flow cytometry experiments demonstrate that both peptides yielded an increased shift in fluorescence maximally at 6 hours. Experiment was performed in triplicate.
Figure 7:
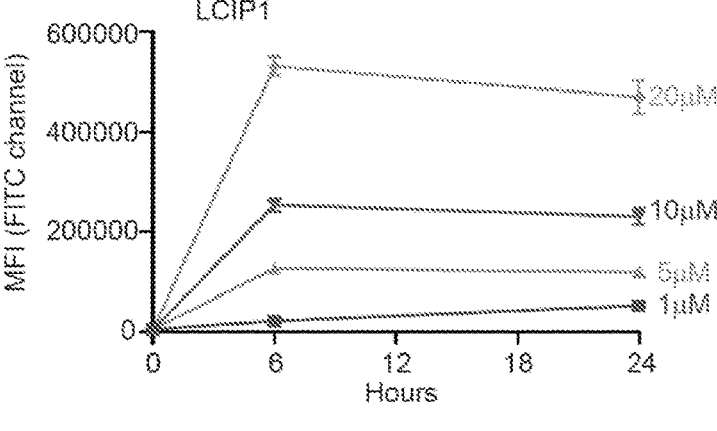

To determine whether LCIP1 and LRIP4 could effectively disrupt LRRK2 dimerization, we monitored disruption of dimerization using two different tagged versions of LRRK2. This was achieved by co-transfecting HEK293 cells with GFP-tagged and strep-tagged full-length LRRK2. Next, a GFP-trap immunoprecipitation was performed using lysates that were treated with 10 μM peptide overnight. Western blotting was performed to detect the level of Strep-tagged LRRK2. In the absence of peptide treatment, Strep-tagged full-length LRRK2 co-precipitated with GFP-LRRK2, indicating dimer formation (FIGS. 2C and 6). Both LRIP4 and LCIP1 were able to disrupt LRRK2 dimerization with LRIP4 having the most pronounced effect, albeit neither peptide yielded complete inhibition of dimer formation.
Peptides Permeate Cells and Inhibit Wild-Type and G2019S LRRK2 Dimerization in Cells To determine whether LCIP1 and LRIP4 would be suitable for cell-based experiments, cell permeation of the peptides was evaluated. Flow cytometry revealed dose-dependent uptake of both lead peptides (FIG. 7). After 6 hours, both peptides yielded a shifted cell population with increased fluorescence (FIGS. 3A and 7). Confocal microscopy showed that while both peptides were detected in the cytoplasm, LRIP4 had greater cytoplasmic fluorescence intensity as well as some nuclear signal, while LCIP1 appeared to have extensive localization within vesicles (FIG. 3B).

Figure 3C:
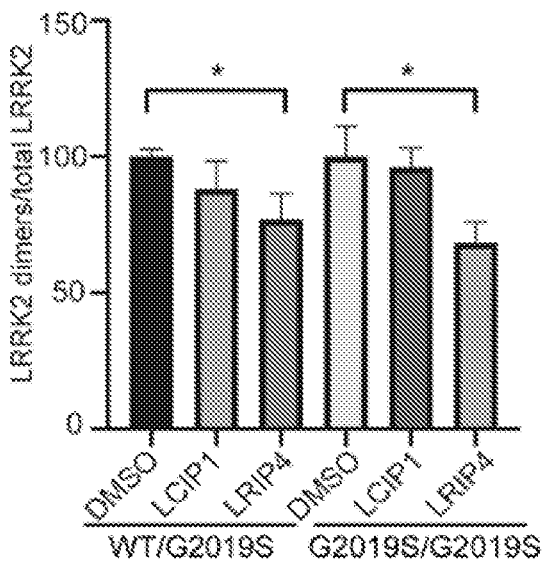
Figure 8:
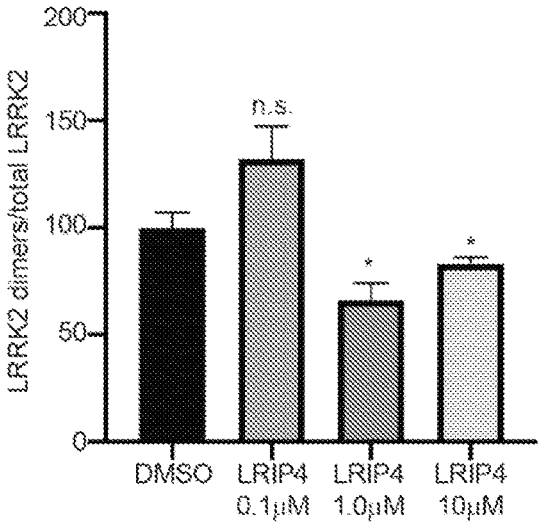
FIG. 8 shows that LRIP4 effectively disrupts LRRK2 dimerization in cells. Using a LRRK2 proximity biotinylation assay, it was determined that LRRK2 could disrupt dimerization at concentrations ranging from 1 mM to 10 mM, whereas LCIP1 had no statistically significant effect on dimerization. *p<0.05. n=3.
Figure 8:
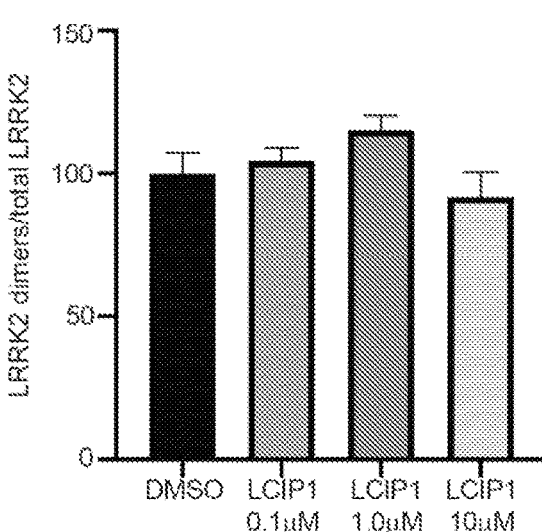
Figure 9:
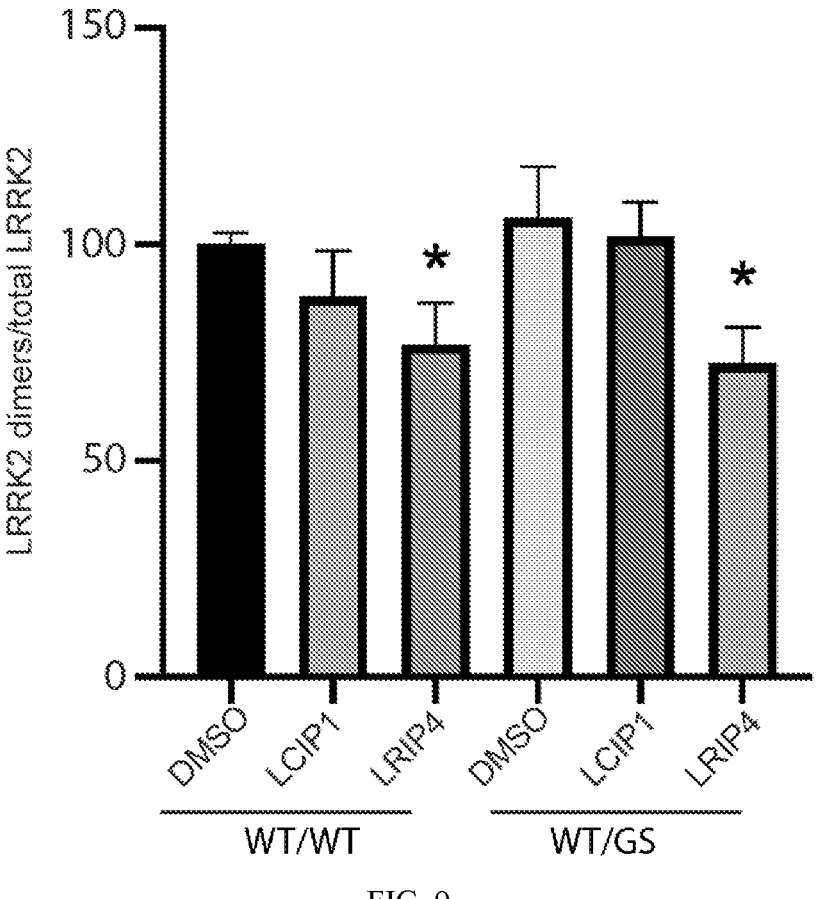
FIG. 9 shows that LRIP4 disrupts dimerization of homodimeric WT LRRK2 and heterodimeric WT/G2019S LRRK2. LRRK2 dimerization was measured in cells using a proximity biotinylation ELISA-based assay. Dimeric LRRK2 was biotinylated in situ and purified on streptavidin-coated ELISA plates. LRIP4 was found to inhibit dimerization of both wild-type LRRK2 homodimers and wild-type/G2019S LRRK2 heterodimers in HEK293 cells. *p<0.05. LCIP1 had no statistically significant effects on dimerization in this assay. n=3.

To determine if the peptides could also inhibit LRRK2 dimer formation in cells, we used a previously published LRRK2 proximity biotinylation approach. In this assay, HEK293T cells expressing either wild-type or G2019S mutants of LRRK2 fusions, either with the biotin ligase BirA or the acceptor peptide AP, were treated with increasing concentrations (0.1, 1, and 10 μM) of each fluorescently labeled peptide. The ROC domain-targeting peptide, LRIP4, caused a statistically significant reduction in both G2019S/G2019S and G2019S/wild-type LRRK2 dimers at 10 mM peptide treatment (FIGS. 3C and 8). In this assay, LCIP1 failed to consistently lead to a reduction in LRRK2 dimerization (FIG. 8) which might be due to relatively weaker cell permeation and weaker target binding as compared to LRIP4.

Figure 4A:
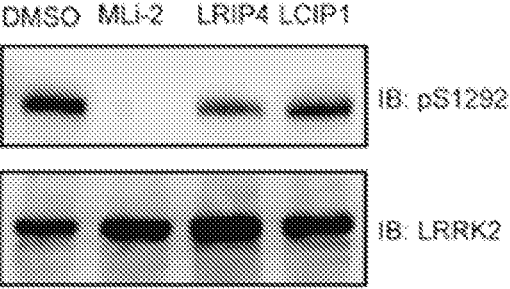
FIGS. 4A-4E show that LCIP1 and LRIP4 inhibit LRRK2 autophosphorylation and Rab10 phosphorylation.
Figure 4B:
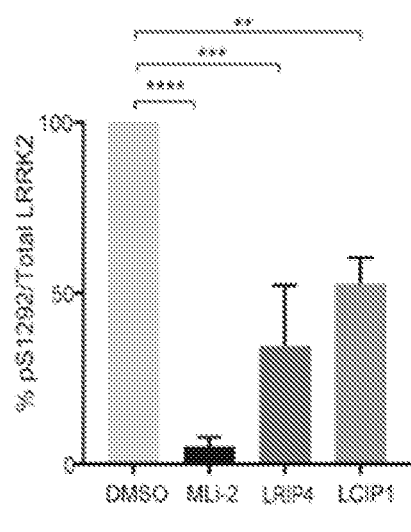

Disrupting LRRK2 Dimerization Attenuates LRRK2 Kinase Activity but does not Induce Mislocalization Since autophosphorylation of S1292 is correlated with LRRK2 kinase activity, it is commonly used as a surrogate marker for LRRK2 inhibition (Z. Sheng et al., Ser1292 autophosphorylation is an indicator of LRRK2 kinase activity and contributes to the cellular effects of PD mutations. *Sci Transl Med* 4, 164ra161 (2012)). To test whether impaired LRRK2 dimerization may result in attenuation of S1292 autophosphorylation, HEK293 cells were transfected with GFP-tagged LRRK2. Twenty-four hours post transfection, cells were treated with 10 µM of either LRIP4 or LCIP1 for a 12-hour window. Immunoblotting analysis of pS1292-LRRK2 revealed that both peptides caused a significant reduction of autophosphorylation by 50-70% as compared to the DMSO control, although neither was as effective as the ATP-competitive inhibitor MLi-2 (FIGS. 4A and 4B).

Figure 4C:
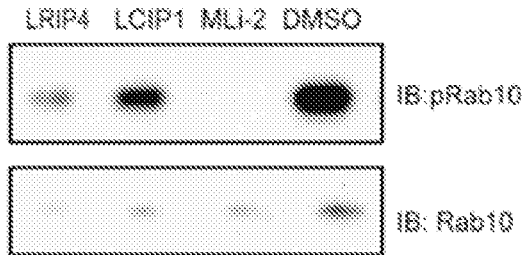
Figure 4D:
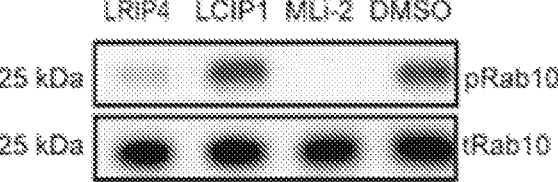

Another generally accepted measure of LRRK2 kinase activity is Rab10 phosphorylation (M. Steger et al., Phosphoproteomics reveals that Parkinson's disease kinase LRRK2 regulates a subset of Rab GTPases. *Elife* 5 (2016); and G. Yin et al., alpha-Synuclein interacts with the switch region of Rab8a in a Ser129 phosphorylation-dependent manner. *Neurobiol Dis* 70, 149-161 (2014)). To test whether disruption of LRRK2 dimerization can also attenuate Rab phosphorylation, a hyperactive LRRK2 mutant (R1441G) and Rab29 were overexpressed in HEK293T cells (Z. Liu et al., LRRK2 phosphorylates membrane-bound Rabs and is activated by GTP-bound Rab7L1 to promote recruitment to the trans-Golgi network. *Hum Mol Genet* 27, 385-395 (2018); and E. Purlyte et al., Rab29 activation of the Parkinson's disease-associated LRRK2 kinase. *The EMBO Journal* 37, 1-18 (2018)). Overexpression of Rab29 induces recruitment of LRRK2 to the trans-golgi network (TGN) and activates it there. After 24-hour transfection, cells were then treated with 10 µM peptide for 15 hours. Immunoblotting analysis of pT73 Rab10 showed that treatment with LRIP4 or LCIP1 reduced Rab10 phosphorylation with LRIP4 inducing a more pronounced effect (FIG. 4C). To test the effect of the dimerization inhibitors on endogenous LRRK2 function, we performed a similar experiment using non-transfected A549 cells which natively express detectable levels of both LRRK2 and Rab10. In these cells, LRIP4 caused a significant reduction in phosphorylation of Rab10 as compared to the DMSO control (FIG. 4D). Together, these results indicate that disrupted dimerization leads to reduced LRRK2 activation as assessed by autophosphorylation of LRRK2 and subsequent Rab10 phosphorylation. This demonstrates that LRRK2 dimerization controls LRRK2 kinase activation and disruption of dimerization can allosterically inhibit LRRK2 activity.

Figure 4E:
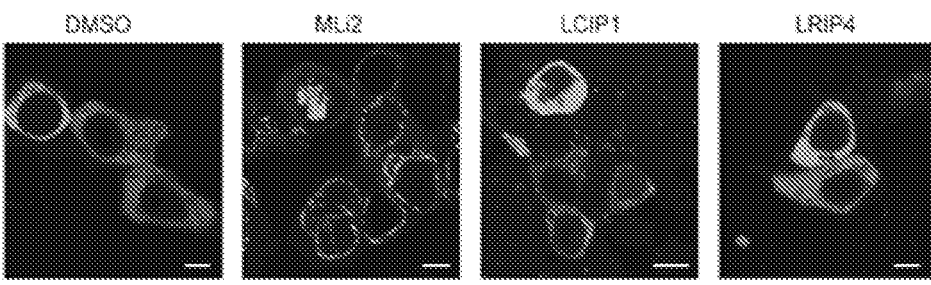

Next, we analyzed the effects of these inhibitor peptides on LRRK2 localization. Classical ATP-competitive LRRK2 kinase inhibitors induce cellular recruitment of LRRK2 to microtubules and block kinesin and dynein-1-mediated transport (Deniston, C. K. et al. Structure of LRRK2 in Parkinson's disease and model for microtubule interaction. Nature 2020, 588(7837):344-349). To investigate whether the dimerization-blocking peptides would induce a similar phenotype, the localization of GFP-tagged LRRK2 was analyzed by confocal microscopy (FIG. 4E). Consistent with previous studies, the LRRK2 ATP-competitive inhibitor MLi-2 induced altered localization to filament-like structures. This is also consistent with previous work demonstrating that kinase inhibitor-induced filaments are populated with dimeric LRRK2[21]. In contrast, LRRK2 maintained its cytoplasmic distribution after 12-hour treatments with 10 µM of either LRIP4 or LCIP1, suggesting that allosterically inhibited monomeric LRRK2 may be adopting a different conformation compared to catalytically inhibited LRRK2.

Figure 5A:
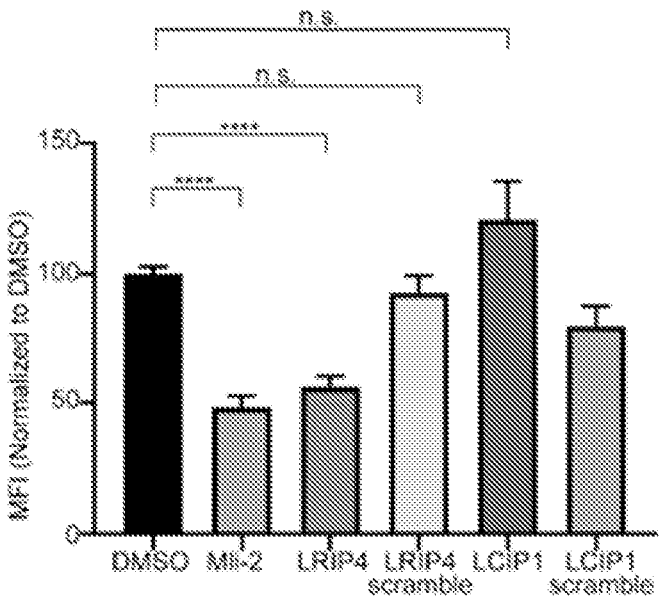
FIGS. 5A-5C show that LRIP1 downregulates ROS production and neuronal apoptosis.

Targeting LRRK2 Dimerization Inhibits LRRK2-Mediated ROS Production and Neuronal Apoptosis We subsequently sought to evaluate how allosteric inhibition of LRRK2 impacts PD-linked cellular effects. Although the exact physiological function of LRRK2 is still elusive, and in particular the mechanism(s) by which mutant forms induce neuronal death, pathogenic LRRK2 mutants were shown to impair lysosomal function and therefore account for increased levels of ROS production (D. C. Berwick, G. R. Heaton, S. Azeggagh, K. Harvey, LRRK2 Biology from structure to dysfunction: research progresses, but the themes remain the same. *Mol Neurodegener* 14, 49 (2019)) in both neuronal (S. Saez-Atienzar et al., The LRRK2 inhibitor GSK2578215A induces protective autophagy in SH-SY5Y cells: involvement of Drp-1-mediated mitochondrial fission and mitochondrial-derived ROS signaling. *Cell Death Dis* 5, e1368 (2014); and H. Y. Heo et al., LRRK2 enhances oxidative stress-induced neurotoxicity via its kinase activity. *Experimental Cell Research* 316, 649-656 (2010)) and peripheral immune cells (J. Kim et al., LRRK2 kinase plays a critical role in manganese-induced inflammation and apoptosis in microglia. *PLoS One* 14, e0210248 (2019); and A. Gardet et al., LRRK2 Is Involved in the IFN-γ Response and Host Response to Pathogens. *The Journal of Immunology* 185, 5577 (2010)). Further, inhibition of LRRK2 kinase activity was reported to alleviate such enhanced oxidative stress. Consistent with these observations, incubation of RAW264.7 cells with LRIP4 resulted in a significant reduction of zymosan induced ROS production to an extent comparable to MLi-2 (FIG. 5A). The effect of LCIP1 on ROS production produced highly variable results, similar to its effects on dimerization in cells, thereby yielding no statistically significant consequence.

Figure 5B:
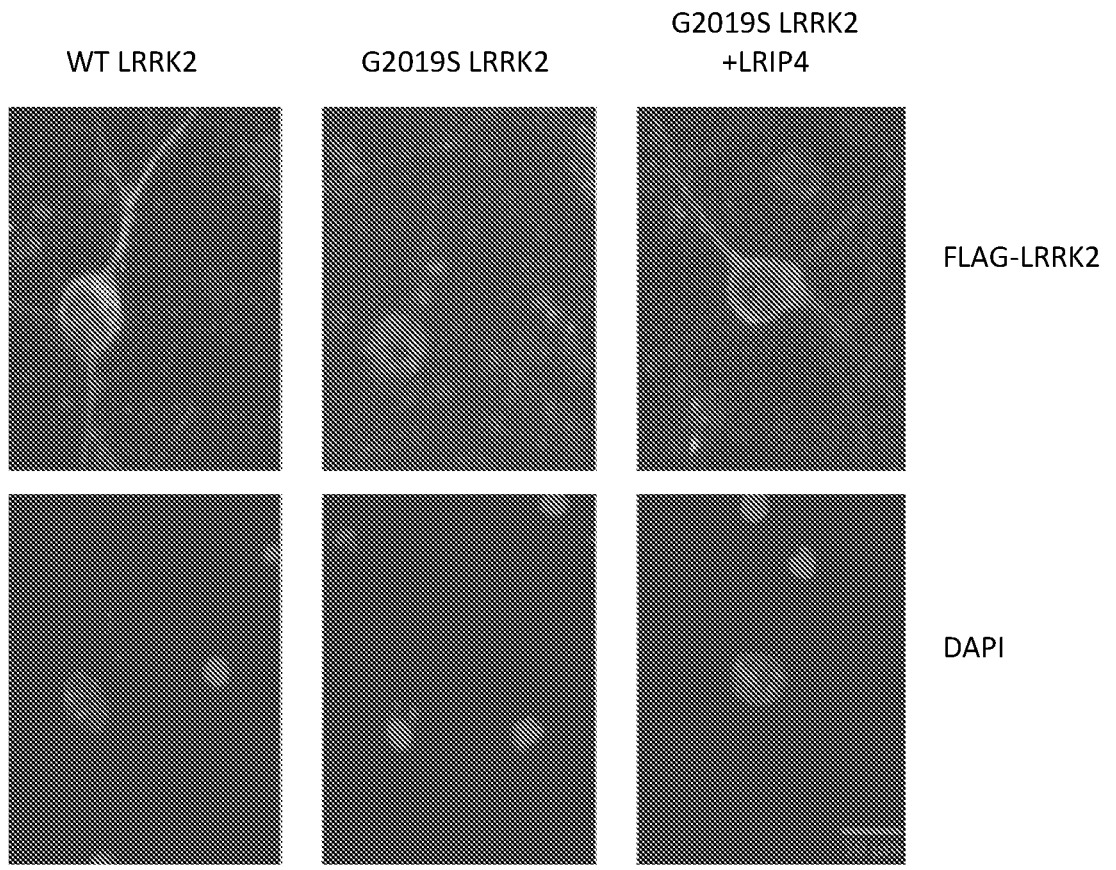
Figure 5C:
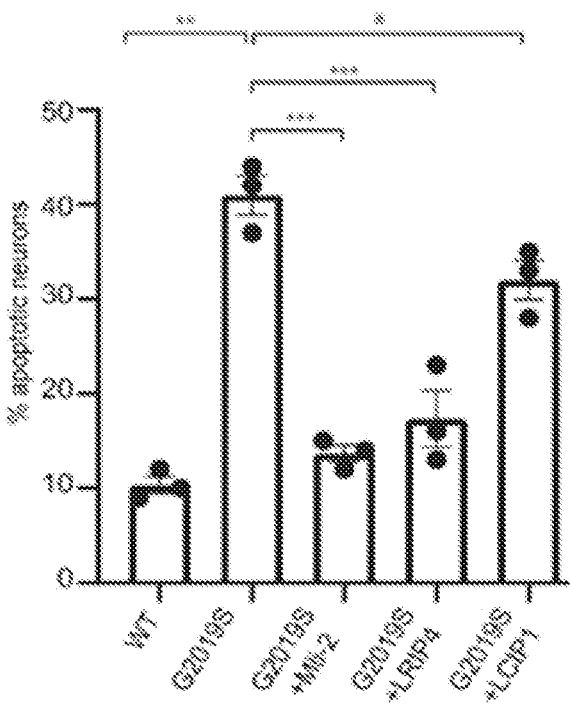

Finally, we used primary cortical neurons to assess the neuroprotective ability of LRIP4 and LCIP1. It has been shown that LRRK2-mediated neuronal toxicity is kinase-dependent (A. P. T. Nguyen et al., Dopaminergic neurodegeneration induced by Parkinson's disease-linked G2019S LRRK2 is dependent on kinase and GTPase activity. *Proc Natl Acad Sci USA* 117, 17296-17307 (2020)). To determine if peptide-treated cortical neurons maintained cellular integrity, fluorescence imaging was performed (G. Skibinski, K. Nakamura, M. R. Cookson, S. Finkbeiner, Mutant LRRK2 toxicity in neurons depends on LRRK2 levels and synuclein but not kinase activity or inclusion bodies. *J Neurosci* 34, 418-433 (2014)). Cortical neurons transfected with wild-type LRRK2 maintained proper cellular morphology, with no evidence of nuclear changes typical of apoptotic death, whereas neurons expressing G2019S LRRK2 exhibited aberrant LRRK2 distribution and apoptotic nuclear condensation and fragmentation (FIG. 5B). Importantly, upon treatment with the peptides, there was a sharp decline in neurons undergoing apoptosis, especially for LRIP4 treated cells (FIG. 5C). Together, these results indicate that disruption of dimerization with LRIP4 can effectively downregulate LRRK2-mediated ROS production and neuronal apoptosis.

Discussion

Although the normal function of LRRK2 is not fully understood, elevated kinase activity in both PD-linked mutations and idiopathic PD leads to neuronal degeneration. Further, inhibition of abnormally elevated activity of PD-associated LRRK2 can result in neuroprotection. Although LRRK2 has been sought after as a therapeutic target for PD, the ATP-competitive LRRK2 kinase inhibitors reported to date have largely led to altered LRRK2 localization as well as kidney and lung abnormalities in in vivo toxicological studies (M. C. Herzig et al., LRRK2 protein levels are determined by kinase function and are crucial for kidney and lung homeostasis in mice. *Hum Mol Genet* 20, 4209-4223 (2011); and M. A. Baptista et al., Loss of leucine-rich repeat kinase 2 (LRRK2) in rats leads to progressive abnormal phenotypes in peripheral organs. *PLoS One* 8, e80705 (2013)). Thus, alternative strategies to downregulate LRRK2 activity could present new opportunities for targeted therapeutic intervention.

LRRK2 was previously shown to alternate between monomeric and dimeric species where LRRK2 exists primarily as a dimer with enhanced kinase activity associated with the dimeric fractions of LRRK2 (S. Sen, P. J. Webber, A. B. West, Dependence of leucine-rich repeat kinase 2 (LRRK2) kinase activity on dimerization. *J Biol Chem* 284, 36346-36356 (2009)). Further, LRRK2 dimers were also shown to exist inside cells and are enriched at membranous structures with proportionally little dimeric LRRK2 in the cytosol (Z. Berger, K. A. Smith, M. J. LaVoie, Membrane Localization of LRRK2 Is Associated with Increased Formation of the Highly Active LRRK2 Dimer and Changes in Its Phosphorylation. *Biochemistry* 49, 5511-5523 (2010)). Further, LRRK2 kinase activity was found to be induced upon dimerization (E. Greggio et al., The Parkinson Disease-associated Leucine-rich Repeat Kinase 2 (LRRK2) Is a Dimer That Undergoes Intramolecular Autophosphorylation. *Journal of Biological Chemistry* 283, 16906-16914 (2008)) which is at least partly mediated by intermolecular interactions between the RocCOR tandem domains of two LRRK2 monomers. The mechanism regulating the balance between the monomer/dimer population is not known (V. Daniëls et al., Insight into the mode of action of the LRRK2 Y1699C pathogenic mutant. *Journal of Neurochemistry* 116, 304-315 (2011); and L. Civiero et al., Biochemical Characterization of Highly Purified Leucine-Rich Repeat Kinases 1 and 2 Demonstrates Formation of Homodimers. *PLOS ONE* 7, e43472 (2012)), although it is clear that GDP/GTP binding to the RocCOR domain plays a role in regulating this equilibrium (M. Leemans et al., Allosteric modulation of the GTPase activity of a bacterial LRRK2 homolog by conformation-specific Nanobodies. *Biochem J* 477, 1203-1218 (2020)). While most pathogenic variants of LRRK2 are associated with either increased kinase or decreased GTPase activity, it was also recently shown that wild-type LRRK2 kinase activity was enhanced in midbrain DA neurons of patients with idiopathic PD. Therefore, allosteric targeting of LRRK2 to regulate dimerization may serve as a strategy to shift from the dimer to monomer population and may be a viable alternative strategy for targeted inhibition of kinase activity, without altering its localization. It has been previously shown that disruption of dimerization using nanobodies can increase the GTPase activity in a bacterial homologue of LRRK2.

The present example shows the successful design, synthesis, and characterization of a peptide-based allosteric inhibitor of LRRK2 dimerization, namely LRIP4. LRIP4 was shown to permeate cells, inhibit dimerization and inhibit kinase activity both in vitro and in cells. Further, inhibition of dimerization also led to reduced ROS production and neuronal apoptosis. In addition, this example demonstrates for the first time that this inhibition strategy can downregulate kinase activity without inducing LRRK2 mislocalization that was previously shown by ATP-competitive kinase inhibitors of LRRK2. This example may be the first report of allosteric inhibition of LRRK2 dimerization and provides pharmacological evidence that LRRK2 dimerization regulates kinase activity. The second compound, LCIP1, which targeted the COR domain, showed limited cell uptake and binding affinity when compared to LRIP4. Although this compound showed some inhibitory activity in early biochemical assays, it had little to no activity in cells. Previous reports indicate that the COR domain is essential for mediating dimerization; therefore, optimization of this targeting site based on recent structural advances could result in a more potent disruptor of dimerization.

To further explore the potential for targeting LRRK2 dimerization, high-resolution structural insights into LRRK2 are required. Even though the exact function of the RocCOR domain is unknown, the present results demonstrate that disruption of RocCOR-mediated dimerization attenuates LRRK2 kinase activity. Recently published structures reveal many new interfaces that are critical for LRRK2 dimerization and may also serve as viable targets for LRRK2 inhibition. In addition, allosteric disruptors will be invaluable tools to dissect the different functions of the many domains of LRRK2 as we seek to better understand the significance of each domain on LRRK2 activity and regulation.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

A number of embodiments of the disclosure have been described. Nevertheless, it will be understood that various modifications may be made without departing from the spirit and scope of the invention. Accordingly, other embodiments are within the scope of the following claims.

What is claimed is:

1. A synthetic polypeptide comprising an amino acid sequence having an α-helical shape that mimics the Ras of complex proteins (ROC) domain of leucine-rich repeat kinase 2 (LRRK2), wherein the polypeptide comprises a variant of an amino acid sequence of SEQ ID NO. 1 or SEQ ID NO. 2 and wherein the variant comprises at least one pair of non-natural amino acids inserted into the amino acid sequence that are cross-linked to stabilize the α-helical shape.

2. The synthetic polypeptide of claim 1, wherein the polypeptide is formed from a peptide comprising an amino acid sequence selected from SEQ ID NO. 3 to 11.

3. The synthetic polypeptide of claim 1, wherein the polypeptide comprises a variant of an amino acid sequence of SEQ ID NO. 12, wherein the variant comprises at least one pair of non-natural amino acids that are cross-linked to stabilize the α-helical shape.

4. The synthetic polypeptide of claim 3, wherein the polypeptide is formed from a peptide comprising an amino acid sequence of SEQ ID NO. 13.

5. A synthetic polypeptide comprising an amino acid sequence having an α-helical shape that mimics the C-terminal of ROC (COR) domain of leucine-rich repeat kinase 2 (LRRK2), wherein the polypeptide comprises a variant of an amino acid sequence of SEQ ID NO. 14 or SEQ ID NO. 15 and wherein the variant comprises at least one pair of non-natural amino acids inserted into the amino acid sequence that are cross-linked to stabilize the α-helical shape.

6. The synthetic polypeptide of claim 5, wherein the polypeptide is formed from a peptide comprising an amino acid sequence selected from SEQ ID NO. 16 to 19.

7. The synthetic polypeptide of claim 5, wherein the polypeptide comprises a variant of an amino acid sequence of SEQ ID NO. 20, wherein the variant comprises at least one pair of non-natural amino acids that are cross-linked to stabilize the α-helical shape.

8. The synthetic polypeptide of claim 7, wherein the polypeptide is formed from a peptide comprising an amino acid sequence selected from SEQ ID NO. 21.

9. A pharmaceutical composition comprising the synthetic polypeptide of claim 1 in a pharmaceutically acceptable carrier.

10. A cell comprising the synthetic polypeptide of claim 1.

11. A pharmaceutical composition comprising the synthetic polypeptide of claim 5 in a pharmaceutically acceptable carrier.

12. A cell comprising the synthetic polypeptide of claim 5.

\* \* \* \* \*